US012570634B2

(12) United States Patent
Wu et al.

(10) Patent No.: US 12,570,634 B2
(45) Date of Patent: Mar. 10, 2026

(54) SMALL MOLECULE INHIBITORS OF UBIQUITIN SPECIFIC PROTEASE 1 (USP1) AND USES THEREOF

(71) Applicant: Insilico Medicine IP Limited, Hong Kong (HK)

(72) Inventors: Jianping Wu, Shanghai (CN); Luoheng Qin, Shanghai (CN); Jinxin Liu, Shanghai (CN)

(73) Assignee: Insilico Medicine IP Limited, Hong Kong (HK)

( * ) Notice: Subject to any disclaimer, the term of this patent is extended or adjusted under 35 U.S.C. 154(b) by 0 days.

(21) Appl. No.: 18/340,978

(22) Filed: Jun. 26, 2023

(65) Prior Publication Data

US 2024/0190839 A1    Jun. 13, 2024

Related U.S. Application Data

(63) Continuation of application No. 18/106,339, filed on Feb. 6, 2023, now Pat. No. 11,739,077, which is a continuation of application No. PCT/CN2022/131293, filed on Nov. 11, 2022.

(30) Foreign Application Priority Data

Nov. 12, 2021    (WO) ................ PCT/CN2021/130290
Oct. 8, 2022    (WO) ................ PCT/CN2022/123827

(51) Int. Cl.
| | |
|---|---|
| *C07D 401/14* | (2006.01) |
| *A61K 31/444* | (2006.01) |
| *A61K 31/506* | (2006.01) |
| *A61P 35/00* | (2006.01) |
| *C07D 471/04* | (2006.01) |

(52) U.S. Cl.
CPC .......... *C07D 401/14* (2013.01); *A61K 31/444* (2013.01); *A61K 31/506* (2013.01); *A61P 35/00* (2018.01); *C07D 471/04* (2013.01)

(58) Field of Classification Search
None
See application file for complete search history.

(56) References Cited

U.S. PATENT DOCUMENTS

| | | |
|---|---|---|
| 5,783,576 A | 7/1998 | Roos et al. |
| 5,846,514 A | 12/1998 | Foster et al. |
| 6,334,997 B1 | 1/2002 | Foster et al. |
| 7,078,522 B2 | 7/2006 | Yamada et al. |
| 11,413,288 B2 | 8/2022 | D'Andrea et al. |
| 11,739,077 B2 | 8/2023 | Wu et al. |
| 2017/0145012 A1 | 5/2017 | Buckmelter et al. |

FOREIGN PATENT DOCUMENTS

| | | |
|---|---|---|
| CN | 1503797 A | 6/2004 |
| CN | 104311555 A | 1/2015 |
| CN | 109311868 A | 2/2019 |
| EP | 4321515 A1 | 2/2024 |
| JP | 2004083587 A | 3/2004 |
| WO | 0039131 A1 | 7/2000 |
| WO | 02068419 A1 | 9/2002 |
| WO | 2004083587 A1 | 9/2004 |
| WO | 2008146914 A1 | 12/2008 |
| WO | 2010060854 A1 | 6/2010 |
| WO | 2011079118 A1 | 6/2011 |
| WO | 2011115804 A1 | 9/2011 |
| WO | 2011053861 A1 | 10/2011 |
| WO | 2012036997 A1 | 3/2012 |
| WO | 2013037415 A1 | 3/2013 |
| WO | 2014105952 A3 | 10/2014 |
| WO | 2016086200 A9 | 6/2016 |
| WO | 2017087837 A1 | 5/2017 |
| WO | 2017112777 A1 | 6/2017 |
| WO | 2017205538 A1 | 11/2017 |
| WO | 2018237084 A1 | 12/2018 |
| WO | 2019089216 A1 | 5/2019 |
| WO | 2020132269 A1 | 6/2020 |
| WO | 2020139988 A1 | 7/2020 |
| WO | 2021163530 A1 | 8/2021 |
| WO | 2021247606 A1 | 12/2021 |
| WO | 2022094096 A1 | 5/2022 |
| WO | 2022174031 A1 | 8/2022 |
| WO | 2022174184 A1 | 8/2022 |
| WO | 2022197892 A1 | 9/2022 |
| WO | 2022199652 A1 | 9/2022 |
| WO | 2022214053 A1 | 10/2022 |
| WO | 2022216820 A1 | 10/2022 |
| WO | 2023083285 A1 | 5/2023 |
| WO | 2023083286 A1 | 5/2023 |
| WO | 2023083297 A1 | 5/2023 |
| WO | 2024086790 A1 | 4/2024 |

OTHER PUBLICATIONS

Evans. Synthesis of radiolabeled compounds. J Radioanal Chem 64(1-2):9-32 (1981).
Fedorak, et al. A novel colon-specific steroid prodrug enhances sodium chloride absorption in rat colitis. Am J Physiol. Aug. 1995;269(2 Pt 1):G210-8.
Hochhaus et al. A selective HPLC/RIA for dexamethasone and its prodrug in biological fluids. Biomed. Chrom. 6:283-286 (1992).
International search report with written opinion dated Dec. 16, 2022 for PCT/CN2022/131293.
Kabalka et al. The Synthesis of Radiolabeled Compounds via Organometallic Intermediates. Tetrahedron 45(21):6601-6621 (1989).
Larsen et al. Prodrug forms for the sulfonamide group. I. Evaluation of N-acyl derivatives, N-sulfonylamindes, N-sulfonylsulfilimines and sulfonylureas as possible prodrug derivatives. Int. J. Pharmaceutics 37:87-95 (1987).
Larsen et al. Prodrug forms for the sulfonamide group. II. water-soluble amino acid derivatives of N-methylsulfonylamindes as possible prodrug derivatives. Int'l J of Pharmaceutics 47:103-110 (1988).

(Continued)

*Primary Examiner* — Brian J Davis
(74) *Attorney, Agent, or Firm* — Honigman LLP; Heidi M. Berven; Li Gao

(57) ABSTRACT

The disclosure provides for small molecules inhibitory compounds of ubiquitin specific protease 1 (USP1) and compositions comprising the same. The disclosure further provides methods for targeting ubiquitin specific protease 1 (USP1) and methods of treating diseases or disorders related to USP1, such as cancer.

11 Claims, No Drawings

(56) References Cited

OTHER PUBLICATIONS

Lim, et al. USP1 is Required for Replication Fork Protection in BRCA1-Deficient Tumors. Mol Cell. Dec. 20, 2018;72(6):925-941. e4. doi: 10.1016/j.molcel.2018.10.045.

Mcloed et al. A Glucocorticoid Prodrug Facilitates Normal Mucosal Function in Rat Colitis Without Adrenal Suppression. Gastroenterol 106:405-413 (1994).

RN 2650175-41-8, 2650060-76-5, 2415878-57-6, 2415796-42-6, 2415773-68-9, 2096126-45-1, 2096029-49-9, 1185473-57-7 STN Registry Jul. 7, 2021 (Jul. 7, 2021).

Sinkula et al. Rationale for design of biologically reversible drug derivatives: prodrugs. J. Pharm. Sci. 64:181-210 (1975).

Wang, et al. Discovery of 5-Azaindazole (GNE-955) as a Potent Pan-Pim Inhibitor with Optimized Bioavailability. J Med Chem. May 25, 2017;60(10):4458-4473. doi: 10.1021/acs.jmedchem. 7b00418. Epub May 5, 2017.

Larsen et al. Prodrug forms for the sulfonamide group. I. Evaluation of N-acyl derivatives, N-sulfonylamidines, N-sulfonylsulfilimines and sulfonylureas as possible prodrug derivatives. International Journal of Pharmaceutics, 37(1987) 87-95.

SMALL MOLECULE INHIBITORS OF UBIQUITIN SPECIFIC PROTEASE 1 (USP1) AND USES THEREOF

CROSS REFERENCE TO RELATED APPLICATIONS

This patent application is a continuation of U.S. patent application Ser. No. 18/106,339, filed Feb. 6, 2023, which is a continuation application of International Application No. PCT/CN2022/131293, filed Nov. 11, 2022, which claims the benefit of International Application No. PCT/CN2021/130290, filed Nov. 12, 2021 and International Application No. PCT/CN2022/123827, filed Oct. 8, 2022, each of which is incorporated herein by reference in its entirety.

BACKGROUND

Ubiquitin specific protease 1 (USP1) is a gene that plays a role in a DNA damage repair. Compounds and pharmaceutical compositions targeting USP1, and methods of treatment for USP1-related diseases and disorders, like certain cancers, have not been widely developed. Therefore, there remains a need to address methods of treating USP1-related diseases.

SUMMARY

The present disclosure addresses the above need and provides additional advantages as well.

In one aspect, described herein is a compound having the structure of Formula (IVa), or a salt or solvate thereof.

Formula (IVa)

wherein, $Y^1$ is N or $CR^{Y1}$;

$Y^2$ is N or $CR^{Y2}$;

$Y^3$ is N or $CR^{Y3}$;

$Y^4$ is N or $CR^{Y4}$;

$R^1$ is hydrogen, —CN, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, optionally substituted $C_{3-8}$ cycloalkyl, or optionally substituted $C_{2-7}$ heterocycloalkyl;

each of $R^4$ and $R^{4'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^4$ and $R^{4'}$ taken together form an oxo; or $R^4$ and $R^{4'}$ taken together with the carbon to which they are attached form a 3-6 membered cycloalkyl or 3-6 membered heterocycloalkyl;

each of $R^5$ and $R^{5'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^5$ and $R^{5'}$ taken together form an oxo; or $R^5$ and $R^{5'}$ taken together with the carbon to which they are attached form a 3-6 membered cycloalkyl or 3-6 membered heterocycloalkyl;

each of $R^6$ and $R^{6'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^6$ and $R^{6'}$ taken together form an oxo; or $R^6$ and $R^{6'}$ taken together with the carbon to which they are attached form a 3-6 membered cycloalkyl or 3-6 membered heterocycloalkyl;

each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl; or $R^8$ and $R^9$ taken together with the carbon to which they are attached form an optionally substituted 3-6 membered cycloalkyl or 3-6 membered heterocycloalkyl;

ring A is monocyclic heteroaryl, bicyclic heteroaryl, monocyclic heterocycloalkyl, or bicyclic heterocycloalkyl;

each of $R^4$ is independently selected from halogen, —$NO_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$;

$R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl;

each of $R^{12}$ is independently selected from hydrogen, —$NO_2$, —CN, $C_{1-6}$ alkyl, $C_{1-6}$ aminoalkyl, $C_{1-6}$ hydroxyalkyl, $C_{1-6}$ haloalkyl, $C_{1-6}$ heteroalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, —CN, $C_{1-6}$ alkyl, $C_{1-6}$ alkoxy, and $C_{1-6}$ haloalkyl;

$R^{B1}$ is optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, or optionally substituted bicyclic heteroaryl;

each of $R^{Y1}$, $R^2$, $R^{Y3}$ and $R^{Y4}$ is independently selected from hydrogen, halo, —CN, —NO$_2$, —OR$^{11}$, —SR$^{11}$, —N(R$^{12}$)(R$^{11}$), optionally substituted C$_{1-6}$ alkyl, optionally substituted C$_{1-6}$ heteroalkyl, optionally substituted C$_{2-6}$ alkenyl, optionally substituted C$_{2-6}$ alkynyl, —OR$^{11}$, —SR$^{11}$, —N(R$^{12}$)(R$^{11}$), —C(O)R$^{12}$, —C(O)OR$^{12}$, —OC(O)R$^{12}$, —OC(O)N(R$^{12}$)(R$^{11}$), —C(O)N(R$^{12}$)(R$^{11}$), —N(R$^{12}$)C(O)R$^{12}$, —N(R$^{12}$)C(O)OR$^{12}$, —N(R$^{12}$)C(O)N(R$^{12}$)(R$^{11}$), —N(R$^{12}$)S(O)$_2$(R$^{12}$), —S(O)R$^{12}$, —S(O)$_2$R$^{12}$, —S(O)$_2$N(R$^{12}$)(R$^{11}$), optionally substituted C$_{3-8}$ cycloalkyl, optionally substituted C$_{2-9}$ heterocycloalkyl, optionally substituted naphthyl, optionally substituted phenyl, optionally substituted monocyclic heteroaryl, and optionally substituted bicyclic heteroaryl; or $R^{Y1}$ and $R^{Y2}$ are taken together with the carbons to which they are attached to form an optionally substituted C$_{3-8}$ cycloalkyl or optionally substituted C$_{2-9}$ heterocycloalkyl; or R$^{Y3}$ and R$^{Y4}$ are taken together with the carbons to which they are attached to form an optionally substituted C$_{3-8}$ cycloalkyl or optionally substituted C$_{2-9}$ heterocycloalkyl;

m is 0, 1, 2, 3, or 4; and p is 0 or 1.

In some embodiments, the compound has a structure of Formula (IVa-1),

Formula (IVa-1)

In some embodiments, the compound has a structure of Formula (IVa-2),

Formula (IVa-2)

In one aspect, described herein is a compound having the structure of Formula (VI), or a salt or solvate thereof, Formula (VI)

wherein, ring C is an optionally substituted 5 membered heteroaryl;

ring D is an aromatic, saturated or partially saturated 6 membered carbocycle or heterocycle, wherein each of the carbocycle or heterocycle is optionally substituted;

each of R$^8$ and R$^9$ is independently selected from hydrogen, halo, —CN, optionally substituted C$_{1-6}$ alkyl, optionally substituted C$_{1-6}$ heteroalkyl, optionally substituted C$_{2-6}$ alkenyl, and optionally substituted C$_{2-6}$ alkynyl; or R$^8$ and R$^9$ taken together form an oxo; or R$^8$ and R$^9$ taken together with the carbon to which they are attached form an optionally substituted 3-6 membered cycloalkyl or heterocycloalkyl;

ring A is phenyl, naphthyl, monocyclic heteroaryl, bicyclic heteroaryl, cycloalkyl or heterocycloalkyl;

each of R$^4$ is independently selected from halogen, —NO$_2$, oxo, —CN, optionally substituted C$_{1-6}$ alkyl, optionally substituted C$_{2-6}$ alkenyl, optionally substituted C$_{2-6}$ alkynyl, optionally substituted C$_{1-6}$ heteroalkyl, optionally substituted C$_{3-8}$ cycloalkyl, optionally substituted C$_{2-7}$ heterocycloalkyl, —OR$^{11}$, —SR$^{11}$, —N(R$^{12}$)(R$^{11}$), —C(O)R$^{12}$, —C(O)OR$^{12}$, —OC(O)R$^{12}$, —OC(O)N(R$^{12}$)(R$^{11}$), —C(O)N(R$^{12}$)(R$^{11}$), —N(R$^{12}$)C(O)R$^{12}$, —N(R$^{12}$)C(O)OR$^{12}$, —N(R$^{12}$)C(O)N(R$^{12}$)(R$^{11}$), —N(R$^{12}$)$_2$S(O)$_2$(R$^{12}$), —S(O)R$^{12}$, —S(O)$_2$R$^{12}$, and —S(O)$_2$N(R$^{12}$)(R$^{11}$);

R$^{11}$ is hydrogen, optionally substituted C$_{1-6}$ alkyl, optionally substituted C$_{2-6}$ alkenyl, optionally substituted C$_{2-6}$ alkynyl, optionally substituted C$_{1-6}$ heteroalkyl, optionally substituted C$_{3-8}$ cycloalkyl, optionally substituted C$_{2-7}$ heterocycloalkyl, optionally substituted phenyl, optionally substituted heteroaryl, optionally substituted —C$_{1-4}$ alkylene-C$_{3-8}$ cycloalkyl, optionally substituted —C$_{1-4}$ alkylene-C$_{2-7}$ heterocycloalkyl, optionally substituted —C$_{1-4}$ alkylene-phenyl, or optionally substituted —C$_{1-4}$ alkylene-heteroaryl;

each of R$^{12}$ is independently selected from hydrogen, —NO$_2$, —CN, C$_{1-6}$ alkyl, C$_{1-6}$ aminoalkyl, C$_{1-6}$ hydroxyalkyl, C$_{1-6}$ haloalkyl, and C$_{3-6}$ carbocycle, 3- to 6-membered heterocycle, wherein the C$_{3-6}$ carbocycle and 3- to 6-membered heterocycle is optionally substituted with one or more substituents independently selected from halogen, —OH, oxo, amino, —NO$_2$, —CN, C$_{1-6}$ alkyl, C$_{1-6}$ alkoxy, and C$_{1-6}$ haloalkyl;

R$^B$ is hydrogen, halo, —CN, —NO$_2$, optionally substituted C$_{1-6}$ alkyl, optionally substituted C$_{2-6}$ alkenyl, optionally substituted C$_{2-6}$ alkynyl, optionally substituted C$_{1-6}$ heteroalkyl, —OR$^{11}$, —SR$^{11}$, —N(R$^{12}$)(R$^{11}$), —C(O)R$^{12}$, —C(O)OR$^{12}$, —OC(O)R$^{12}$, —OC(O)N(R$^{12}$)(R$^{11}$), —C(O)N(R$^{12}$)(R$^{11}$), —N(R$^{12}$)C(O)R$^{12}$, —N(R$^{12}$)C(O)OR$^{12}$, —N(R$^{12}$)C(O)N(R$^{12}$)(R$^{11}$), —N(R$^{12}$)S(O)$_2$(R$^{12}$), —S(O)R$^{12}$, —S(O)$_2$R$^{12}$, —S(O)$_2$N(R$^{12}$)(R$^{11}$), optionally substituted C$_{3-8}$ cycloalkyl, optionally substituted C$_{2-9}$ heterocycloalkyl, optionally substituted naphthyl, optionally substituted phenyl, optionally substituted monocyclic heteroaryl, or optionally substituted bicyclic heteroaryl;

m is 1, 2, 3, or 4; and p is 0 or 1.

In one aspect, described herein is a pharmaceutical composition comprising a compound described herein or a pharmaceutically acceptable salt or solvate thereof, and a pharmaceutically acceptable carrier or excipient.

In one aspect, described herein is a method of modulating ubiquitin specific protease 1 (USP1) in a subject, the method comprising administering to a subject a compound described herein, or a pharmaceutically acceptable salt or solvate thereof, or a pharmaceutical composition of a compound described herein.

In one aspect, described herein is a method of inhibiting ubiquitin specific protease 1 (USP1) in a subject, the method comprising administering to the subject a compound described herein, or a pharmaceutically acceptable salt or solvate thereof, or a pharmaceutical composition of a compound described herein.

In one aspect, described herein is a method of inhibiting or reducing DNA repair activity modulated by ubiquitin specific protease 1 (USP1) in a subject, the method comprising administering to the subject in need thereof an effective amount of a compound described herein, or a pharmaceutically acceptable salt or solvate thereof, or a pharmaceutical composition of a compound described herein.

In one aspect, described herein is a method of treating a disease or disorder associated with ubiquitin specific protease 1 (USP1) in a subject, the method comprising administering to the subject a compound described herein, or a pharmaceutically acceptable salt or solvate thereof, or a pharmaceutical composition of a compound described herein.

In one aspect, described herein is a method of treating a disease or disorder associated with modulation of ubiquitin specific protease 1 (USP1) in a subject, the method comprising administering to the subject a compound described herein, or a pharmaceutically acceptable salt or solvate thereof, or a pharmaceutical composition of a compound described herein. In some embodiments, the disease or disorder is cancer.

In one aspect, described herein is a method of treating cancer in a subject, the method comprising administering to the subject in need thereof an effective amount of a compound described herein, or a pharmaceutically acceptable salt or solvate thereof, or a pharmaceutical composition of a compound described herein. In some embodiments, the cancer is selected from the group consisting of lung cancer, non-small cell lung cancer (NSCLC), colon cancer, bladder cancer, osteosarcoma, ovarian cancer, skin cancer, and breast cancer. In some embodiments, the cancer is ovarian cancer. In some embodiments, the cancer is a breast cancer. In some embodiments, the cancer is a ovarian cancer or breast cancer.

In some embodiments, the cancer comprises cancer cells with elevated levels of RAD 18. In some embodiments, the cancer is a DNA damage repair pathway deficient cancer. In some embodiments, the cancer is a PARP inhibitor resistant or refractory cancer. In some embodiments, the cancer is a BRCA1 mutant cancer and/or a BRCA2 mutant cancer. In some embodiments, the cancer is a BRAC1-deficient cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION

While various embodiments of the disclosure have been shown and described herein, it will be obvious to those skilled in the art that such embodiments are provided by way of example only. Numerous variations, changes, and substitutions can occur to those skilled in the art without departing from the disclosure. It should be understood that various alternatives to the embodiments of the disclosure described herein can be employed.

A. Definitions

Unless defined otherwise, all technical and scientific terms used herein have the same meaning as is commonly understood by one of skill in the art to which this disclosure belongs. All patents and publications referred to herein are incorporated by reference.

"Alkyl" refers to an optionally substituted straight-chain, or optionally substituted branched-chain saturated hydrocarbon mono-radical, and preferably having from one to fifteen carbon atoms (i.e., $C_1$-$C_{15}$ alkyl). In certain embodiments, an alkyl comprises one to thirteen carbon atoms (i.e., $C_1$-$C_{13}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). Whenever it appears herein, a numerical range such as "$C_1$-$C_3$ alkyl" means that the alkyl group consists of 1 carbon atom, 2 carbon atoms, or 3 carbon atoms. In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). In other embodiments, examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl, and hexyl, and longer alkyl groups, such as heptyl, octyl, and the like. The alkyl is attached to the rest of the molecule by a single bond. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, —$NO_2$, or —C≡CH. In some embodiments, the alkyl is optionally substituted with oxo, halogen, —CN, —$CF_3$, —OH, or —OMe. In some embodiments, the alkyl is optionally substituted with halogen such as F.

As used herein, $C_1$-$C_x$ (or $C_{1-x}$) includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms.

Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Also, by way of example, $C_0$-$C_2$ alkylene includes a direct bond, —CH$_2$—, and —CH$_2$CH$_2$— linkages.

"Alkoxy" refers to a radical bonded through an oxygen atom of the formula —O-alkyl, where alkyl is an alkyl chain as defined above. Unless stated otherwise specifically in the specification, an alkoxy group can be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Alkenyl" refers to an optionally substituted straight or branched hydrocarbon chain radical group containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The group can be in either the cis or trans configuration about the double bond(s), and should be understood to include both isomers. Examples include, but are not limited to, ethenyl (—CH═CH$_2$), 1-propenyl (—CH$_2$CH═CH$_2$), isopropenyl[-C(CH$_3$) ═CH$_2$], butenyl, 1,3-butadienyl, and the like. Whenever it appears herein, a numerical range such as "$C_2$-$C_6$ alkenyl" means that the alkenyl group can consist of 2 carbon atoms, 3 carbon atoms, 4 carbon atoms, 5 carbon atoms, or 6 carbon atoms. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen.

"Alkynyl" refers to an optionally substituted straight or branched hydrocarbon chain radical group containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). Whenever it appears herein, a numerical range such as "$C_2$-$C_6$ alkynyl" means that the alkynyl group can consist of 2 carbon atoms, 3 carbon atoms, 4 carbon atoms, 5 carbon atoms, or 6 carbon atoms. The alkynyl is attached to the rest of the molecule by a single bond, for example, ethynyl, propynyl, butynyl, pentynyl, hexynyl, 2-propynyl, 2-butynyl, 1,3-butadiynyl, and the like. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —CF$_3$, —OH, —OMe, —NH$_2$, or —NO$_2$. In some embodiments, an alkynyl is optionally substituted with oxo, halogen, —CN, —CF$_3$, —OH, or —OMe. In some embodiments, the alkynyl is optionally substituted with halogen.

"Alkylene" or "alkylene chain" refers to an optionally substituted straight or branched divalent hydrocarbon chain linking the rest of the molecule to a radical group containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through any two carbons within the chain. In certain embodiments, an alkylene comprises one to ten carbon atoms (i.e., $C_1$-$C_8$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene). Unless stated otherwise specifically in the specification, an alkylene group can be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or —OMe. In some embodiments, the alkylene is optionally substituted with halogen. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Aryl" refers to a radical derived from a hydrocarbon ring system comprising at least one aromatic ring. In some embodiments, an aryl comprises hydrogens and 6 to 30 carbon atoms. The aryl radical can be a monocyclic, bicyclic, tricyclic, or tetracyclic ring system, which can include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, indane, indene, naphthalene, phenalene, phenanthrene, pleiadene, pyrene, and triphenylene. In some embodiments, the aryl is phenyl. Unless stated otherwise specifically in the specification, an aryl can be optionally substituted, for example, with halogen, amino, alkylamino, aminoalkyl, nitrile, nitro, hydroxyl, alkyl, alkenyl, alkynyl, haloalkyl, heteroalkyl, alkoxy, aryl, cycloalkyl, heterocycloalkyl, heteroaryl, —S(O)$_2$NH—C$_1$-C$_6$alkyl, and the like. In some embodiments, an aryl is optionally substituted with halogen, methyl, ethyl, —CN, —CF$_3$, —OH, —OMe, —NH$_2$, —NO$_2$, —S(O)$_2$NH$_2$, —S(O)$_2$NHCH$_3$, —S(O)$_2$NHCH$_2$CH$_3$, —S(O)$_2$NHCH(CH$_3$)$_2$, —S(O)$_2$N (CH$_3$)$_2$, or —S(O)$_2$NHC(CH$_3$)$_3$. In some embodiments, an aryl is optionally substituted with halogen, methyl, ethyl, —CN, —CF$_3$, —OH, or —OMe. In some embodiments, the aryl is optionally substituted with halogen. In some embodiments, the aryl is substituted with alkyl, alkenyl, alkynyl, haloalkyl, or heteroalkyl, wherein each alkyl, alkenyl, alkynyl, haloalkyl, heteroalkyl is independently unsubstituted, or substituted with halogen, methyl, ethyl, —CN, —CF$_3$, —OH, —OMe, —NH$_2$, or —NO$_2$.

"Aralkyl" refers to a radical of the formula —R$^c$-aryl where R$^c$ is an alkylene chain as defined above, for example, methylene, ethylene, and the like.

"Aralkenyl" refers to a radical of the formula —R$^d$-aryl where R$^d$ is an alkenylene chain as defined above. "Aralkynyl" refers to a radical of the formula —Re-aryl, where Re is an alkynylene chain as defined above.

"Carbocycle" refers to a saturated, unsaturated or aromatic rings in which each atom of the ring is carbon. Carbocycle can include 3- to 10-membered monocyclic rings and 6- to 12-membered bicyclic rings (such as spiro, fused, or bridged rings). Each ring of a bicyclic carbocycle can be selected from saturated, unsaturated, and aromatic rings. An aromatic ring, e.g., phenyl, can be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. In an exemplary embodiment, an aromatic ring, e.g., phenyl, can be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-5 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl. The term "unsaturated carbocycle" refers to carbocycles with at least one degree of unsaturation and excluding aromatic carbocycles. Examples of unsaturated carbocycles include cyclohexadiene, cyclohexene, and cyclopentene. The term "saturated cycloalkyl" as used herein refers to a saturated carbocycle. Exemplary carbocycles include cyclopropyl, cyclopentyl, cyclohexyl, cyclohexenyl, adamantyl, phenyl, indanyl, norborane, and naphthyl. Carbocycles can be optionally substituted by one or more substituents such as those substituents described herein.

"Cycloalkyl" refers to a stable, partially or fully saturated, monocyclic or polycyclic carbocyclic ring, which can include fused (when fused with an aryl or a heteroaryl ring, the cycloalkyl is bonded through a non-aromatic ring atom), bridged, or spiro ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0] nonane, cis-decalin, trans-decalin, bicyclo[2.1.1]hexane, bicyclo[2.2.1]heptane, bicyclo[2.2.2]octane, bicyclo[3.2.2] nonane, and bicyclo[3.3.2]decane, and 7,7-dimethyl-bicyclo [2.2.1]heptanyl. Partially saturated cycloalkyls include, for example, cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Cycloalkylalkyl" refers to a radical of the formula —R$^c$-cycloalkyl where R$^c$ is an alkylene chain as described above.

"Cycloalkylalkoxy" refers to a radical bonded through an oxygen atom of the formula —O—R$^c$-cycloalkyl where R$^c$ is an alkylene chain as described above.

"Halo" or "halogen" refers to halogen substituents such as bromo, chloro, fluoro and iodo substituents.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen can be independently selected e.g., 1-chloro,2-fluoroethane.

"Fluoroalkyl" refers to an alkyl radical, as defined above, that is substituted by one or more fluoro radicals, for example, trifluoromethyl, difluoromethyl, fluoromethyl, 2,2, 2-trifluoroethyl, 1-fluoromethyl-2-fluoroethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxy-butyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

The term "heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, or —CH(CH$_3$)OCH$_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a stable 3- to 24-membered partially or fully saturated ring radical comprising 2 to 23 carbon atoms and at least one ring heteroatoms. In some embodiments, a heterocycloalkyl contains from one to 8 heteroatoms selected from the group consisting of nitrogen, oxygen, phosphorous, and sulfur. Unless stated otherwise specifically in the specification, the heterocycloalkyl radical can be a monocyclic, bicyclic, tricyclic, or tetracyclic ring system, which can include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical can be optionally oxidized; the nitrogen atom can be optionally quaternized.

Representative heterocycloalkyls include, but are not limited to, heterocycloalkyls having from two to fifteen carbon atoms (C$_2$-C$_{15}$ heterocycloalkyl), from two to ten carbon atoms (C$_2$-C$_{10}$ heterocycloalkyl), from two to eight carbon atoms (C$_2$-C$_8$ heterocycloalkyl), from two to six carbon atoms (C$_2$-C$_6$ heterocycloalkyl), from two to five carbon atoms (C$_2$-C$_5$ heterocycloalkyl), or two to four carbon atoms (C$_2$-C$_4$ heterocycloalkyl). In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to, the monosaccharides, the disaccharides, and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heterocycle" or "heterocyclyl" refers to a saturated, unsaturated or aromatic ring comprising one or more ring heteroatoms. Exemplary heteroatoms include N, O, Si, P, B, and S atoms. Heterocycles include e.g., 3- to 10-membered monocyclic rings and 6- to 12-membered bicyclic rings (such as spiro, fused, or bridged rings). Unless stated otherwise specifically in the specification, the heterocyclyl radical is a monocyclic, bicyclic, tricyclic or tetracyclic ring system, which optionally includes fused, bridged, or spirocyclic ring systems. The heteroatoms in the heterocyclyl radical are optionally oxidized. One or more nitrogen atoms, if present, are optionally quaternized. The heterocyclyl radical can be partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted. For example, a heterocyclyl can be optionally substituted by one or more substituents by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—CN, —R$^b$—O—Re—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^e$—S(O)$_t$R$^a$ (where t is 1 or 2), —R$^e$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^e$ is a straight or branched alkylene or alkenylene chain, and where each of the above substituents is unsubstituted unless otherwise indicated.

"Heteroaryl" or "aromatic heterocycle" refers to a ring system radical comprising carbon atom(s) and one or more ring heteroatoms (e.g., selected from the group consisting of nitrogen, oxygen, phosphorous, silicon, and sulfur), and at least one aromatic ring. In some embodiments, a heteroaryl is a 5- to 14-membered ring system radical comprising one to thirteen carbon atoms, one to six heteroatoms selected from the group consisting of nitrogen, oxygen, phosphorous, and sulfur. The heteroaryl radical can be a monocyclic, bicyclic, tricyclic, or tetracyclic ring system, which can include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical can be optionally oxidized; the nitrogen atom can be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen can have hydrogen substituents and/or any permissible substituents of organic compounds described herein which satisfy the valences of the heteroatoms.

In some embodiments, substituents can include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^e$—S(O)$_t$OR$^a$ (where t is 1 or 2), and —R$^e$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, and heterocycle, any of which can be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), SF$^5$, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, and heterocycle, wherein each R$^a$, valence permitting, can be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^e$—S(O)$_t$R$^a$ (where t is 1 or 2), —R$^e$—S(O)$_t$OR$^a$ (where t is 1 or 2) and —R$^b$—S(O)$_t$N(R$^a$)$_2$ (where t is 1 or 2); and wherein each R$^e$ is independently selected from a direct bond or a straight or branched alkylene, alkenylene, or alkynylene chain, and each R$^e$ is a straight or branched alkylene, alkenylene or alkynylene chain.

As used in the specification and claims, the singular form "a", "an" and "the" includes plural references unless the context clearly dictates otherwise.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder can refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treat," "treating" or "treatment," as used herein, can include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group can be un-substituted (e.g., $-CH_2CH_3$), fully substituted (e.g., $-CF_2CF_3$), mono-substituted (e.g., $-CH_2CH_2F$) or substituted at a level anywhere in-between fully substituted and mono-substituted (e.g., $-CH_2CHF_2$, $-CH_2CF_3$, $-CF_2CH_3$, $-CFHCHF_2$, etc.).

As used herein, the term "subject" can be a vertebrate, such as a mammal, a fish, a bird, a reptile, or an amphibian. Thus, the subject of the herein disclosed methods can be a human, non human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 can comprise 1 to 10, 1 to 20, 1 to 30, and 1 to 40 in one direction, or 50 to 40, 50 to 30, 50 to 20, and 50 to 10 in the other direction.

B. Compounds of the Disclosure

In one aspect, the disclosure provides a compound represented by Formula (IVa), or a pharmaceutically acceptable salt or solvate thereof:

Formula (IVa)

wherein, $Y^1$ is N or $CR^{Y1}$;

$Y^2$ is N or $CR^{Y2}$;

$Y^3$ is N or $CR^{Y3}$;

$Y^4$ is N or $CR^{Y4}$;

each of $R^1$ is independently selected from hydrogen, halo, —CN, —$OR^{11}$, —$SR^{11}$, —$N(R^{12})(R^{11})$ optionally substituted $C_{1-6}$ alkyl, optionally substituted $C_{1-6}$ heteroalkyl, optionally substituted $C_{2-6}$ alkenyl, and optionally substituted $C_{2-6}$ alkynyl, optionally substituted $C_{3-8}$ cycloalkyl, or optionally substituted $C_{2-7}$ heterocycloalkyl;

each of $R^4$ and $R^{4'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{1-6}$ alkenyl, optionally substituted $C_{1-6}$ alkynyl, optionally substituted $C_{3-8}$ cycloalkyl, and optionally substituted $C_{2-7}$ heterocycloalkyl; or $R^4$ and $R^{4'}$ taken together form an oxo; or $R^4$ and $R^{4'}$ taken together with the carbon to which they are attached form a 3-6 membered cycloalkyl or 3-6 membered heterocycloalkyl;

each of $R^5$ and $R^{5'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{1-6}$ alkenyl, optionally substituted $C_{1-6}$ alkynyl, optionally substituted $C_{3-8}$ cycloalkyl, and optionally substituted $C_{2-7}$ heterocycloalkyl; or $R^5$ and $R^{5'}$ taken together form an oxo; or $R^5$ and $R^{5'}$ taken together with the carbon to which they are attached form a 3-6 membered cycloalkyl or 3-6 membered heterocycloalkyl;

each of $R^6$ and $R^{6'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{1-6}$ alkenyl, alkenyl, optionally substituted $C_{1-6}$ alkynyl, optionally substituted $C_{3-8}$ cycloalkyl, and optionally substituted $C_{2-7}$ heterocycloalkyl; or $R^6$ and $R^{6'}$ taken together form an oxo; or $R^6$ and $R^{6'}$ taken together with the carbon to which they are attached form a 3-6 membered cycloalkyl or 3-6 membered heterocycloalkyl;

each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl; or $R^8$ and $R^9$ taken together with the carbon to which they are attached form an optionally substituted 3-6 membered cycloalkyl or heterocycloalkyl; ring A is monocyclic heteroaryl, bicyclic heteroaryl, monocyclic heterocycloalkyl, or bicyclic heterocycloalkyl;

each of $R^A$ is independently selected from halogen, —$NO_2$, oxo, CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, $C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$;

$R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl;

each of $R^{12}$ is independently selected from hydrogen, halogen, —OH, —$NO_2$, CN, $C_{1-6}$ alkyl, $C_{1-6}$ aminoalkyl, $C_{1-6}$ hydroxyalkyl, $C_{1-6}$ haloalkyl, $C_{1-6}$ heteroalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, CN, $C_{1-6}$ alkyl, $C_{1-6}$ alkoxy, and $C_{1-6}$ haloalkyl;

$R^{B1}$ is optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, or optionally substituted bicyclic heteroaryl;

each of $R^{Y1}$, $R^2$, $R^{Y3}$ and $R^{Y4}$ is independently selected from hydrogen, halo, —CN, —$NO_2$, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, —$OR^{11}$, —$SR^{11}$, —$N(R^{12})(R^{11})$, —$C(O)R^{12}$, $C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$, optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, and optionally substituted bicyclic heteroaryl; or $R^{Y1}$ and $R^{Y2}$ are taken together with the carbons to which they are attached to form an optionally substituted $C_{3-8}$ cycloalkyl or optionally substituted $C_{2-9}$ heterocycloalkyl; or $R^{Y3}$ and $R^{Y4}$ are taken together with the carbons to which they are attached to form an optionally substituted $C_{3-8}$ cycloalkyl or optionally substituted $C_{2-9}$ heterocycloalkyl;

m is 0, 1, 2, 3, or 4; and p is 0 or 1.

In some embodiments of Formula (IVa), each of $R^4$ and $R^{4'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^4$ and $R^{4'}$ taken together form an oxo; or $R^4$ and $R^{4'}$ taken together with the carbon to which they are attached form a 3-6 membered cycloalkyl or 3-6 membered heterocycloalkyl. In some embodiments, each of $R^5$ and $R^{5'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^5$ and $R^{5'}$ taken together form an oxo; or $R^5$ and $R^{5'}$ taken together with the carbon to which they are attached form a 3-6 membered cycloalkyl or 3-6 membered heterocycloalkyl. In some embodiments, each of $R^6$ and $R^{6'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^6$ and $R^{6'}$ taken together form an oxo; or $R^6$ and $R^{6'}$ taken together with the carbon to which they are attached form a 3-6 membered cycloalkyl or 3-6 membered heterocycloalkyl.

In some embodiments, the compound of Formula (IVa), (IVa-1), and (IVa-2),

Y$^1$ is N or CR$^{Y1}$;

Y$^2$ is N or CR$^{Y2}$;

Y$^3$ is N or CR$^{Y3}$;

Y$^4$ is N or CR$^{Y4}$;

each of $R^1$ is hydrogen, halo, —CN, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl, optionally substituted $C_{3-8}$ cycloalkyl, or optionally substituted $C_{2-7}$ heterocycloalkyl;

wherein the alkyl, heteroalkyl, alkenyl, or alkynyl is optionally substituted with one or more substituents independently selected from: halogen, amino, oxo, —OH, —$NO_2$, —CN, and $C_{1-3}$ alkoxyl;

each of $R^4$ and $R^{4'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{1-6}$ alkenyl, optionally substituted $C_{1-6}$ alkynyl, optionally substituted $C_{3-8}$ cycloalkyl, and optionally substituted $C_{2-7}$ heterocycloalkyl, or $R^4$ and $R^{4'}$ taken together form an oxo, or $R^4$ and $R^{4'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —$NO_2$, oxo, —CN, $C_{1-3}$ alkoxyl, $C_{1-3}$ alkyl and $C_{1-3}$ haloalkyl;

each of $R^5$ and $R^{5'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{1-6}$ alkenyl, alkenyl, optionally substituted $C_{1-6}$ alkynyl, optionally substituted $C_{3-8}$ cycloalkyl, or optionally substituted $C_{2-7}$ heterocycloalkyl, or $R^5$ and $R^{5'}$ taken together form an oxo, or $R^5$ and $R^{5'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —$NO_2$, oxo, —CN, $C_{1-3}$ alkoxyl, $C_{1-3}$ alkyl and $C_{1-3}$ haloalkyl;

each of $R^6$ and $R^{6'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{1-6}$ alkenyl, optionally substituted $C_{1-6}$ alkynyl, optionally substituted $C_{3-8}$ cycloalkyl, and optionally substituted $C_{2-7}$ heterocycloalkyl, or $R^6$ and $R^{6'}$ taken together form an oxo, or $R^6$ and $R^{6'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —$NO_2$, oxo, —CN, $C_{1-3}$ alkoxyl, $C_{1-3}$ alkyl and $C_{1-3}$ haloalkyl;

each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl, or $R^8$ and $R^9$ taken together with the carbon to which they are attached form an optionally substituted 3-6 membered cycloalkyl or heterocycloalkyl, wherein the alkyl, alkenyl, alkynyl, cycloalkyl or heterocycloalkyl is optionally substituted with one or more substituents independently selected from: halogen, amino, —OH, —$NO_2$, oxo, —CN, $C_{1-3}$ alkoxyl, $C_{1-3}$ alkyl and $C_{1-3}$ haloalkyl;

ring A is monocyclic heteroarylbicyclic heteroaryl, monocyclic heterocycloalkyl, or bicyclic heterocycloalkyl;

each of $R^4$ is independently selected from halogen, —$NO_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$, wherein the alkyl, alkenyl, alkynyl, heteroalkyl, cycloalkyl, or heterocycloalkyl is optionally substituted with one or more substituents independently selected from: halogen, —OH, —$NO_2$, oxo, amino, —CN, $C_{1-6}$ alkoxyl, $C_{1-6}$ alkyl, $C_{1-6}$ haloalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, amino, —$NO_2$, oxo, —CN, $C_{1-6}$ alkyl, $C_{1-6}$ alkoxy, and $C_{1-6}$ haloalkyl;

$R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl, wherein the alkyl, alkenyl, alkynyl, heteroalkyl, alkylene, cycloalkyl, heterocycloalkyl, phenyl, or heteroaryl is optionally substituted with one or more substituents independently selected from: halogen, —OH, amino, —$NO_2$, oxo, $C_{1-6}$ alkoxy, —CN, $C_{1-6}$ alkyl, and $C_{1-6}$ haloalkyl;

each of $R^{12}$ is independently selected from hydrogen, halogen, —OH, —$NO_2$, —CN, $C_{1-6}$ alkyl, $C_{1-6}$ aminoalkyl, $C_{1-6}$ hydroxyalkyl, $C_{1-6}$ haloalkyl, $C_{1-6}$ heteroalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, —CN, $C_{1-6}$ alkyl, $C_{1-6}$ alkoxy, and $C_{1-6}$haloalkyl;

$R^{B1}$ is optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, or optionally substituted bicyclic heteroaryl, wherein each of the cycloalkyl, heterocycloalkyl, naphthyl, phenyl or heteroaryl is optionally substituted with one or more substituents independently selected from: halogen, —$NO_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, and —$S(O)_2N(R^{12})(R^{11})$, wherein the alkyl, alkenyl, alkynyl, heteroalkyl, cycloalkyl, or heterocycloalkyl is optionally substituted with one or more substituents independently selected from: halogen, —OH, —$NO_2$, amino, —$NH(C_{1-6}$ alkyl), —$N(C_{1-6}$ alkyl)$_2$, oxo, —CN, $C_{1-3}$ alkoxyl, $C_{1-3}$ alkyl and $C_{1-3}$ haloalkyl;

each of $R^{Y1}$, $R^{Y2}$, $R^{Y3}$ and $R^{Y4}$ is independently selected from hydrogen, halo, —CN, —$NO_2$, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$, optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, and optionally substituted bicyclic heteroaryl, wherein the each of the alkyl, alkenyl, alkynyl, heteroalkyl, cycloalkyl, heterocycloalkyl, naphthyl, phenyl or heteroaryl is optionally substituted with one or more substituents independently selected from: halogen, —OH, —$NO_2$, amino, oxo, —CN, $C_{1-3}$ alkoxyl, $C_{1-3}$ alkyl and $C_{1-3}$ haloalkyl; or $R^{Y1}$ and $R^{Y2}$ are taken together with the carbons to which they are attached to form an optionally substituted $C_{3-8}$ cycloalkyl or optionally substituted $C_{2-9}$ heterocycloalkyl, wherein the cycloalkyl or heterocycloalkyl is optionally substituted with one or more substituents independently selected from: halogen, —OH, amino, —$NO_2$, oxo, $C_{1-6}$ alkoxy, —CN, $C_{1-6}$ alkyl, and $C_{1-6}$ haloalkyl; or $R^{Y3}$ and $R^{Y4}$ are taken together with the carbons to which they are attached to form an optionally substituted $C_{3-8}$ cycloalkyl or optionally substituted $C_{2-9}$ heterocycloalkyl, wherein the cycloalkyl or heterocycloalkyl is optionally substituted with one or more substituents independently selected from: halogen, —OH, amino, —$NO_2$, oxo, $C_{1-6}$ alkoxy, —CN, $C_{1-6}$ alkyl, and $C_{1-6}$ haloalkyl;

m is 0, 1, 2, 3, or 4; and p is 0 or 1.

In some embodiments of Formula (IVa), each of $R^4$ and $R^{4'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl, or $R^4$ and $R^{4'}$ taken together form an oxo, or $R^4$ and $R^{4'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —$NO_2$, oxo, —CN, $C_{1-3}$ alkoxyl, $C_{1-3}$ alkyl and $C_{1-3}$ haloalkyl.

In some embodiments of Formula (IVa), each of $R^5$ and $R^{5'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl, or $R^5$ and $R^{5'}$ taken together form an oxo, or $R^5$ and $R^{5'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —$NO_2$, oxo, —CN, $C_{1-3}$ alkoxyl, $C_{1-3}$ alkyl and $C_{1-3}$ haloalkyl.

In some embodiments of Formula (IVa), each of $R^6$ and $R^{6'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl, or $R^6$ and $R^{6'}$ taken together form an oxo, or $R^6$ and $R^{6'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —$NO_2$, oxo, —CN, $C_{1-3}$ alkoxyl, $C_{1-3}$ alkyl and $C_{1-3}$ haloalkyl.

In some embodiments, the compound of Formula (IVa), (IVa-1), and (IVa-2), $Y^1$ is N or $CR^{Y1}$;

$Y^2$ is N or $CR^{Y2}$;

$Y^3$ is N or $CR^{Y3}$;

$Y^4$ is N or $CR^{Y4}$;

each of $R^1$ is hydrogen, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl, optionally substituted $C_{3-8}$ cycloalkyl, or optionally substituted $C_{2-7}$ heterocycloalkyl;

wherein the alkyl, heteroalkyl, alkenyl, or alkynyl is optionally substituted with one or more substituents independently selected from: halogen, amino, oxo, —OH, —NO$_2$, —CN, and $C_{1-3}$ alkoxyl;

each of $R^4$ and $R^{4'}$ is independently selected from hydrogen, —CN, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl, or $R^4$ and $R^{4'}$ taken together form an oxo, or $R^4$ and $R^{4'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —NO$_2$, oxo, —CN, $C_{1-3}$ alkoxyl, $C_{1-3}$ alkyl and $C_{1-3}$ haloalkyl;

each of $R^5$ and $R^{5'}$ is independently selected from hydrogen, —CN, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl, or $R^5$ and $R^{5'}$ taken together form an oxo, or $R^5$ and $R^{5'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —NO$_2$, oxo, —CN, $C_{1-3}$ alkoxyl, $C_{1-3}$ alkyl and $C_{1-3}$ haloalkyl;

each of $R^6$ and $R^{6'}$ is independently selected from hydrogen, halo, —CN, —OR$^{11}$, —SR$^{11}$, —N(R$^{12}$)(R$^{11}$), optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl, or $R^6$ and $R^{6'}$ taken together form an oxo, or $R^6$ and $R^{6'}$ taken together with the carbon to which they are attached form a 3-6 membered cycloalkyl or 3-6 membered heterocycloalkyl, wherein the alkyl, alkenyl, alkynyl, cycloalkyl or heterocycloalkyl is optionally substituted with one or more substituents independently selected from: halogen, amino, —OH, —NO$_2$, oxo, —CN, $C_{1-3}$ alkoxyl, $C_{1-3}$ alkyl and $C_{1-3}$ haloalkyl;

each of $R^8$ and $R^9$ is independently selected from hydrogen, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl, or $R^8$ and $R^9$ taken together with the carbon to which they are attached form an optionally substituted 3-6 membered cycloalkyl or heterocycloalkyl, wherein the alkyl, alkenyl, alkynyl, cycloalkyl or heterocycloalkyl is optionally substituted with one or more substituents independently selected from: halogen, amino, —OH, —NO$_2$, oxo, —CN, $C_{1-3}$ alkoxyl, $C_{1-3}$ alkyl and $C_{1-3}$ haloalkyl;

ring A is monocyclic heteroaryl, bicyclic heteroaryl, monocyclic heterocycloalkyl, or bicyclic heterocycloalkyl;

each of $R^A$ is independently selected from halogen, —NO$_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —OR$^{11}$, —SR$^{11}$, —N(R$^{12}$)(R$^{11}$), —C(O)R$^{12}$, —C(O)OR$^{12}$, —OC(O)R$^{12}$, —OC(O)N(R$^{12}$)(R$^{11}$), —C(O)N(R$^{12}$)(R$^{11}$), —N(R$^{12}$)C(O)R$^{12}$, —N(R$^{12}$)C(O)OR$^{12}$, —N(R$^{12}$)C(O)N(R$^{12}$)(R$^{11}$), —N(R$^{12}$)$_2$S(O)$_2$(R$^{12}$), —S(O)R$^{12}$, —S(O)$_2$R$^{12}$, and —S(O)$_2$N(R$^{12}$)(R$^{11}$), wherein the alkyl, alkenyl, alkynyl, heteroalkyl, cycloalkyl, or heterocycloalkyl is optionally substituted with one or more substituents independently selected from: halogen, —OH, —NO$_2$, oxo, amino, —CN, $C_{1-6}$ alkoxyl, $C_{1-6}$ alkyl, $C_{1-6}$ haloalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, amino, —NO$_2$, oxo, —CN, $C_{1-6}$ alkyl, $C_{1-6}$ alkoxy, and $C_{1-6}$ haloalkyl;

$R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl, wherein the alkyl, alkenyl, alkynyl, heteroalkyl, alkylene, cycloalkyl, heterocycloalkyl, phenyl, or heteroaryl is optionally substituted with one or more substituents independently selected from: halogen, —OH, amino, —NO$_2$, oxo, $C_{1-6}$ alkoxy, —CN, $C_{1-6}$ alkyl, and $C_{1-6}$ haloalkyl;

each of $R^{12}$ is independently selected from hydrogen, —NO$_2$, —CN, $C_{1-6}$ alkyl, $C_{1-6}$ aminoalkyl, $C_{1-6}$ hydroxyalkyl, $C_{1-6}$ haloalkyl, $C_{1-6}$ heteroalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, oxo, amino, —NO$_2$, —CN, $C_{1-6}$ alkyl, $C_{1-6}$ alkoxy, and $C_{1-6}$ haloalkyl;

$R^{B1}$ is optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, or optionally substituted bicyclic heteroaryl, wherein each of the cycloalkyl, heterocycloalkyl, naphthyl, phenyl or heteroaryl is optionally substituted with one or more substituents independently selected from: halogen, —NO$_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —OR$^{11}$, —SR$^{11}$, —N(R$^{12}$)(R$^{11}$), —C(O)R$^{12}$, —C(O)OR$^{12}$, —OC(O)R$^{12}$, —OC(O)N(R$^{12}$)(R$^{11}$), —C(O)N(R$^{12}$)(R$^{11}$), —N(R$^{12}$)C(O)R$^{12}$, —N(R$^{12}$)C(O)OR$^{12}$, —N(R$^{12}$)C(O)N(R$^{12}$)(R$^{11}$), —N(R$^{12}$)S(O)$_2$(R$^{12}$), —S(O)R$^{12}$, —S(O)$_2$R$^{12}$, and —S(O)$_2$N(R$^{12}$)(R$^{11}$), wherein the alkyl, alkenyl, alkynyl, heteroalkyl, cycloalkyl, or heterocycloalkyl is optionally substituted with one or more substituents independently selected from: halogen, —OH, —$NO_2$, amino, —$NH(C_{1-6}$ alkyl), —$N(C_{1-6}$ alkyl$)_2$, oxo, —CN, $C_{1-3}$ alkoxyl, $C_{1-3}$ alkyl and $C_{1-3}$ haloalkyl;

each of $R^{Y1}$, $R^{Y2}$, $R^{Y3}$ and $R^{Y4}$ is independently selected from hydrogen, halo, —CN, —$NO_2$, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$, optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, and optionally substituted bicyclic heteroaryl, wherein the each of the alkyl, alkenyl, alkynyl, heteroalkyl, cycloalkyl, heterocycloalkyl, naphthyl, phenyl or heteroaryl is optionally substituted with one or more substituents independently selected from: halogen, —OH, —$NO_2$, amino, oxo, —CN, $C_{1-3}$ alkoxyl, $C_{1-3}$ alkyl and $C_{1-3}$ haloalkyl; or $R^{Y1}$ and $R^{Y2}$ are taken together with the carbons to which they are attached to form an optionally substituted $C_{3-8}$ cycloalkyl or optionally substituted $C_{2-9}$ heterocycloalkyl, wherein the cycloalkyl or heterocycloalkyl is optionally substituted with one or more substituents independently selected from: halogen, —OH, amino, —$NO_2$, oxo, $C_{1-6}$ alkoxy, —CN, $C_{1-6}$ alkyl, and $C_{1-6}$ haloalkyl; or $R^{Y3}$ and $R^{Y4}$ are taken together with the carbons to which they are attached to form an optionally substituted $C_{3-8}$ cycloalkyl or optionally substituted $C_{2-9}$ heterocycloalkyl, wherein the cycloalkyl or heterocycloalkyl is optionally substituted with one or more substituents independently selected from: halogen, —OH, amino, —$NO_2$, oxo, $C_{1-6}$ alkoxy, —CN, $C_{1-6}$ alkyl, and $C_{1-6}$ haloalkyl;

m is 0, 1, 2, 3, or 4; and p is 0 or 1.

In one aspect, the disclosure provides a compound represented by Formula (IVa), or a pharmaceutically acceptable salt or solvate thereof:

Formula (IVa)

wherein, $Y^1$ is N or $CR^{Y1}$;

$Y^2$ is N or $CR^{Y2}$;

$Y^3$ is N or $CR^{Y3}$;

$Y^4$ is N or $CR^{Y4}$;

$R^1$ is hydrogen, —CN, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, optionally substituted $C_{3-8}$ cycloalkyl, or optionally substituted $C_{2-7}$ heterocycloalkyl;

each of $R^4$ and $R^{4'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^4$ and $R^{4'}$ taken together form an oxo; or $R^4$ and $R^{4'}$ taken together with the carbon to which they are attached form a 3-6 membered cycloalkyl or 3-6 membered heterocycloalkyl;

each of $R^5$ and $R^{5'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^5$ and $R^{5'}$ taken together form an oxo; or $R^5$ and $R^{5'}$ taken together with the carbon to which they are attached form a 3-6 membered cycloalkyl or 3-6 membered heterocycloalkyl;

each of $R^6$ and $R^{6'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^6$ and $R^{6'}$ taken together form an oxo; or $R^6$ and $R^{6'}$ taken together with the carbon to which they are attached form a 3-6 membered cycloalkyl or 3-6 membered heterocycloalkyl;

each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl; or $R^8$ and $R^9$ taken together with the carbon to which they are attached form an optionally substituted 3-6 membered cycloalkyl or 3-6 membered heterocycloalkyl;

ring A is aryl, monocyclic heteroaryl, bicyclic heteroaryl, monocyclic heterocycloalkyl, or bicyclic heterocycloalkyl;

each of $R^A$ is independently selected from halogen, —$NO_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$;

$R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl;

each of $R^{12}$ is independently selected from hydrogen, —$NO_2$, —CN, $C_{1-6}$ alkyl, $C_{1-6}$ aminoalkyl, $C_{1-6}$ hydroxyalkyl, $C_{1-6}$ haloalkyl, $C_{1-6}$ heteroalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, —CN, $C_{1-6}$ alkyl, $C_{1-6}$ alkoxy, and $C_{1-6}$ haloalkyl;

$R^{B1}$ is optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, or optionally substituted bicyclic heteroaryl;

each of $R^{Y1}$, $R^{Y2}$, $R^{Y3}$ and $R^{Y4}$ is independently selected from hydrogen, halo, —CN, —$NO_2$, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$, optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, and optionally substituted bicyclic heteroaryl; or $R^{Y1}$ and $R^{Y2}$ are taken together with the carbons to which they are attached to form an optionally substituted $C_{3-8}$ cycloalkyl or optionally substituted $C_{2-9}$ heterocycloalkyl; or $R^{Y3}$ and $R^{Y4}$ are taken together with the carbons to which they are attached to form an optionally substituted $C_{3-8}$ cycloalkyl or optionally substituted $C_{2-9}$ heterocycloalkyl;

m is 0, 1, 2, 3, or 4; and p is 0 or 1.

In some embodiments of Formula (IVa), (IVa-1), and (IVa-2), ring A is aryl, monocyclic heteroaryl, bicyclic heteroaryl, monocyclic heterocycloalkyl, or bicyclic heterocycloalkyl, wherein when ring A is aryl, at least one of $Y^1$, $Y^2$, $Y^3$, and $Y^4$ is N; and $R^{B1}$ is optionally substituted monocyclic heteroaryl, or optionally substituted bicyclic heteroaryl.

In some embodiments of Formula (IVa), (IVa-1), and (IVa-2), ring A is aryl. In some embodiments, ring A is phenyl.

In some embodiments of Formula (IVa), (IVa-1), and (IVa-2),

In some embodiments

In some embodiments of Formulas (IVa), (IVa-1), and (IVa-2), ring A is unsubstituted aryl (e.g., phenyl). In some embodiments of Formulas (IVa), (IVa-1), and (IVa-2), ring A is aryl (e.g., phenyl) that is optionally substituted with 1 to 5 $R^A$. In some embodiments of Formulas (IVa), (IVa-1), and (IVa-2), ring A is aryl (e.g., phenyl) that is substituted with 1 $R^4$. In some embodiments of Formulas (IVa), (IVa-1), and (IVa-2), ring A is aryl (e.g., phenyl) that is substituted with 2 $R^4$. In some embodiments of Formulas (IVa), (IVa-1), and (IVa-2), ring A is aryl (e.g., phenyl) that is substituted with 3 $R^4$. In some embodiments of Formulas (IVa), (IVa-1), and (IVa-2), ring A is aryl (e.g., phenyl) that is substituted with 4 $R^4$. In some embodiments of Formulas (IVa), (IVa-1), and (IVa-2), ring A is aryl (e.g., phenyl) that is substituted with 5 $R^4$.

In some embodiments of Formulas (IVa), (IVa-1), and (IVa-2), at least one of $Y^1$, $Y^z$ $Y^3$ and $Y^4$ is N. In some embodiments, one of $Y^1$, $Y^2$, $Y^3$, and $Y^4$ is N. In some embodiments, two of $Y^1$, $Y^z$ $Y^3$ and $Y^4$ are N. In some embodiments, three of $Y^1$, $Y^2$, $Y^3$, and $Y^4$ are N. In some embodiments of Formulas (IVa), (IVa-1), and (IVa-2), $R^{B1}$ is optionally substituted monocyclic heteroaryl, or optionally substituted bicyclic heteroaryl. In some embodiments, $R^{B1}$ is optionally substituted monocyclic heteroaryl (e.g., 5 membered heteroaryl). In some embodiments, $R^{B1}$ is substituted monocyclic heteroaryl.

In some embodiments of Formulas (IVa), (IVa-1), and (IVa-2), each $R^4$ is independently selected from halogen, —$NO_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$. In some embodiments, $R^4$ is not $C_{1-6}$ alkoxyl. In some embodiments, $R^4$ is not $C_1$. In some embodiments, $R^4$ is not halogen.

In some embodiments, the compound of Formula (IVa) is represented by Formula (IVa-1), or a pharmaceutically acceptable salt or solvate thereof:

Formula (IVa-1)

In some embodiments, the compound of Formula (IVa) is represented by Formula (IVa-2), or a pharmaceutically acceptable salt or solvate thereof:

Formula (IVa-2)

In some embodiments of Formula (IVa), (IVa-1), and (IVa-2), each of $R^1$ is hydrogen, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl, optionally substituted $C_{3-8}$ cycloalkyl, or optionally substituted $C_{2-7}$ heterocycloalkyl.

In some embodiments of Formula (IVa) and (IVa-1), each of $R^4$ and $R^{4'}$ is independently selected from hydrogen, —CN, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^4$ and $R^{4'}$ taken together form an oxo; or $R^4$ and $R^{4'}$ taken together with the carbon to which they are attached form a 3-6 membered cycloalkyl or 3-6 membered heterocycloalkyl.

In some embodiments of Formula (IVa) and (IVa-1), each of $R^5$ and $R^{5'}$ is independently selected from hydrogen, —CN, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^5$ and $R^{5'}$ taken together form an oxo; or $R^5$ and $R^{5'}$ taken together with the carbon to which they are attached form a 3-6 membered cycloalkyl or 3-6 membered heterocycloalkyl.

In some embodiments of Formula (IVa) and (IVa-1), each of $R^6$ and $R^{6'}$ is independently selected from hydrogen, —CN, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl; or $R^6$ and $R^{6'}$ taken together form an oxo; or $R^6$ and $R^{6'}$ taken together with the carbon to which they are attached form a 3-6 membered cycloalkyl or 3-6 membered heterocycloalkyl.

In some embodiments of Formula (IVa), each of $R^8$ and $R^9$ is independently selected from hydrogen, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl; or $R^8$ and $R^9$ taken together with the carbon to which they are attached form an optionally substituted 3-6 membered cycloalkyl or heterocycloalkyl.

In some embodiments of Formula (IVa), (IVa-1), and (IVa-2), each of $R^{12}$ is independently selected from hydrogen, —$NO_2$, CN, $C_{1-6}$ alkyl, $C_{1-6}$ aminoalkyl, $C_{1-6}$ hydroxyalkyl, $C_{1-6}$ haloalkyl, $C_{1-6}$ heteroalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, CN, $C_{1-6}$ alkyl, $C_{1-6}$ alkoxy, and $C_{1-6}$ haloalkyl.

In some embodiments of Formula (IVa), (IVa-1), and (IVa-2), ring A is 3-6 membered monocyclic heterocycloalkyl containing 1-4 heteroatoms selected from O, S, N, P, and Si. In some embodiments, ring A is fused, spiro, or bridged bicyclic heterocycloalkyl containing 1-4 heteroatoms selected from O, S, N, P, and Si. In some embodiments, ring A is a 5 membered monocyclic heteroaryl. In some embodiments, ring A is a 6 membered monocyclic heteroaryl. In some embodiments, ring A is a 6 membered monocyclic heteroaryl containing 1-3 heteroatoms. In some embodiments, ring A is pyridine, pyrimidine, pyrazine, pyridazine, triazine, imidazole, pyrazole, triazole, oxazole, isoxazole, or thiophene. In some embodiments, In some embodiments, In some embodiments, In some embodiments, In some embodiments, In some embodiments, In some embodiments, In some embodiments, In some embodiments, In some embodiments, In some embodiments, In some embodiments, In some embodiments, In some embodiments, In some embodiments, In some embodiments, ring A is bicyclic heteroaryl. In some embodiments, ring A is fused 5-6, 6-6, or 6-5 bicyclic heteroaryl.

In some embodiments of Formula (IVa), (IVa-1), and (IVa-2), each $R^A$ is independently selected from halogen, $-NO_2$, oxo, $-CN$, optionally substituted $C_{1-6}$ alkyl, optionally substituted $C_{1-6}$ heteroalkyl, optionally substituted $C_{3-8}$ cycloalkyl, optionally substituted $C_{2-7}$ heterocycloalkyl, $-OR^{11}$, $-SR^{11}$, $-N(R^{12})(R^{11})$, $-C(O)R^{12}$, $-C(O)OR^{12}$, $-OC(O)R^{12}$, $-OC(O)N(R^{12})(R^{11})$, $-C(O)N(R^{12})(R^{11})$, $-N(R^{12})C(O)R^{12}$, $-N(R^{12})C(O)OR^{12}$, $-N(R^{12})C(O)N(R^{12})(R^{11})$, $-N(R^{12})_2S(O)_2(R^{12})$, $-S(O)R^{12}$, $-S(O)_2R^{12}$, and $-S(O)_2N(R^{12})(R^{11})$. In some embodiments of Formula (IVa), (IVa-1), and (IVa-2), each $R^A$ is independently selected from halogen, OH, $-NO_2$, oxo, $-CN$, $C_{1-6}$ alkyl, $C_{1-6}$ alkoxy, $C_{1-6}$ haloalkyl, $C_{1-6}$ heteroalkyl, and $C_{3-6}$ cycloalkyl. In some embodiments, each $R^A$ is independently selected from halogen, $C_{1-6}$ alkyl, $C_{1-6}$ alkoxyl, $C_{1-6}$ haloalkyl, and $C_{3-6}$ cycloalkyl. In some embodiments, each $R^A$ is independently selected from $C_{1-6}$ alkyl, $C_{1-6}$ alkoxyl, $C_{1-6}$ haloalkoxyl, $C_{1-6}$ haloalkyl, and $C_{3-6}$ cycloalkyl. In some embodiments, each $R^A$ is independently selected from halogen, $C_{1-6}$ alkyl, $C_{1-6}$ alkoxyl, and $C_{3-6}$ cycloalkyl, wherein the alkyl, alkoxyl and cycloalkyl is optionally substituted with one or more halogen (e.g., 1-3 fluorine). In some embodiments, each $R^A$ is independently selected from methyl, ethyl, propyl, butyl, —O-methyl, —O-ethyl, —O-propyl, —O-butyl, cyclopropyl, CN, OH, —O—$CHF_2$, —O—$CH_2F$, $CHF_2$, $CH_2F$, and $CF_3$. In some embodiments, $R^A$ is halogen. In some embodiments, $R^A$ is —$NO_2$. In some embodiments, $R^A$ is oxo. In some embodiments, $R^A$ is —CN. In some embodiments, $R^A$ is optionally substituted $C_{1-6}$ alkyl. In some embodiments, $R^A$ is $C_{1-6}$ alkyl. In some embodiments, $R^A$ is $C_2$ alkyl. In some embodiments, $R^A$ is $C_3$ alkyl. In some embodiments, $R^A$ is optionally substituted $C_{1-6}$ heteroalkyl. In some embodiments, $R^A$ is $C_3$ heteroalkyl. In some embodiments, $R^A$ is optionally substituted $C_{3-8}$ cycloalkyl. In some embodiments, $R^A$ is $C_3$ cycloalkyl. In some embodiments, $R^A$ is optionally substituted $C_{2-7}$ heterocycloalkyl. In some embodiments, $R^A$ is $C_2$ heterocycloalkyl. In some embodiments, $R^A$ is —$OR^{11}$. In some embodiments, $R^A$ is —$SR^{11}$. In some embodiments, $R^A$ is —$N(R^{12})(R^{11})$. In some embodiments, $R^A$ is —$C(O)R^{12}$. In some embodiments, $R^A$ is —$C(O)OR^{12}$. In some embodiments, $R^A$ is —$OC(O)R^{12}$. In some embodiments, $R^A$ is —$OC(O)N(R^{12})(R^{11})$. In some embodiments, $R^A$ is —$C(O)N(R^{12})(R^{11})$ In some embodiments, $R^A$ is —$N(R^{12})C(O)R^{12}$, —$N(R^{12})C(O)OR^{12}$. In some embodiments, $R^A$ is —$N(R^{12})C(O)N(R^{12})(R^{11})$. In some embodiments, $R^A$ is —$N(R^{12})_2S(O)_2(R^{12})$. In some embodiments, $R^A$ is —$S(O)R^{12}$. In some embodiments, $R^A$ is —$S(O)_2R^{12}$. In some embodiments, $R^A$ is —$S(O)_2N(R^{12})(R^{11})$.

In some embodiments of Formula (IVa), (IVa-1), and (IVa-2), $R^A$ is independently substituted with one or more substituents independently selected from: halogen, —OH, —$NO_2$, amino, —CN, $C_{1-6}$ alkoxyl, $C_{1-6}$ alkyl, $C_{1-6}$ haloalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, amino, —$NO_2$, oxo, —CN, $C_{1-6}$ alkyl, $C_{1-6}$ alkoxy, and $C_{1-6}$ haloalkyl.

In some embodiments of Formula (IVa), (IVa-1), and (IVa-2), is selected from:

37

-continued

38

-continued

In some embodiments.

In some embodiments,

In some embodiments, $\left(R^A\right)_m$—A is

In some embodiments, $\left(R^A\right)_m$—A is

In some embodiments, $\left(R^A\right)_m$—A is

In some embodiments, $\left(R^A\right)_m$—A is

In some embodiments, $\left(R^A\right)_m$—A is

In some embodiments, $\left(R^A\right)_m$—A is

In some embodiments, $\left(R^A\right)_m$—A is

In some embodiments, $\left(R^A\right)_m$—A is

In some embodiments of Formula (IVa), (IVa-1), and (IVa-2), p is 1. In some embodiments, p is 0.

In some embodiments of Formula (IVa), (IVa-1), and (IVa-2), each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl. In some embodiments of Formula (IVa), (IVa-1), and (IVa-2), each of $R^8$ and $R^9$ is independently selected from hydrogen, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl. In some embodiments. In some embodiments, $R^8$ and $R^9$ taken together with the carbon to which they are attached form an optionally substituted 3-6 membered cycloalkyl or heterocycloalkyl.

In some embodiments of Formula (IVa), (IVa-1), and (IVa-2), $R^{B1}$ is optionally substituted $C_{3-8}$ cycloalkyl or optionally substituted phenyl. In some embodiments, $R^{B1}$ is optionally substituted $C_{2-9}$ heterocycloalkyl, optionally substituted monocyclic heteroaryl, or optionally substituted bicyclic heteroaryl, each of which containing 1-4 heteroatoms selected from O, S, N, P, and Si. In some embodiments, $R^{B1}$ is optionally substituted $C_{3-8}$ cycloalkyl. In some embodiments, $R^{B1}$ is $C_3$ cycloalkyl. In some embodiments, $R^{B1}$ is $C_5$ cycloalkyl. In some embodiments, $R^{B1}$ is $C_6$ cycloalkyl. In some embodiments, $R^{B1}$ is optionally substituted phenyl. In some embodiments, $R^{B1}$ is optionally substituted $C_{2-9}$ heterocycloalkyl. In some embodiments, $R^{B1}$ is $C_3$ heterocycloalkyl. In some embodiments, $R^{B1}$ is $C_5$ heterocycloalkyl. In some embodiments, $R^{B1}$ is $C_6$ heterocycloalkyl. In some embodiments, $R^{B1}$ is optionally substituted monocyclic heteroaryl. In some embodiments, $R^{B1}$ is optionally substituted bicyclic heteroaryl. In some embodiments, $R^{B1}$ is imidazole, pyrazole, triazole, or tetrazole, each of which optionally substituted. In some embodiments, $R^{B1}$ is imidazole. In some embodiments, $R^{B1}$ is pyrazole. In some embodiments, $R^{B1}$ is triazole. In some embodiments, $R^{B1}$ is tetrazole. In some embodiments, $R^{B1}$ is optionally substituted fused 5-6, 6-6 or 6-5 heteroaryl. In some embodiments, $R^{B1}$ is optionally substituted with one or more substituents independently selected from halogen, $-NO_2$, oxo, $-CN$, optionally substituted $C_{1-6}$ alkyl, optionally substituted $C_{1-6}$ heteroalkyl, optionally substituted $C_{3-8}$ cycloalkyl, optionally substituted $C_{2-7}$ heterocycloalkyl, $-OR^{11}$, $-SR^{11}$, $-N(R^{12})(R^{11})$, $-C(O)R^{12}$, $-C(O)OR^{12}$, $-OC(O)R^{12}$, $-OC(O)N(R^{12})(R^{11})$, $-C(O)N(R^{12})(R^{11})$, $-N(R^{12})C(O)$ $R^{12}$, $-N(R^{12})C(O)OR^{12}$, $-N(R^{12})C(O)N(R^{12})(R^{11})$, $-N(R^{12})S(O)_2(R^{12})$, $-S(O)R^{12}$, $-S(O)_2R^{12}$, and $-S(O)_2N(R^{12})(R^{11})$, wherein the alkyl, alkenyl, alkynyl, heteroalkyl, cycloalkyl, or heterocycloalkyl is optionally substituted with one or more substituents independently selected from: halogen, $-OH$, $-NO_2$, amino, oxo, $-CN$, $C_{1-3}$ alkoxyl, $C_{1-3}$ alkyl and $C_{1-3}$ haloalkyl. In some embodiments, $R^{B1}$ is optionally substituted with one or more substituents independently selected from halogen, $-OR^{11}$, $-NO_2$, oxo, $-CN$, optionally substituted $C_{1-6}$ haloalkyl, optionally substituted $C_{1-6}$ alkyl, optionally substituted $C_{1-6}$ aminoalkyl, optionally substituted $C_{1-6}$ hydroxyalkyl, optionally substituted $C_{1-6}$ heteroalkyl, optionally substituted $C_{3-8}$ cycloalkyl, and optionally substituted $C_{2-7}$ heterocycloalkyl. In some embodiments, $R^{B1}$ is optionally substituted with one or more substituents independently selected from halogen, $-OR^{11}$, $-NO_2$, oxo, $-CN$, $C_{1-3}$ haloalkyl, $C_{1-3}$ alkyl, $C_{1-3}$ aminoalkyl, $C_{1-3}$ hydroxyalkyl, optionally substituted $C_{1-4}$ heteroalkyl (e.g., $-CH_2C(=O)$ $N(CH_3)_2$), optionally substituted $C_{3-6}$ cycloalkyl, and optionally substituted $C_{2-5}$ heterocycloalkyl. In some embodiments, $R^{B1}$ is optionally substituted with one or more substituents independently selected from halogen, oxo, $-CN$, $C_{1-3}$ haloalkyl, $C_{1-3}$ alkyl, $C_{1-3}$ aminoalkyl, $C_{1-3}$ hydroxyalkyl, $C_{3-6}$ cycloalkyl, and $C_{2-5}$ heterocycloalkyl. In some embodiments, $^{RB1}$ is optionally substituted with one or more substituents (e.g., 1, 2 or 3) independently selected from $C_{1-3}$ haloalkyl and $C_{1-3}$ alkyl. In some embodiments, $R^{B1}$ is substituted with halogen. In some embodiments, $R^{B1}$ is substituted with $-OR^{11}$. In some embodiments, $R^{B1}$ is substituted with $-NO_2$. In some embodiments, $R^{B1}$ is substituted with oxo. In some embodiments, $R^{B1}$ is substituted with $-CN$. In some embodiments, $R^{B1}$ is substituted with optionally substituted $C_{1-6}$ haloalkyl. In some embodiments, $R^{B1}$ is substituted with optionally substituted $C_{1-6}$ alkyl. In some embodiments, $R^{B1}$ is substituted with optionally substituted $C_{1-6}$ aminoalkyl.

In some embodiments of Formula (IVa), (IVa-1), and (IVa-2), $R^{B1}$ is

-continued

43

-continued

44

-continued

In some embodiments of Formula (IVa), (IVa-1), and (IVa-2), $R^{B1}$ is

, ,

, or

.

In some embodiments, $R^{B1}$ is

.

In some embodiments, $R^{B1}$ is

.

In some embodiments, $R^{B1}$ is

.

In some embodiments, $R^{B1}$ is

In some embodiments, $R^{B1}$ is

In some embodiments of a compound of Formula (IVa), (IVa-1), and (IVa-2), $Y^1$ is N or $CR^{Y1}$. In some embodiments, $Y^1$ is N. In some embodiments, $Y^1$ is $CR^{Y1}$. In some embodiments, $Y^2$ is N. In some embodiments, $Y^2$ is $CR^{Y2}$. In some embodiments, $Y^3$ is N. In some embodiments, $Y^3$ is $CR^{Y3}$. In some embodiments, $Y^4$ is N. In some embodiments, $Y^4$ is $CR^{Y4}$.

In some embodiments of a compound of Formula (IVa), (IVa-1), and (IVa-2), $R^1$ is hydrogen, halo, —CN, —OR$^{11}$, —SR$^{11}$, —N(R$^{12}$)$_2$, optionally substituted C$_{1-6}$ alkyl, optionally substituted C$_{1-6}$ heteroalkyl, optionally substituted C$_{2-6}$ alkenyl, and optionally substituted C$_{2-6}$ alkynyl. In some embodiments of a compound of Formula (IVa), (IVa-1), and (IVa-2), $R^1$ is hydrogen, —CN, optionally substituted C$_{1-6}$ alkyl, optionally substituted C$_{1-6}$ heteroalkyl, optionally substituted C$_{2-6}$ alkenyl, and optionally substituted C$_{2-6}$ alkynyl. In some embodiments, $R^1$ is hydrogen. In some embodiments, $R^1$ is halo. In some embodiments, $R^1$ is —CN. In some embodiments, $R^1$ is —OR$^{11}$. In some embodiments, $R^1$ is —SR$^{11}$. In some embodiments, $R^1$ is —N(R$^{12}$)$_2$. In some embodiments, $R^1$ is optionally substituted C$_{1-6}$ alkyl. In some embodiments, $R^1$ is C$_{1-3}$ alkyl. In some embodiments, $R^1$ is methyl. In some embodiments, $R^1$ is ethyl. In some embodiments, $R^1$ is CD$_3$. In some embodiments, $R^1$ is optionally substituted C$_{1-6}$ heteroalkyl. In some embodiments, $R^1$ is C$_{1-3}$ heteroalkyl. In some embodiments, $R^1$ is optionally substituted C$_{2-6}$ alkenyl. In some embodiments, $R^1$ is C$_{2-3}$ alkenyl. In some embodiments, $R^1$ is optionally substituted C$_{2-6}$ alkynyl.

In some embodiments of a compound of Formula (IVa), (IVa-1), and (IVa-2), $R^1$ is hydrogen, halo, —CN, —OR$^{11}$, —SR$^{11}$, —N(R$^{12}$)(R$^{11}$), optionally substituted C$_{1-6}$ alkyl, optionally substituted C$_{1-6}$ heteroalkyl, optionally substituted C$_{2-6}$ alkenyl, optionally substituted C$_{2-6}$ alkynyl, optionally substituted C$_{3-8}$ cycloalkyl, or optionally substituted C$_{2-7}$ heterocycloalkyl. In some embodiments of a compound of Formula (IVa), (IVa-1), and (IVa-2), $R^1$ is hydrogen, —CN, optionally substituted C$_{1-6}$ alkyl, optionally substituted C$_{1-6}$ heteroalkyl, optionally substituted C$_{2-6}$ alkenyl, optionally substituted C$_{2-6}$ alkynyl, optionally substituted C$_{3-8}$ cycloalkyl, or optionally substituted C$_{2-7}$ heterocycloalkyl. In some embodiments, $R^1$ is hydrogen. In some embodiments, $R^1$ is halo. In some embodiments, $R^1$ is —CN. In some embodiments, $R^1$ is —OR$^{11}$. In some embodiments, $R^1$ is —SR$^{11}$. In some embodiments, $R^1$ is —N(R$^{12}$)(R$^{11}$). In some embodiments, $R^1$ is optionally substituted C$_{1-6}$ alkyl. In some embodiments, $R^1$ is optionally substituted C$_{1-6}$ heteroalkyl. In some embodiments, $R^1$ is optionally substituted C$_{2-6}$ alkenyl. In some embodiments, $R^1$ is optionally substituted C$_{2-6}$ alkynyl. In some embodiments, $R^1$ is optionally substituted C$_{3-8}$ cycloalkyl. In some embodiments, $R^1$ is optionally substituted C$_{2-7}$ heterocycloalkyl.

In some embodiments of a compound of Formula (IVa) or (IVa-1), each of $R^4$ and $R^{4'}$ is independently selected from hydrogen, halo, —CN, —OR$^{11}$, —SR$^{11}$, —N(R$^{12}$)(R$^{11}$), optionally substituted C$_{1-6}$ alkyl, optionally substituted C$_{2-6}$ alkenyl, optionally substituted C$_{2-6}$ alkynyl, optionally substituted C$_{3-8}$ cycloalkyl, and optionally substituted C$_{2-7}$ heterocycloalkyl; or $R^4$ and $R^{4'}$ taken together form an oxo; or $R^4$ and $R^{4'}$ taken together with the carbon to which they are attached form a 3-6 membered cycloalkyl or 3-6 membered heterocycloalkyl. In some embodiments of a compound of Formula (IVa) or (IVa-1), each of $R^4$ and $R^{4'}$ is independently selected from hydrogen, —CN, optionally substituted C$_{1-6}$ alkyl, optionally substituted C$_{2-6}$ alkenyl, optionally substituted C$_{2-6}$ alkynyl, optionally substituted C$_{3-8}$ cycloalkyl, and optionally substituted C$_{2-7}$ heterocycloalkyl; or $R^4$ and $R^{4'}$ taken together form an oxo; or $R^4$ and $R^{4'}$ taken together with the carbon to which they are attached form a 3-6 membered cycloalkyl or 3-6 membered heterocycloalkyl. In some embodiments, $R^4$ is hydrogen. In some embodiments, $R^4$ is halo. In some embodiments, $R^4$ is —CN. In some embodiments, $R^4$ is —OR$^{11}$. In some embodiments, $R^4$ is —SR$^{11}$. In some embodiments, $R^4$ is —N(R$^{12}$)(R$^{11}$). In some embodiments, $R^4$ is optionally substituted C$_{1-6}$ alkyl. In some embodiments, $R^4$ is optionally substituted C$_{1-6}$ alkenyl. In some embodiments, $R^4$ is optionally substituted C$_{2-6}$ alkenyl. In some embodiments, $R^4$ is optionally substituted C$_{1-6}$ alkynyl. In some embodiments, $R^4$ is optionally substituted C$_{2-6}$ alkynyl. In some embodiments, $R^4$ is optionally substituted C$_{3-8}$ cycloalkyl. In some embodiments, $R^4$ is optionally substituted C$_{2-7}$ heterocycloalkyl. In some embodiments, $R^{4'}$ is hydrogen. In some embodiments, $R^{4'}$ is halo. In some embodiments, $R^{4'}$ is —CN. In some embodiments, $R^{4'}$ is —OR$^{11}$. In some embodiments, $R^{4'}$ is —SR$^{11}$. In some embodiments, $R^{4'}$ is —N(R$^{12}$)(R$^{11}$). In some embodiments, $R^{4'}$ is optionally substituted C$_{1-6}$ alkyl. In some embodiments, $R^{4'}$ is optionally substituted C$_{1-6}$ alkenyl. In some embodiments, $R^{4'}$ is optionally substituted C$_{1-6}$ alkynyl. In some embodiments, $R^{4'}$ is optionally substituted C$_{2-6}$ alkenyl. In some embodiments, $R^{4'}$ is optionally substituted C$_{2-6}$ alkynyl. In some embodiments, $R^{4'}$ is optionally substituted C$_{3-8}$ cycloalkyl. In some embodiments, $R^{4'}$ is and optionally substituted C$_{2-7}$ heterocycloalkyl. In some embodiments, $R^4$ and $R^{4'}$ taken together form an oxo. In some embodiments, $R^4$ and $R^{4'}$ taken together with the carbon to which they are attached form a 3-6 membered cycloalkyl or 3-6 membered heterocycloalkyl.

In some embodiments of a compound of Formula (IVa) or (IVa-1)), each of $R^5$ and $R^{5'}$ is independently selected from hydrogen, halo, —CN, —OR$^{11}$, —SR$^{11}$, —N(R$^{12}$)(R$^{11}$), optionally substituted C$_{1-6}$ alkyl, optionally substituted C$_{2-6}$ alkenyl, optionally substituted C$_{2-6}$ alkynyl, optionally substituted C$_{3-8}$ cycloalkyl, and optionally substituted C$_{2-7}$ heterocycloalkyl. In some embodiments of a compound of Formula (IVa) or (IVa-1)), each of $R^5$ and $R^{5'}$ is independently selected from hydrogen, —CN, optionally substituted C$_{1-6}$ alkyl, optionally substituted C$_{2-6}$ alkenyl, optionally substituted C$_{2-6}$ alkynyl, optionally substituted C$_{3-8}$ cycloalkyl, and optionally substituted C$_{2-7}$ heterocycloalkyl. In some embodiments, $R^5$ is hydrogen. In some embodiments, $R^5$ is halo. In some embodiments, $R^5$ is —CN. In some embodiments, $R^5$ is —OR$^{11}$. In some embodiments, $R^5$ is —$SR^{11}$. In some embodiments, $R^5$ is —$N(R^{12})(R^{11})$. In some embodiments, $R^5$ is optionally substituted $C_{1-6}$ alkyl. In some embodiments, $R^5$ is optionally substituted $C_{1-6}$ alkenyl. In some embodiments, $R^5$ is optionally substituted $C_{1-6}$ alkynyl. In some embodiments, $R^5$ is optionally substituted $C_{2-6}$ alkenyl. In some embodiments, $R^5$ is optionally substituted $C_{2-6}$ alkynyl. In some embodiments, $R^5$ is optionally substituted $C_{3-8}$ cycloalkyl. In some embodiments, $R^5$ is optionally substituted $C_{2-7}$ heterocycloalkyl. In some embodiments, $R^{5'}$ is hydrogen. In some embodiments, $R^{5'}$ is halo. In some embodiments, $R^{5'}$ is —CN. In some embodiments, $R^{5'}$ is —$OR^{11}$. In some embodiments, $R^{5'}$ is —$SR^{11}$. In some embodiments, $R^{5'}$ is —$N(R^{12})(R^{11})$. In some embodiments, $R^{5'}$ is optionally substituted $C_{1-6}$ alkyl. In some embodiments, $R^{5'}$ is optionally substituted $C_{1-6}$ alkenyl. In some embodiments, $R^{5'}$ is optionally substituted $C_{1-6}$ alkynyl. In some embodiments, $R^{5'}$ is optionally substituted $C_{2-6}$ alkenyl. In some embodiments, $R^{5'}$ is optionally substituted $C_{2-6}$ alkynyl. In some embodiments, $R^{5'}$ is optionally substituted $C_{3-8}$ cycloalkyl. In some embodiments, $R^{5'}$ is and optionally substituted $C_{2-7}$ heterocycloalkyl. In some embodiments, $R^5$ and $R^{5'}$ taken together form an oxo. In some embodiments, $R^5$ and $R^{5'}$ taken together with the carbon to which they are attached form a 3-6 membered cycloalkyl or 3-6 membered heterocycloalkyl.

In some embodiments of a compound of Formula (IVa) or (IVa-1), each of $R^6$ and $R^{6'}$ is independently selected from hydrogen, halo, —CN, —$OR^{11}$, —$SR^{11}$, —$N(R^{12})(R^{11})$, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl. In some embodiments of a compound of Formula (IVa) or (IVa-1)), each of $R^6$ and $R^{6'}$ is independently selected from hydrogen, —CN, optionally substituted $C_{1-6}$ alkyl, optionally substituted $C_{2-6}$ alkenyl, optionally substituted $C_{2-6}$ alkynyl, optionally substituted $C_{3-8}$ cycloalkyl, and optionally substituted $C_{2-7}$ heterocycloalkyl. In some embodiments, $R^6$ is hydrogen. In some embodiments, $R^6$ is halo. In some embodiments, $R^6$ is —CN. In some embodiments, $R^6$ is —$OR^{11}$. In some embodiments, $R^6$ is —$SR^{11}$. In some embodiments, $R^6$ is —$N(R^{12})(R^{11})$. In some embodiments, $R^6$ is optionally substituted $C_{1-6}$ alkyl. In some embodiments, $R^6$ is optionally substituted $C_{1-6}$ alkenyl. In some embodiments, $R^6$ is optionally substituted $C_{1-6}$ alkynyl. In some embodiments, $R^6$ is optionally substituted $C_{2-6}$ alkenyl. In some embodiments, $R^6$ is optionally substituted $C_{2-6}$ alkynyl. In some embodiments, $R^6$ is optionally substituted $C_{3-8}$ cycloalkyl. In some embodiments, $R^6$ is optionally substituted $C_{2-7}$ heterocycloalkyl. In some embodiments, $R^{6'}$ is hydrogen. In some embodiments, $R^{6'}$ is halo. In some embodiments, $R^{6'}$ is —CN. In some embodiments, $R^{6'}$ is —$OR^{11}$. In some embodiments, $R^{6'}$ is —$SR^{11}$. In some embodiments, $R^{6'}$ is —$N(R^{12})(R^{11})$. In some embodiments, $R^{6'}$ is optionally substituted $C_{1-6}$ alkyl. In some embodiments, $R^{6'}$ is optionally substituted $C_{1-6}$ alkenyl. In some embodiments, $R^{6'}$ is optionally substituted $C_{1-6}$ alkynyl. In some embodiments, $R^{6'}$ is optionally substituted $C_{2-6}$ alkenyl. In some embodiments, $R^{6'}$ is optionally substituted $C_{2-6}$ alkynyl. In some embodiments, $R^{6'}$ is optionally substituted $C_{3-8}$ cycloalkyl. In some embodiments, $R^{6'}$ is and optionally substituted $C_{2-7}$ heterocycloalkyl. In some embodiments, $R^6$ and $R^{6'}$ taken together form an oxo. In some embodiments, $R^6$ and $R^{6'}$ taken together with the carbon to which they are attached form a 3-6 membered cycloalkyl or 3-6 membered heterocycloalkyl.

In some embodiments of a compound of Formula (IVa), (IVa-1), and (IVa-2), each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl. In some embodiments of a compound of Formula (IVa), (IVa-1), and (IVa-2), each of $R^8$ and $R^9$ is independently selected from hydrogen, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl. In some embodiments, $R^8$ is hydrogen. In some embodiments, $R^8$ is halo. In some embodiments, $R^8$ is —CN. In some embodiments, $R^8$ is optionally substituted $C_{1-6}$ alkyl. In some embodiments, $R^8$ is optionally substituted $C_{1-6}$ heteroalkyl. In some embodiments, $R^8$ is optionally substituted $C_{2-6}$ alkenyl. In some embodiments, $R^8$ is optionally substituted $C_{2-6}$ alkynyl. In some embodiments, $R^9$ is hydrogen. In some embodiments, $R^9$ is halo. In some embodiments, $R^9$ is —CN. In some embodiments, $R^9$ is optionally substituted $C_{1-6}$ alkyl. In some embodiments, $R^9$ is optionally substituted $C_{1-6}$ heteroalkyl. In some embodiments, $R^9$ is optionally substituted $C_{2-6}$ alkenyl. In some embodiments, $R^9$ is optionally substituted $C_{2-6}$ alkynyl. In some embodiments, $R^8$ and $R^9$ taken together with the carbon to which they are attached form an optionally substituted 3-6 membered cycloalkyl or heterocycloalkyl.

In some embodiments of a compound of Formula (IVa), (IVa-1), and (IVa-2), ring A is monocyclic heteroaryl, bicyclic heteroaryl, monocyclic heterocycloalkyl, or bicyclic heterocycloalkyl. In some embodiments, ring A is monocyclic heteroaryl. In some embodiments, ring A is bicyclic heteroaryl. In some embodiments, ring A is monocyclic heterocycloalkyl. In some embodiments, ring A is bicyclic heterocycloalkyl.

In some embodiments of a compound of Formula (IVa), (IVa-1), and (IVa-2), each of $R^A$ is independently selected from halogen, —$NO_2$, oxo, CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, $C(O)OR^{12}$, —$OC(O)R^{12}$, —$OC(O)N(R^{12})$ $(R^{11})$, —$C(O)N(R^{12})(R^{11})$, —$N(R^{12})C(O)R^{12}$, —$N(R^{12})C$ $(O)OR^{12}$, —$N(R^{12})C(O)N(R^{12})(R^{11})$, —$N(R^{12})_2S(O)_2$ $(R^{12})$, —$S(O)R^{12}$, —$S(O)_2R^{12}$, and —$S(O)_2N(R^{12})(R^{11})$. In some embodiments, $R^A$ is halogen. In some embodiments, $R^A$ is —$NO_2$. In some embodiments, $R^A$ is oxo. In some embodiments, $R^A$ is CN. In some embodiments, $R^A$ is optionally substituted $C_{1-6}$ alkyl. In some embodiments, $R^A$ is optionally substituted $C_{1-3}$ alkyl. In some embodiments, $R^A$ is methyl, ethyl, propyl, iso-propyl, n-butyl, iso-butyl, sec-butyl, t-butyl, —$CF_3$, —$CH_2CF_3$, or —$CH_2CH_2F$. In some embodiments, $R^A$ is optionally substituted $C_{2-6}$ alkenyl. In some embodiments, $R^A$ is optionally substituted $C_{2-6}$ alkynyl. In some embodiments, $R^A$ is optionally substituted $C_{1-6}$ heteroalkyl. In some embodiments, $R^A$ is optionally substituted $C_{3-8}$ cycloalkyl. In some embodiments, $R^A$ is optionally substituted $C_{3-6}$ cycloalkyl, e.g., cyclopropyl. In some embodiments, $R^A$ is , , , or -continued In some embodiments, $R^A$ is optionally substituted $C_{2-7}$ heterocycloalkyl. In some embodiments, $R^A$ is optionally substituted $C_{2-5}$ heterocycloalkyl. In some embodiments, $R^A$ is —$OR^{11}$. In some embodiments, $R^A$ is —O—$C_{1-3}$ alkyl. In some embodiments, $R^A$ is —$OCH_3$, —$OCH_2CH_3$, —$OCH_2OMe$, —$OCH_2CH_2OH$, —$OC(CH_3)_3$, or —$OCH_2CH_2OCH_3$. In some embodiments, $R^A$ is —$OCH_3$. In some embodiments, $R^A$ is In some embodiments, $R^A$ is —$SR^{11}$. In some embodiments, $R^A$ is —$N(R^{12})(R^{11})$. In some embodiments, $R^A$ is —$C(O)R^{12}$. In some embodiments, $R^A$ is $C(O)OR^{12}$. In some embodiments, $R^A$ is —$OC(O)R^{12}$. In some embodiments, $R^A$ is —$OC(O)N(R^{12})(R^{11})$. In some embodiments, $R^A$ is —$C(O)N(R^{12})(R^{11})$. In some embodiments, $R^A$ is —$N(R^{12})C(O)R^{12}$. In some embodiments, $R^A$ is —$N(R^{12})C(O)OR^{12}$. In some embodiments, $R^A$ is —$N(R^{12})C(O)N(R^{12})(R^{11})$. In some embodiments, $R^A$ is —$N(R^{12})_2S(O)_2(R^{12})$. In some embodiments, $R^A$ is —$S(O)R^{12}$. In some embodiments, $R^A$ is —$S(O)_2R^{12}$. In some embodiments, $R^A$ is —$S(O)_2N(R^{12})(R^{11})$.

In some embodiments of a compound of Formula (IVa), (IVa-1), and (IVa-2), $R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl. In some embodiments, $R^{11}$ is hydrogen. In some embodiments, $R^{11}$ is optionally substituted $C_{1-6}$ alkyl. In some embodiments, $R^{11}$ is optionally substituted $C_{1-3}$ alkyl. In some embodiments, $R^{11}$ is methyl, ethyl, propyl, iso-propyl, n-butyl, iso-butyl, sec-butyl, t-butyl, —$CF_3$, —$CH_2CF_3$, or —$CH_2CH_2F$. In some embodiments, $R^{11}$ is optionally substituted $C_{2-6}$ alkenyl. In some embodiments, $R^{11}$ is optionally substituted $C_{2-6}$ alkynyl. In some embodiments, $R^{11}$ is optionally substituted $C_{1-6}$ heteroalkyl. In some embodiments, $R^{11}$ is optionally substituted $C_{3-8}$ cycloalkyl. In some embodiments, $R^{11}$ is optionally substituted $C_{2-7}$ heterocycloalkyl. In some embodiments, $R^{11}$ is optionally substituted phenyl. In some embodiments, $R^{11}$ is optionally substituted heteroaryl. In some embodiments, $R^{11}$ is optionally substituted —$C_{1-4}$ alkylene-$C_{3-8}$ cycloalkyl. In some embodiments, $R^{11}$ is optionally substituted —$C_{1-4}$ alkylene-$C_{2-7}$ heterocycloalkyl. In some embodiments, $R^{11}$ is optionally substituted —$C_{1-4}$ alkylene-phenyl. In some embodiments, $R^{11}$ is optionally substituted —$C_{1-4}$ alkylene-heteroaryl.

In some embodiments of a compound of Formula (IVa), (IVa-1), and (IVa-2), each of $R^{12}$ is independently selected from hydrogen, halogen, —OH, —$NO_2$, CN, $C_{1-6}$ alkyl, $C_{1-6}$ aminoalkyl, $C_{1-6}$ hydroxyalkyl, $C_{1-6}$ haloalkyl, $C_{1-6}$ heteroalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, CN, $C_{1-6}$ alkyl, $C_{1-6}$ alkoxy, and $C_{1-6}$ haloalkyl. In some embodiments of a compound of Formula (IVa), (IVa-1), and (IVa-2), each of $R^{12}$ is independently selected from hydrogen, —$NO_2$, CN, $C_{1-6}$ alkyl, $C_{1-6}$ aminoalkyl, $C_{1-6}$ hydroxyalkyl, $C_{1-6}$ haloalkyl, $C_{1-6}$ heteroalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, CN, $C_{1-6}$ alkyl, $C_{1-6}$ alkoxy, and $C_{1-6}$ haloalkyl. In some embodiments, $R^{12}$ is hydrogen. In some embodiments, $R^{12}$ is halogen. In some embodiments, $R^{12}$ is —OH. In some embodiments, $R^{12}$ is —$NO_2$. In some embodiments, $R^{12}$ is CN. In some embodiments, $R^{12}$ is $C_{1-6}$ alkyl. In some embodiments, $R^{12}$ is $C_{1-6}$ aminoalkyl. In some embodiments, $R^{12}$ is $C_{1-6}$ hydroxyalkyl. In some embodiments, $R^{12}$ is $C_{1-6}$ haloalkyl. In some embodiments, $R^{12}$ is $C_{1-6}$ heteroalkyl. In some embodiments, $R^{12}$ is $C_{3-6}$ carbocycle. In some embodiments, $R^{12}$ is and 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, CN, $C_{1-6}$ alkyl, $C_{1-6}$ alkoxy, and $C_{1-6}$ haloalkyl. In some embodiments, the one or more substituents is halogen. In some embodiments, the one or more substituents is —OH. In some embodiments, the one or more substituents is oxo. In some embodiments, the one or more substituents is amino. In some embodiments, the one or more substituents is —$NO_2$. In some embodiments, the one or more substituents is CN. In some embodiments, the one or more substituents is $C_{1-6}$ alkyl. In some embodiments, the one or more substituents is $C_{1-6}$ alkoxy. In some embodiments, the one or more substituents is $C_{1-6}$ haloalkyl.

In some embodiments of a compound of Formula (IVa), (IVa-1), and (IVa-2), $R^{B1}$ is optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, or optionally substituted bicyclic heteroaryl. In some embodiments, $R^{B1}$ is optionally substituted $C_{3-8}$ cycloalkyl. In some embodiments, $R^{B1}$ is optionally substituted $C_{2-9}$ heterocycloalkyl. In some embodiments, $R^{B1}$ is optionally substituted 5-6 membered heterocycloalkyl. In some embodiments, $R^{B1}$ is optionally substituted naphthyl. In some embodiments, $R^{B1}$ is optionally substituted phenyl. In some embodiments, $R^{B1}$ is optionally substituted monocyclic heteroaryl. In some embodiments, $R^{B1}$ is optionally substituted bicyclic heteroaryl.

In some embodiments of a compound of Formula (IVa), (IVa-1), and (IVa-2), $R^{Y1}$ is hydrogen, halo, —CN, —$NO_2$, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$, optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, and optionally substituted bicyclic heteroaryl. In some embodiments, $R^{Y1}$ is hydrogen. In some embodiments, $R^{Y1}$ is halo. In some embodiments, $R^{Y1}$ is —CN. In some embodiments, $R^{Y1}$ is —$NO_2$. In some embodiments, $R^{Y1}$ is —$OR^{11}$. In some embodiments, $R^{Y1}$ is —$SR^{11}$. In some embodiments, $R^{Y1}$ is —$N(R^{12})(R^{11})$ In some embodiments, $R^{Y1}$ is optionally substituted $C_{1-6}$ alkyl. In some embodiments, $R^{Y1}$ is optionally substituted $C_{1-6}$ heteroalkyl. In some embodiments, $R^{Y1}$ is optionally substituted $C_{2-6}$ alkenyl. In some embodiments, $R^{Y1}$ is optionally substituted $C_{2-6}$ alkynyl. In some embodiments, $R^{Y1}$ is —$OR^{11}$. In some embodiments, $R^{Y1}$ is —$SR^{11}$. In some embodiments, $R^{Y1}$ is —$N(R^{12})(R^{11})$ In some embodiments, $R^{Y1}$ is —$C(O)R^{12}$. In some embodiments, $R^{Y1}$ is —$C(O)OR^{12}$. In some embodiments, $R^{Y1}$ is —$OC(O)R^{12}$. In some embodiments, $R^{Y1}$ is —$OC(O)N(R^{12})(R^{11})$. In some embodiments, $R^{Y1}$ is —$C(O)N(R^{12})(R^{11})$. In some embodiments, $R^{Y1}$ is —$N(R^{12})C(O)R^{12}$. In some embodiments, $R^{11}$ is —$N(R^{12})C(O)OR^{12}$. In some embodiments, $R^{11}$ is —$N(R^{12})C(O)N(R^{12})(R^{11})$ In some embodiments, $R^{Y1}$ is —$N(R^{12})S(O)_2(R^{12})$. In some embodiments, $R^{Y1}$ is —$S(O)R^{12}$. In some embodiments, $R^{Y1}$ is —$S(O)_2R^{12}$. In some embodiments, $R^{Y1}$ is —$S(O)_2N(R^{12})(R^{11})$. In some embodiments, $R^{Y1}$ is optionally substituted $C_{3-8}$ cycloalkyl. In some embodiments, $R^{Y1}$ is optionally substituted $C_{2-9}$ heterocycloalkyl. In some embodiments, $R^{Y1}$ is optionally substituted naphthyl. In some embodiments, $R^{Y1}$ is optionally substituted phenyl. In some embodiments, $R^{Y1}$ is optionally substituted monocyclic heteroaryl. In some embodiments, $R^{Y1}$ is optionally substituted bicyclic heteroaryl.

In some embodiments of a compound of Formula (IVa), (IVa-1), and (IVa-2), $R^{Y2}$ is hydrogen, halo, —CN, —$NO_2$, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$, optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, and optionally substituted bicyclic heteroaryl. In some embodiments, $R^{Y2}$ is hydrogen. In some embodiments, $R^{Y2}$ is halo. In some embodiments, $R^{Y2}$ is —CN. In some embodiments, $R^{Y2}$ is —$NO_2$. In some embodiments, $R^{Y2}$ is —$OR^{11}$. In some embodiments, $R^{Y2}$ is —$SR^{11}$. In some embodiments, $R^{Y2}$ is —$N(R^{12})(R^{11})$. In some embodiments, $R^{Y2}$ is optionally substituted $C_{1-6}$ alkyl. In some embodiments, $R^2$ is optionally substituted $C_{1-6}$ heteroalkyl. In some embodiments, $R^{Y2}$ is optionally substituted $C_{2-6}$ alkenyl. In some embodiments, $R^{Y2}$ is optionally substituted $C_{2-6}$ alkynyl. In some embodiments, $R^{Y2}$ is —$OR^{11}$. In some embodiments, $R^2$ is —$SR^{11}$. In some embodiments, $R^2$ is —$N(R^{12})(R^{11})$. In some embodiments, $R^{Y2}$ is —$C(O)R^{12}$. In some embodiments, $R^{Y2}$ is —$C(O)OR^{12}$. In some embodiments, $R^{Y2}$ is —$OC(O)R^{12}$. In some embodiments, $R^{Y2}$ is —$OC(O)N(R^{12})(R^{11})$. In some embodiments, $R^{Y2}$ is —$C(O)N(R^{12})(R^{11})$. In some embodiments, $R^{Y2}$ is —$N(R^{12})C(O)R^{12}$. In some embodiments, $R^{Y2}$ is —$N(R^{12})C(O)OR^{12}$. In some embodiments, $R^{Y2}$ is —$N(R^{12})C(O)N(R^{12})(R^{11})$. In some embodiments, $R^{Y2}$ is —$N(R^{12})S(O)_2(R^{12})$. In some embodiments, $R^{Y2}$ is —$S(O)R^{12}$. In some embodiments, $R^{Y2}$ is —$S(O)_2R^{12}$. In some embodiments, $R^{12}$ is —$S(O)_2N(R^{12})(R^{11})$. In some embodiments, $R^{Y2}$ is optionally substituted $C_{3-8}$ cycloalkyl. In some embodiments, $R^{Y2}$ is optionally substituted $C_{2-9}$ heterocycloalkyl. In some embodiments, $R^{Y2}$ is optionally substituted naphthyl. In some embodiments, $R^{Y2}$ is optionally substituted phenyl. In some embodiments, $R^{Y2}$ is optionally substituted monocyclic heteroaryl. In some embodiments, $R^{Y2}$ is optionally substituted bicyclic heteroaryl.

In some embodiments of a compound of Formula (IVa), (IVa-1), and (IVa-2), $R^{Y3}$ is hydrogen, halo, —CN, —$NO_2$, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$, optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, and optionally substituted bicyclic heteroaryl. In some embodiments, $R^{Y3}$ is hydrogen. In some embodiments, $R^{Y3}$ is halo. In some embodiments, $R^{Y3}$ is —CN. In some embodiments, $R^{Y3}$ is —$NO_2$. In some embodiments, $R^{Y3}$ is —$OR^{11}$. In some embodiments, $R^{Y3}$ is —$SR^{11}$. In some embodiments, $R^{Y3}$ is —$N(R^{12})(R^{11})$ In some embodiments, $R^{Y3}$ is optionally substituted $C_{1-6}$ alkyl. In some embodiments, $R^{Y3}$ is optionally substituted $C_{1-6}$ heteroalkyl. In some embodiments, $R^{Y3}$ is optionally substituted $C_{2-6}$ alkenyl. In some embodiments, $R^{Y3}$ is optionally substituted $C_{2-6}$ alkynyl. In some embodiments, $R^{Y3}$ is —$OR^{11}$. In some embodiments, $R^{Y3}$ is —$SR^{11}$. In some embodiments, $R^{Y3}$ is —$N(R^{12})(R^{11})$ In some embodiments, $R^{Y3}$ is —$C(O)R^{12}$. In some embodiments, $R^{Y3}$ is —$C(O)OR^{12}$. In some embodiments, $R^{Y3}$ is —$OC(O)R^{12}$. In some embodiments, $R^{Y3}$ is —$OC(O)N(R^{12})(R^{11})$. In some embodiments, $R^{Y3}$ is —$C(O)N(R^{12})(R^{11})$. In some embodiments, $R^{Y3}$ is —$N(R^{12})C(O)R^{12}$. In some embodiments, $R^{Y3}$ is —$N(R^{12})C(O)OR^{12}$. In some embodiments, $R^{Y3}$ is —$N(R^{12})C(O)N(R^{12})(R^{11})$ In some embodiments, $R^{Y3}$ is —$N(R^{12})S(O)_2(R^{12})$. In some embodiments, $R^{Y3}$ is —$S(O)R^{12}$. In some embodiments, $R^{Y3}$ is —$S(O)_2R^{12}$. In some embodiments, $R^{Y3}$ is —$S(O)_2N(R^{12})(R^{11})$. In some embodiments, $R^{Y3}$ is optionally substituted $C_{3-8}$ cycloalkyl. In some embodiments, $R^{Y3}$ is optionally substituted $C_{2-9}$ heterocycloalkyl. In some embodiments, $R^{Y3}$ is optionally substituted naphthyl. In some embodiments, $R^{Y3}$ is optionally substituted phenyl. In some embodiments, $R^{Y3}$ is optionally substituted monocyclic heteroaryl. In some embodiments, $R^{Y3}$ is optionally substituted bicyclic heteroaryl.

In some embodiments of a compound of Formula (IVa), (IVa-1), and (IVa-2), $R^{Y4}$ is hydrogen, halo, —CN, —$NO_2$, —$OR^{11}$, —$SR^{11}$, —$N(R^{12})(R^{11})$, optionally substituted $C_{1-6}$ alkyl, optionally substituted $C_{1-6}$ heteroalkyl, optionally substituted $C_{2-6}$ alkenyl, optionally substituted $C_{2-6}$ alkynyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$, optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, and optionally substituted bicyclic heteroaryl. In some embodiments, $R^{Y4}$ is hydrogen. In some embodiments, $R^{Y4}$ is halo. In some embodiments, $R^{Y4}$ is —CN. In some embodiments, $R^{Y4}$ is —$NO_2$. In some embodiments, $R^{Y4}$ is —$OR^{11}$. In some embodiments, $R^{Y4}$ is —$SR^{11}$. In some embodiments, $R^{Y4}$ is —$N(R^{12})(R^{11})$. In some embodiments, $R^{Y4}$ is optionally substituted $C_{1-6}$ alkyl. In some embodiments, $R^{Y4}$ is optionally substituted $C_{1-6}$ heteroalkyl. In some embodiments, $R^{Y4}$ is optionally substituted $C_{2-6}$ alkenyl. In some embodiments, $R^{Y4}$ is optionally substituted $C_{2-6}$ alkynyl. In some embodiments, $R^{Y4}$ is —$OR^{11}$. In some embodiments, $R^{Y4}$ is —$SR^{11}$. In some embodiments, $R^{Y4}$ is —$N(R^{12})(R^{11})$. In some embodiments, $R^{Y4}$ is —$C(O)R^{12}$. In some embodiments, $R^{Y4}$ is —$C(O)OR^{12}$. In some embodiments, $R^{Y4}$ is —$OC(O)R^{12}$. In some embodiments, $R^{Y4}$ is —$OC(O)N(R^{12})(R^{11})$. In some embodiments, $R^{Y4}$ is —$C(O)N(R^{12})(R^{11})$. In some embodiments, $R^{Y4}$ is —$N(R^{12})C(O)R^{12}$. In some embodiments, $R^{Y4}$ is —$N(R^{12})C(O)OR^{12}$. In some embodiments, $R^{Y4}$ is —$N(R^{12})C(O)N(R^{12})(R^{11})$. In some embodiments, $R^{Y4}$ is —$N(R^{12})S(O)_2(R^{12})$. In some embodiments, $R^{Y4}$ is —$S(O)R^{12}$. In some embodiments, $R^{Y4}$ is —$S(O)_2R^{12}$. In some embodiments, $R^{Y4}$ is —$S(O)_2N(R^{12})(R^{11})$. In some embodiments, $R^{Y4}$ is optionally substituted $C_{3-8}$ cycloalkyl. In some embodiments, $R^{Y4}$ is optionally substituted $C_{2-9}$ heterocycloalkyl. In some embodiments, $R^{Y4}$ is optionally substituted naphthyl. In some embodiments, $R^{Y4}$ is optionally substituted phenyl. In some embodiments, $R^{Y4}$ is optionally substituted monocyclic heteroaryl. In some embodiments, $R^{Y4}$ is optionally substituted bicyclic heteroaryl.

In some embodiments of a compound of Formula (IVa), (IVa-1), and (IVa-2), $R^{Y1}$ and $R^{Y2}$ are taken together with the carbons to which they are attached to form an optionally substituted $C_{3-8}$ cycloalkyl or optionally substituted $C_{2-9}$ heterocycloalkyl. In some embodiments of a compound of Formula (IVa), (IVa-1), and (IVa-2), $R^{Y3}$ and $R^{Y4}$ are taken together with the carbons to which they are attached to form an optionally substituted $C_{3-8}$ cycloalkyl or optionally substituted $C_{2-9}$ heterocycloalkyl.

In some embodiments of a compound of Formula (IVa), (IVa-1), and (IVa-2), m is 1, 2, 3, or 4. In some embodiments, m is 1. In some embodiments, m is 2. In some embodiments, m is 3. In some embodiments, m is 4.

In some embodiments of a compound of Formula (IVa), (IVa-1), and (IVa-2) p is 0 or 1. In some embodiments, p is 0. In some embodiments, p is 1.

In some embodiments of a compound of Formula (IVa-2), $Y^1$ is N or $CR^{Y1}$; $Y^2$ is N or $CR^{Y2}$; $Y^3$ is $CR^{Y3}$; $Y^4$ is $CR^{Y4}$; each of $R^{Y1}$, $R^{Y2}$, $R^{Y3}$, and $R^{Y4}$ is independently hydrogen or $C_1$-$C_6$ alkyl; $R^1$ is hydrogen or $C_1$-$C_6$ alkyl; p is 0;

and each $R^A$ is independently OH, $C_{1-6}$ alkoxyl (e.g., —$OCH_3$), $C_{1-6}$ alkyl, $C_{1-6}$haloalkyl, or $C_3$-$C_6$ cycloalkyl (e.g., cyclopropyl); and $R^{B1}$ is 5 membered heteroaryl optionally substituted with one or more substituents selected from $C_{1-3}$ haloalkyl and $C_{1-3}$ alkyl In some embodiments, $R^{B1}$ is substituted with 1 or 2 substituents selected from $C_{1-3}$ haloalkyl and $C_{1-3}$ alkyl. In some embodiments, each $R^A$ is independently OH, $C_{1-3}$ alkyl, $C_{1-3}$ alkoxyl (e.g., —$OCH_3$), $C_{1-3}$ haloalkyl, or $C_3$-$C_6$ cycloalkyl (e.g., cyclopropyl). In some embodiments, each $R^A$ is independently $C_{1-3}$ alkoxyl (e.g., —$OCH_3$) or $C_3$-$C_6$ cycloalkyl (e.g., cyclopropyl). In some embodiments, each $R^A$ is independently —$OCH_3$, $C_{1-3}$ alkyl, $C_{1-3}$ haloalkyl, or cyclopropyl. In some embodiments, each $R^A$ is independently $C_{1-3}$ alkoxyl, $C_{1-3}$ alkyl, $C_{1-3}$ haloalkyl, or cyclopropyl. In some embodiments, —$OCH_3$ is —$OCD_3$.

In one aspect, described herein is a compound having the structure of Formula (VI), or a salt or solvate thereof:

Formula (VI)

wherein, ring C is phenyl or a 5 membered heteroaryl, wherein each of the phenyl or heteroaryl is optionally substituted;

ring D is an aromatic, saturated or partially saturated 6 membered carbocycle or heterocycle, wherein each of the carbocycle or heterocycle is optionally substituted;

each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl; or $R^8$ and $R^9$ taken together form an oxo; or $R^8$ and $R^9$ taken together with the carbon to which they are attached form an optionally substituted 3-6 membered cycloalkyl or heterocycloalkyl;

ring A is phenyl, naphthyl, monocyclic heteroaryl, bicyclic heteroaryl, cycloalkyl, or heterocycloalkyl;

each of $R^A$ is independently selected from halogen, —$NO_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$;

$R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl;

each of $R^{12}$ is independently selected from hydrogen, halogen, —OH, —$NO_2$, —CN, $C_{1-6}$ alkyl, $C_{1-6}$ aminoalkyl, $C_{1-6}$ hydroxyalkyl, $C_{1-6}$ haloalkyl, and $C_{3-6}$ carbocycle, 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, —CN, $C_{1-6}$ alkyl, $C_{1-6}$ alkoxy, and $C_{1-6}$ haloalkyl;

$R^B$ is hydrogen, halo, —CN, —$NO_2$, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})S(O)_2(R^{12})$, —$S(O)R^{12}$, —$S(O)_2R^{12}$, —$S(O)_2N(R^{12})(R^{11})$ optionally substituted $C_{3-8}$ cycloalkyl, optionally substituted $C_{2-9}$ heterocycloalkyl, optionally substituted naphthyl, optionally substituted phenyl, optionally substituted monocyclic heteroaryl, or optionally substituted bicyclic heteroaryl; or m is 0, 1, 2, 3, or 4; and p is 0 or 1

In some embodiments of Formula (VI), each of $R^{12}$ is independently selected from hydrogen, —$NO_2$, —CN, $C_{1-6}$ alkyl, $C_{1-6}$ aminoalkyl, $C_{1-6}$ hydroxyalkyl, $C_{1-6}$ haloalkyl, and $C_{3-6}$ carbocycle, 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, —CN, $C_{1-6}$ alkyl, $C_{1-6}$ alkoxy, and $C_{1-6}$ haloalkyl.

In some embodiments of Formula (VI), ring C is phenyl or a 5 membered heteroaryl, wherein each of the phenyl or heteroaryl is optionally substituted with 1, 2, 3, or 4 $R^{1C}$, and each $R^{1C}$ is independently halogen, —CN, —$NO_2$, —OH, —$OR^a$, —$OC(=O)R^a$, —$OC(=O)OR^b$, —$OC(=O)NR^cR^d$, —SH, —$SR^a$, —$S(=O)R^a$, —$S(=O)_2R^a$, —$S(=O)_2NR^cR^d$, —$NR^cR^d$, —$NR^bC(=O)NR^cR^d$, —$NR^bC(=O)R^a$, —$NR^bC(=O)OR^b$, —$NR^bS(=O)_2R^a$, —$C(=O)R^a$, —$C(=O)OR^b$, —$C(=O)NR^cR^d$, $C_{1-6}$alkyl, $C_{1-6}$haloalkyl, $C_{1-6}$ hydroxyalkyl, $C_{1-6}$aminoalkyl, $C_{1-6}$heteroalkyl, $C_{2-6}$alkenyl, $C_2$-$C_6$alkynyl, $C_{3-8}$ cycloalkyl, $C_{2-7}$ heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{1Ca}$;

ring D is an aromatic, saturated or partially saturated 6 membered carbocycle or heterocycle, wherein each of the carbocycle or heterocycle is optionally substituted with 1, 2, 3, 4 or 5, or 6 $R^{1D}$, and each $R^{1D}$ is independently halogen, —CN, —$NO_2$, —OH, —$OR^a$, —$OC(=O)R^a$, —$OC(=O)OR^b$, —$OC(=O)NR^cR^d$, —SH, —$SR^a$, —$S(=O)R^a$, —$S(=O)_2R^a$, —$S(=O)_2NR^cR^d$, —$NR^cR^d$, —$NR^bC(=O)NR^cR^d$, —$NR^bC(=O)R^a$, —$NR^bC(=O)OR^b$, —$NR^b$ $S(=O)_2R^a$, —$C(=O)R^a$, —$C(=O)OR^b$, —$C(=O)$ $NR^cR^d$, $C_{1-6}$alkyl, $C_{1-6}$haloalkyl, $C_{1-6}$ hydroxyalkyl, $C_{1-6}$aminoalkyl, $C_{1-6}$heteroalkyl, $C_{2-6}$alkenyl, $C_2$-$C_6$alkynyl, $C_{3-8}$ cycloalkyl, $C_{2-7}$ heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{1Da}$;

each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl, or $R^8$ and $R^9$ taken together form an oxo, or $R^8$ and $R^9$ taken together with the carbon to which they are attached form an optionally substituted 3-6 membered cycloalkyl or heterocycloalkyl, wherein the alkyl, alkenyl, alkynyl, cycloalkyl or heterocycloalkyl is optionally substituted with one or more substituents independently selected from: halogen, amino, —OH, —$NO_2$, oxo, —CN, $C_{1-3}$ alkoxyl, $C_{1-3}$ alkyl and $C_{1-3}$ haloalkyl;

each of $R^A$ is independently selected from halogen, —$NO_2$, oxo, —CN, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, —$C(O)OR^{12}$, —$OC(O)$ $R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$, wherein the alkyl, alkenyl, alkynyl, heteroalkyl, cycloalkyl, or heterocycloalkyl is optionally substituted with one or more substituents independently selected from: halogen, —OH, —$NO_2$, oxo, amino, —CN, $C_{1-6}$ alkoxyl, $C_{1-6}$ alkyl, $C_{1-6}$ haloalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, amino, —$NO_2$, oxo, —CN, $C_{1-6}$ alkyl, $C_{1-6}$ alkoxy, and $C_{1-6}$ haloalkyl;

$R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl, wherein the alkyl, alkenyl, alkynyl, heteroalkyl, alkylene, cycloalkyl, heterocycloalkyl, phenyl, or heteroaryl is optionally substituted with one or more substituents independently selected from: halogen, —OH, amino, —$NO_2$, oxo, $C_{1-6}$ alkoxy, —CN, $C_{1-6}$ alkyl, and $C_{1-6}$haloalkyl;

each of $R^{12}$ is independently selected from hydrogen, halogen, —OH, —$NO_2$, —CN, $C_{1-6}$ alkyl, $C_{1-6}$ aminoalkyl, $C_{1-6}$ hydroxyalkyl, $C_{1-6}$ haloalkyl, and $C_{3-6}$ carbocycle, 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, —CN, $C_{1-6}$ alkyl, $C_{1-6}$ alkoxy, and $C_{1-6}$ haloalkyl;

$R^B$ is hydrogen, halo, —CN, —$NO_2$, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, —$OR^{11}$, —$SR^{11}$, $N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —N(R$^{12}$)C(O)OR$^{12}$, —N(R$^{12}$)C(O)N(R$^{12}$)(R$^{11}$), —N(R$^{12}$)S(O)$_2$(R$^{12}$), —S(O)R$^{12}$, —S(O)$_2$R$^{12}$, —S(O)$_2$N(R$^{12}$)(R$^{11}$), optionally substituted C$_{3-8}$ cycloalkyl, optionally substituted C$_{2-9}$ heterocycloalkyl, optionally substituted naphthyl, optionally substituted phenyl, optionally substituted monocyclic heteroaryl, or optionally substituted bicyclic heteroaryl, wherein each of the alkyl, alkenyl, alkynyl, heteroalkyl, cycloalkyl, heterocycloalkyl, naphthyl, phenyl or heteroaryl is optionally substituted with one or more substituents independently selected from: halogen, —NO$_2$, oxo, —CN, optionally substituted C$_{1-6}$ alkyl, optionally substituted C$_{2-6}$ alkenyl, optionally substituted C$_{2-6}$ alkynyl, optionally substituted C$_{1-6}$ heteroalkyl, optionally substituted C$_{3-8}$ cycloalkyl, optionally substituted C$_{2-7}$ heterocycloalkyl, —OR$^{11}$, —SR$^{11}$, —N(R$^{12}$)(R$^{11}$), —C(O)R$^{12}$, —C(O)OR$^{12}$, —OC(O) R$^{12}$, —OC(O)N(R$^{12}$)(R$^{11}$), —C(O)N(R$^{12}$)(R$^{11}$), —N(R$^{12}$)C(O)R$^{12}$, —N(R$^{12}$)C(O)OR$^{12}$, —N(R$^{12}$)C (O)N(R$^{12}$)(R$^{11}$), —N(R$^{12}$)S(O)$_2$(R$^{12}$), —S(O)R$^{12}$, —S(O)$_2$R$^{12}$, and —S(O)$_2$N(R$^{12}$)(R$^{11}$), wherein the alkyl, alkenyl, alkynyl, heteroalkyl, cycloalkyl, or heterocycloalkyl is optionally substituted with one or more substituents independently selected from: halogen, —OH, —NO$_2$, amino, —NH(C$_{1-6}$ alkyl), —N(C$_{1-6}$ alkyl)$_2$, oxo, —CN, C$_{1-3}$ alkoxyl, C$_{1-3}$ alkyl and C$_{1-3}$ haloalkyl;

each R$^a$ is independently C$_1$-C$_6$alkyl, C$_1$-C$_6$haloalkyl, C$_1$-C$_6$ hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, —C$_1$-C$_6$alkylene-cycloalkyl, —C$_1$-C$_6$alkylene-heterocycloalkyl, —C$_1$-C$_6$alkylene-aryl, or —C$_1$-C$_6$alkylene-heteroaryl; wherein each alkyl, alkylene, alkenyl, alkynyl, cycloalkyl, heterocycloalkyl, aryl, and heteroaryl is independently optionally substituted with one or more oxo, halogen, —CN, —OH, —OC$_1$-C$_6$alkyl, —S(═O)C$_1$-C$_6$alkyl, —S(═O)$_2$C$_1$-C$_6$alkyl, —S(═O)$_2$NH$_2$, —S(═O)$_2$NHC$_1$-C$_6$alkyl, —S(═O)$_2$N(C$_1$-C$_6$alkyl)$_2$, —NH$_2$, —NHC$_1$-C$_6$alkyl, —N(C$_1$-C$_6$alkyl)$_2$, —NHC(═O)OC$_1$-C$_6$alkyl, —C(═O)C$_1$-C$_6$alkyl, —C(═O)OH, —C(═O)OC$_1$-C$_6$alkyl, —C(═O)NH$_2$, —C(═O)N(C$_1$-C$_6$alkyl)$_2$, —C(═O)NHC$_1$-C$_6$alkyl, C$_1$-C$_6$alkyl, C$_1$-C$_6$haloalkyl, C$_1$-C$_6$ hydroxyalkyl, C$_1$-C$_6$aminoalkyl, or C$_1$-C$_6$heteroalkyl;

each R$^b$ is independently hydrogen, C$_1$-C$_6$alkyl, C$_1$-C$_6$haloalkyl, C$_1$-C$_6$ hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, —C$_1$-C$_6$alkylene-cycloalkyl, —C$_1$-C$_6$alkylene-heterocycloalkyl, —C$_1$-C$_6$alkylene-aryl, or —C$_1$-C$_6$alkylene-heteroaryl; wherein each alkyl, alkylene, alkenyl, alkynyl, cycloalkyl, heterocycloalkyl, aryl, and heteroaryl is independently optionally substituted with one or more oxo, halogen, —CN, —OH, —OC$_1$-C$_6$alkyl, —S(═O)C$_1$-C$_6$alkyl, —S(═O)$_2$C$_1$-C$_6$alkyl, —S(═O)$_2$NH$_2$, —S(═O)$_2$NH C$_1$-C$_6$alkyl, —S(═O)$_2$N(C$_1$-C$_6$alkyl)$_2$, —NH$_2$, —NHC$_1$-C$_6$alkyl, —N(C$_1$-C$_6$alkyl)$_2$, —NHC(═O) OC$_1$-C$_6$alkyl, —C(═O)C$_1$-C$_6$alkyl, —C(═O)OH, —C(═O)OC$_1$-C$_6$alkyl, —C(═O)NH$_2$, —C(═O)N (C$_1$-C$_6$alkyl)$_2$, —C(═O)NHC$_1$-C$_6$alkyl, C$_1$-C$_6$alkyl, C$_1$-C$_6$haloalkyl, C$_1$-C$_6$ hydroxyalkyl, C$_1$-C$_6$aminoalkyl, or C$_1$-C$_6$heteroalkyl;

each R$^c$ and R$^d$ are independently hydrogen, C$_1$-C$_6$alkyl, C$_1$-C$_6$haloalkyl, C$_1$-C$_6$ hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, —C$_1$-C$_6$alkylene-cycloalkyl, —C$_1$-C$_6$alkylene-heterocycloalkyl, —C$_1$-C$_6$alkylene-aryl, or —C$_1$-C$_6$alkylene-heteroaryl; wherein each alkyl, alkenyl, alkynyl, cycloalkyl, heterocycloalkyl, aryl, and heteroaryl is independently optionally substituted with one or more oxo, halogen, —CN, —OH, —OC$_1$-C$_6$alkyl, —S(═O)C$_1$-C$_6$alkyl, —S(═O)$_2$C$_1$-C$_6$alkyl, —S(═O)$_2$NH$_2$, —S(═O)$_2$NHC$_1$-C$_6$alkyl, —S(═O)$_2$N(C$_1$-C$_6$alkyl)$_2$, —NH$_2$, —NHC$_1$-C$_6$alkyl, —N(C$_1$-C$_6$alkyl)$_2$, —NHC(═O)OC$_1$-C$_6$alkyl, —C(═O) C$_1$-C$_6$alkyl, —C(═O)OH, —C(═O)OC$_1$-C$_6$alkyl, —C(═O)NH$_2$, —C(═O)N(C$_1$-C$_6$alkyl)$_2$, —C(═O)NHC$_1$-C$_6$alkyl, C$_1$-C$_6$alkyl, C$_1$-C$_6$haloalkyl, C$_1$-C$_6$ hydroxyalkyl, C$_1$-C$_6$aminoalkyl, or C$_1$-C$_6$heteroalkyl;

or R$^c$ and R$^d$ are taken together with the atom to which they are attached to form a heterocycloalkyl optionally substituted with one or more oxo, halogen, —CN, —OH, —OC$_1$-C$_6$alkyl, —S(═O)C$_1$-C$_6$alkyl, —S(═O)$_2$C$_1$-C$_6$alkyl, —S(═O)$_2$NH$_2$, —S(═O)$_2$NHC$_1$-C$_6$alkyl, —S(═O)$_2$N(C$_1$-C$_6$alkyl)$_2$, —NH$_2$, —NHC$_1$-C$_6$alkyl, —N(C$_1$-C$_6$alkyl)$_2$, —NHC (═O)OC$_1$-C$_6$alkyl, —C(═O) C$_1$-C$_6$alkyl, —C(═O) OH, —C(═O)OC$_1$-C$_6$alkyl, —C(═O)NH$_2$, —C(═O) N(C$_1$-C$_6$alkyl)$_2$, —C(═O)NHC$_1$-C$_6$alkyl, C$_1$-C$_6$alkyl, C$_1$-C$_6$haloalkyl, C$_1$-C$_6$ hydroxyalkyl, C$_1$-C$_6$aminoalkyl, or C$_1$-C$_6$heteroalkyl;

each R$^{1Ca}$ and R$^{1Da}$ is independently halogen, —CN, —NO$_2$, —OH, —OR$^a$, —OC(═O)R$^a$, —OC(═O) OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C (═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$ hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

m is 0, 1, 2, 3, or 4; and p is 0 or 1.

In some embodiments of Formula (VI), ring C is 5 membered heteroaryl and ring D is 6 membered heteroaryl. In some embodiments, ring C is 5 membered heteroaryl and ring D is 6 membered heterocycloalkyl.

In some embodiments of Formula (VI), each of ring C and ring D is independently optionally substituted with one or more substituents selected from halo, —CN, —OR$^a$, —SH, —SR$^a$, —NR$^c$R$^d$, optionally substituted C$_{1-6}$ alkyl, optionally substituted C$_{1-6}$ heteroalkyl, optionally substituted C$_{2-6}$ alkenyl, and optionally substituted C$_{2-6}$ alkynyl, and wherein the alkyl, heteroalkyl, alkenyl, or alkynyl is optionally substituted with one or more substituents independently selected from: halogen, amino, —OH, —NO$_2$, —CN, and C$_{1-3}$ alkoxyl.

In some embodiments of Formula (VI), is

-continued or .

In some embodiments of Formula (VI), ring A is phenyl. In some embodiments, ring A is naphthyl. In some embodiments, ring A is 5 or 6 membered monocyclic heteroaryl. In some embodiments, ring A is a 6 membered monocyclic heteroaryl containing 1-3 heteroatoms.

In some embodiments of Formula (VI), ring A is pyridine, pyrimidine, pyrazine, pyridazine, triazine, imidazole, pyrazole, triazole, oxazole, isoxazole, or thiophene. In some embodiments, $(R^A)_m$—A is , , , , , , , , , , , , , , , , .

-continued

, , , , or .

In some embodiments, $(R^A)_m$—A is .

, , or .

In some embodiments, $(R^A)_m$—A is , , , , or .

In some embodiments, $(R^A)_m$—A is , or .

In some embodiments, $(R^A)_m$—A is $R^A$ pyrimidine .

In some embodiments, $(R^A)_m$—A is $R^A$ pyrimidine $R^A$ .

In some embodiments, $(R^A)_m$—A is $R^A$ pyrimidine .

In some embodiments, $(R^A)_m$—A is $R^A$ pyrimidine $R^A$ .

In some embodiments, $(R^A)_m$—A is $R^A$ pyridine , $R^A$ pyridine $R^A$ , or $R^A$ pyridine $R^A$ .

In some embodiments, $(R^A)_m$—A is $R^A$ pyridine .

In some embodiments, $(R^A)_m$—A is $R^A$ pyridine $R^A$ .

In some embodiments, $(R^A)_m$—A is $R^A$ pyridazine $R^A$ .

In some embodiments, $(R^A)_m$—A is $R^A$ pyridazine , $R^A$ pyridazine $R^A$ , or $R^A$ pyridazine $R^A$ .

In some embodiments, $(R^A)_m$—A is $R^A$ pyrazole , $R^A$ pyrazole $R^A$ , $R^A$ imidazole $R^A$ , $R^A$ imidazole $R^A$ , $R^A$ pyrazole $R^A$ , $R^A$ pyrazole $R^A$ , $R^A$ pyridazine , $R^A$ triazole $R^A$ , or

63

-continued

In some embodiments of Formula (VI), ring A is aryl. In some embodiments, ring A is phenyl. In some embodiments of Formula (VI), In some embodiments, In some embodiments of Formula (VI), ring A is unsubstituted aryl (e.g., phenyl). In some embodiments of Formula (VI), ring A is aryl (e.g., phenyl) that is optionally substituted with 1 to 5 $R^4$. In some embodiments of Formula (VI), ring A is aryl (e.g., phenyl) that is substituted with 1 $R^4$. In some embodiments of Formula (VI), ring A is aryl (e.g., phenyl) that is substituted with 2 $R^4$. In some embodiments of Formula (VI), ring A is aryl (e.g., phenyl) that is substituted with 3 $R^4$. In some embodiments of Formula (VI), ring A is aryl (e.g., phenyl) that is substituted with 4 $R^4$. In some embodiments of Formula (VI), ring A is aryl (e.g., phenyl) that is substituted with $R^4$.

In some embodiments of Formula (VI), ring A is bicyclic heteroaryl. In some embodiments, ring A is fused 5-6, 6-6, or 6-5 bicyclic heteroaryl.

In some embodiments of Formula (VI), each of $R^4$ is independently selected from halogen, —$NO_2$, oxo, —CN, optionally substituted $C_{1-6}$ alkyl, optionally substituted $C_{1-6}$heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, —$C(O)OR^{12}$, —OC(O)$R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$. In some embodiments, each $R^4$ is independently substituted with one or more substituents independently selected from: halogen, —OH, —$NO_2$, amino, —CN, $C_{1-6}$ alkoxyl, $C_{1-6}$ alkyl, $C_{1-6}$ haloalkyl, $C_{3-6}$ carbocycle, and 3- to 6-membered heterocycle, wherein the $C_{3-6}$ carbocycle and 3- to 6-membered heterocycle is optionally substituted with one or more substituents independently selected from halogen, —OH, amino, —$NO_2$, oxo, —CN, $C_{1-6}$ alkyl, $C_{1-6}$ alkoxy, and $C_{1-6}$haloalkyl.

In some embodiments of Formula (VI), is selected from:

65

-continued

66

-continued

-continued

In some embodiments,

In some embodiments,

In some embodiments,

In some embodiments,

In some embodiments,

In some embodiments,

In some embodiments,

In some embodiments,

In some embodiments of Formula (VI), p is 0. In some embodiments, p is 1.

In some embodiments of Formula (VI), each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl. In some embodiments of Formula (VI), each of $R^8$ and $R^9$ is independently selected from hydrogen, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl.

In some embodiments of Formula (VI), $R^8$ and $R^9$ taken together form an oxo.

In some embodiments of Formula (VI), $R^8$ and $R^9$ taken together with the carbon to which they are attached form an optionally substituted 3-6 membered cycloalkyl or heterocycloalkyl.

In some embodiments of Formula (VI), $R^B$ is halo, —CN, —NO$_2$, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, —OR$^{11}$, —SR$^{11}$, —N(R$^{12}$)(R$^{11}$), —C(O)R$^{12}$, —C(O)OR$^{12}$, —OC(O)R$^{12}$, —OC(O)N(R$^{12}$)(R$^{11}$), —C(O)N(R$^{12}$)(R$^{11}$), —N(R$^{12}$)C(O) R$^{12}$, —N(R$^{12}$)C(O)OR$^{12}$, —N(R$^{12}$)C(O)N(R$^{12}$)(R$^{11}$), —N(R$^{12}$)S(O)$_2$(R$^{12}$), —S(O)R$^{12}$, —S(O)$_2$R$^{12}$, —S(O)$_2$N (R$^{12}$)(R$^{11}$) optionally substituted $C_{3-8}$ cycloalkyl, optionally substituted $C_{2-9}$ heterocycloalkyl, optionally substituted phenyl, optionally substituted monocyclic heteroaryl, or optionally substituted bicyclic heteroaryl. In some embodiments, $R^B$ is optionally substituted 5 membered monocyclic heteroaryl with 1 to 4 heteroatoms selected from N, O, S and P. In some embodiments, $R^B$ is imidazole, pyrazole, triazole, or tetrazole, each of which optionally substituted. In some embodiments, $R^B$ is optionally substituted fused 5-6, 6-6 or 6-5 heteroaryl.

In some embodiments of Formula (VI), $R^B$ is optionally substituted with one or more substituents independently selected from halogen, —NO$_2$, oxo, —CN, optionally substituted $C_{1-6}$ alkyl, optionally substituted $C_{1-6}$ heteroalkyl, optionally substituted $C_{3-8}$ cycloalkyl, optionally substituted $C_{2-7}$ heterocycloalkyl, —OR$^{11}$, —SR$^{11}$, —N(R$^{12}$)(R$^{11}$), —C(O)R$^{12}$, —C(O)OR$^{12}$, —OC(O)R$^{12}$, —OC(O)N(R$^{12}$) (R$^{11}$), —C(O)N(R$^{12}$)(R$^{11}$), —N(R$^{12}$)C(O)R$^{12}$, —N(R$^{12}$)C (O)OR$^{12}$, —N(R$^{12}$)C(O)N(R$^{12}$)(R$^{11}$), —N(R$^{12}$)S(O)$_2$(R$^{12}$), —S(O)R$^{12}$, —S(O)$_2$R$^{12}$, and —S(O)$_2$N(R$^{12}$)(R$^{11}$) wherein the alkyl, alkenyl, alkynyl, heteroalkyl, cycloalkyl, or heterocycloalkyl is optionally substituted with one or more substituents independently selected from: halogen, —OH, —NO$_2$, amino, oxo, —CN, $C_{1-3}$ alkoxyl, $C_{1-3}$ alkyl and $C_{1-3}$ haloalkyl. In some embodiments, $R^B$ is optionally substituted with one or more substituents independently selected from halogen, —OR$^{11}$, —NO$_2$, oxo, —CN, optionally substituted $C_{1-6}$ haloalkyl, optionally substituted $C_{1-6}$ alkyl, optionally substituted $C_{1-6}$ aminoalkyl, optionally substituted $C_{1-6}$ hydroxyalkyl, optionally substituted $C_{1-6}$ heteroalkyl, optionally substituted $C_{3-8}$ cycloalkyl, and optionally substituted $C_{2-7}$ heterocycloalkyl. In some embodiments, $R^B$ is optionally substituted with one or more substituents independently selected from halogen, —OR$^{11}$, —NO$_2$, oxo, —CN, $C_{1-3}$ haloalkyl, $C_{1-3}$ alkyl, $C_{1-3}$ aminoalkyl, $C_{1-3}$ hydroxyalkyl, optionally substituted $C_{1-4}$ heteroalkyl (e.g., —CH$_2$C(=O)N(CH$_3$)$_2$), optionally substituted $C_{3-6}$ cycloalkyl, and optionally substituted $C_{2-5}$ heterocycloalkyl. In some embodiments, $R^B$ is optionally substituted $C_{3-8}$ cycloalkyl. In some embodiments, $R^B$ is $C_3$ cycloalkyl. In some embodiments, $R^B$ is $C_5$ cycloalkyl. In some embodiments, $R^B$ is $C_6$ cycloalkyl. In some embodiments, $R^B$ is optionally substituted phenyl. In some embodiments, $R^B$ is optionally substituted $C_{2-9}$ heterocycloalkyl. In some embodiments, $R^B$ is $C_3$ heterocycloalkyl. In some embodiments, $R^B$ is $C_5$ heterocycloalkyl. In some embodiments, $R^B$ is $C_6$ heterocycloalkyl. In some embodiments, $R^B$ is optionally substituted 5-6 membered heterocycloalkyl or heteroaryl. In some embodiments, $R^B$ is optionally substituted monocyclic heteroaryl. In some embodiments, $R^B$ is optionally substituted bicyclic heteroaryl. In some embodiments, $R^B$ is imidazole, pyrazole, triazole, or tetrazole, each of which optionally substituted. In some embodiments, $R^B$ is imidazole. In some embodiments, $R^B$ is pyrazole. In some embodiments, $R^B$ is triazole. In some embodiments, $R^B$ is tetrazole.

In some embodiments of Formula (VI), $R^B$ is selected from:

71

72

73

In some embodiments of Formula (VI), $R^B$ is

In some embodiments, $R^B$ is

In some embodiments, $R^B$ is

In some embodiments, $R^B$ is

74

In some embodiments, $R^B$ is

In some embodiments, $R^B$ is

In some embodiments, $R^B$ is

In some embodiments of Formula (VI), ring C is a 5 membered heteroaryl, wherein the heteroaryl is optionally substituted. In some embodiments, ring C is optionally substituted 5 membered heteroaryl.

In some embodiments of Formula (VI), ring D is an aromatic, saturated or partially saturated 6 membered carbocycle or heterocycle, wherein each of the carbocycle or heterocycle is optionally substituted. In some embodiments, ring D is an optionally substituted aromatic 6 membered carbocycle. In some embodiments, ring D is an optionally substituted aromatic 6 membered heterocycle. In some embodiments, ring D is an optionally substituted saturated 6 membered carbocycle. In some embodiments, ring D is an optionally substituted saturated 6 membered heterocycle. In some embodiments, ring D is an optionally substituted partially saturated 6 membered carbocycle. In some embodiments, ring D is an optionally substituted partially saturated 6 membered heterocycle.

In some embodiments of Formula (VI), each of $R^8$ and $R^9$ is independently selected from hydrogen, halo, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl. In some embodiments of Formula (VI), each of $R^8$ and $R^9$ is independently selected from hydrogen, —CN, optionally substituted $C_{1-6}$ alkyl, optionally substituted $C_{1-6}$ heteroalkyl, optionally substituted $C_{2-6}$ alkenyl, and optionally substituted $C_{2-6}$ alkynyl. In some embodiments, $R^8$ is hydrogen. In some embodiments, $R^8$ is halo. In some embodiments, $R^8$ is —CN. In some embodiments, $R^8$ is optionally substituted $C_{1-6}$ alkyl. In some embodiments, $R^8$ is optionally substituted $C_{1-6}$ heteroalkyl. In some embodiments, $R^8$ is optionally substituted $C_{2-6}$ alkenyl. In some embodiments, $R^8$ is optionally substituted $C_{2-6}$ alkynyl. In some embodiments, $R^9$ is hydrogen. In some embodiments, $R^9$ is halo. In some embodiments, $R^9$ is —CN. In some embodiments, $R^9$ is optionally substituted $C_{1-6}$ alkyl. In some embodiments, $R^9$ is optionally substituted $C_{1-6}$ heteroalkyl. In some embodiments, $R^9$ is optionally substituted $C_{2-6}$ alkenyl. In some embodiments, $R^9$ is optionally substituted $C_{2-6}$ alkynyl. In some embodiments, $R^8$ and $R^9$ taken together form an oxo. In some embodiments, $R^8$ and $R^9$ taken together with the carbon to which they are attached form an optionally substituted 3-6 membered cycloalkyl or heterocycloalkyl.

In some embodiments of Formula (VI), ring A is phenyl, naphthyl, monocyclic heteroaryl, or bicyclic heteroaryl. In some embodiments, ring A is phenyl. In some embodiments, ring A is naphthyl. In some embodiments, ring A is monocyclic heteroaryl. In some embodiments, ring A is or bicyclic heteroaryl.

In some embodiments of Formula (VI), $R^A$ is independently selected from halogen, —$NO_2$, oxo, —CN, optionally substituted $C_{1-6}$ alkyl, optionally substituted $C_{2-6}$ alkenyl, optionally substituted $C_{2-7}$ alkynyl, optionally substituted $C_{1-6}$ heteroalkyl, optionally substituted $C_{3-8}$ cycloalkyl, optionally substituted $C_{2-7}$ heterocycloalkyl, —$OR^{11}$, —$SR^{11}$, —$N(R^{12})(R^{11})$, —$C(O)R^{12}$, —$C(O)OR^{12}$, —$OC(O)R^{12}$, —$OC(O)N(R^{12})(R^{11})$, —$C(O)N(R^{12})(R^{11})$, —$N(R^{12})C(O)R^{12}$, —$N(R^{12})C(O)OR^{12}$, —$N(R^{12})C(O)N(R^{12})(R^{11})$, —$N(R^{12})_2S(O)_2(R^{12})$, —$S(O)R^{12}$, —$S(O)_2R^{12}$, and —$S(O)_2N(R^{12})(R^{11})$. In some embodiments, $R^A$ is halogen. In some embodiments, $R^A$ is —$NO_2$. In some embodiments, $R^A$ is oxo. In some embodiments, $R^A$ is —CN. In some embodiments, $R^A$ is optionally substituted $C_{1-6}$ alkyl. In some embodiments, $R^A$ is optionally substituted $C_{1-3}$ alkyl. In some embodiments, $R^A$ is methyl, ethyl, propyl, iso-propyl, n-butyl, iso-butyl, sec-butyl, t-butyl, —$CF_3$, —$CH_2CF_3$, or —$CH_2CH_2F$. In some embodiments, $R^A$ is optionally substituted $C_{2-6}$ alkenyl. In some embodiments, $R^A$ is optionally substituted $C_{2-6}$ alkynyl. In some embodiments, $R^A$ is optionally substituted $C_{1-6}$ heteroalkyl. In some embodiments, $R^A$ is optionally substituted $C_{3-8}$ cycloalkyl. In some embodiments, $R^A$ is optionally substituted $C_{3-6}$ cycloalkyl, e.g., cyclopropyl. In some embodiments, $R^A$ is In some embodiments, $R^A$ is optionally substituted $C_{2-7}$ heterocycloalkyl. In some embodiments, $R^A$ is optionally substituted $C_{2-5}$ heterocycloalkyl. In some embodiments, $R^A$ is —$OR^{11}$. In some embodiments, $R^A$ is —O—$C_{1-3}$ alkyl. In some embodiments, $R^A$ is —$OCH_3$, —$OCH_2CH_3$, —$OCH_2OMe$, —$OCH_2CH_2OH$, —$OC(CH_3)_3$, or —$OCH_2CH_2OCH_3$. In some embodiments, $R^A$ is —$OCH_3$. In some embodiments, $R^A$ is In some embodiments, $R^A$ is —$SR^{11}$. In some embodiments, $R^A$ is —$N(R^{12})(R^{11})$. In some embodiments, $R^A$ is —$C(O)R^{12}$. In some embodiments, $R^A$ is —$C(O)OR^{12}$. In some embodiments, $R^A$ is —$OC(O)R^{12}$. In some embodiments, $R^A$ is —$OC(O)N(R^{12})(R^{11})$. In some embodiments, $R^A$ is —$C(O)N(R^{12})(R^{11})$. In some embodiments, $R^A$ is —$N(R^{12})C(O)R^{12}$. In some embodiments, $R^A$ is —$N(R^{12})C(O)OR^{12}$. In some embodiments, $R^A$ is —$N(R^{12})C(O)N(R^{12})(R^{11})$ In some embodiments, $R^A$ is —$N(R^{12})_2S(O)_2(R^{12})$. In some embodiments, $R^A$ is —$S(O)R^{12}$. In some embodiments, $R^A$ is —$S(O)_2R^{12}$. In some embodiments, $R^A$ is —$S(O)_2N(R^{12})(R^{11})$. In some embodiments, —$OCH_3$ is —$OCD_3$.

In some embodiments of Formula (VI), $R^{11}$ is hydrogen, optionally substituted $C_{1-6}$ alkyl, optionally substituted $C_{2-6}$ alkenyl, optionally substituted $C_{2-6}$ alkynyl, optionally substituted $C_{1-6}$ heteroalkyl, optionally substituted $C_{3-8}$ cycloalkyl, optionally substituted $C_{2-7}$ heterocycloalkyl, optionally substituted phenyl, optionally substituted heteroaryl, optionally substituted —$C_{1-4}$ alkylene-$C_{3-8}$ cycloalkyl, optionally substituted —$C_{1-4}$ alkylene-$C_{2-7}$ heterocycloalkyl, optionally substituted —$C_{1-4}$ alkylene-phenyl, or optionally substituted —$C_{1-4}$ alkylene-heteroaryl. In some embodiments, $R^{11}$ is hydrogen. In some embodiments, $R^{11}$ is optionally substituted $C_{1-6}$ alkyl. In some embodiments, $R^{11}$ is optionally substituted $C_{1-3}$ alkyl. In some embodiments, $R^A$ is methyl, ethyl, propyl, iso-propyl, n-butyl, iso-butyl, sec-butyl, t-butyl, —$CF_3$, —$CH_2CF_3$, or —$CH_2CH_2F$. In some embodiments, $R^{11}$ is optionally substituted $C_{2-6}$ alkenyl. In some embodiments, $R^{11}$ is optionally substituted $C_{2-6}$ alkynyl. In some embodiments, $R^{11}$ is optionally substituted $C_{1-6}$ heteroalkyl. In some embodiments, $R^{11}$ is optionally substituted $C_{3-8}$ cycloalkyl. In some embodiments, $R^{11}$ is optionally substituted $C_{2-7}$ heterocycloalkyl. In some embodiments, $R^{11}$ is optionally substituted phenyl. In some embodiments, $R^{11}$ is optionally substituted heteroaryl. In some embodiments, $R^{11}$ is optionally substituted —$C_{1-4}$ alkylene-$C_{3-8}$ cycloalkyl. In some embodiments, $R^{11}$ is optionally substituted —$C_{1-4}$ alkylene-$C_{2-7}$ heterocycloalkyl. In some embodiments, $R^{11}$ is optionally substituted —$C_{1-4}$ alkylene-phenyl. In some embodiments, $R^{11}$ is optionally substituted —$C_{1-4}$ alkylene-heteroaryl.

In some embodiments of Formula (VI), each of $R^{12}$ is independently selected from hydrogen, halogen, —OH, —$NO_2$, —CN, $C_{1-6}$ alkyl, $C_{1-6}$ aminoalkyl, $C_{1-6}$ hydroxyalkyl, $C_{1-6}$ haloalkyl, and $C_{3-6}$ carbocycle, 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, —CN, $C_{1-6}$ alkyl, $C_{1-6}$ alkoxy, and $C_{1-6}$ haloalkyl. In some embodiments of Formula (VI), each of $R^{12}$ is independently selected from hydrogen, —$NO_2$, —CN, $C_{1-6}$ alkyl, $C_{1-6}$ aminoalkyl, $C_{1-6}$ hydroxyalkyl, $C_{1-6}$ haloalkyl, and $C_{3-6}$ carbocycle, 3- to 6-membered heterocycle, wherein the $C_{3-6}$ carbocycle and 3- to 6-membered heterocycle is optionally substituted with one or more substituents independently selected from halogen, —OH, oxo, amino, —$NO_2$, —CN, $C_{1-6}$ alkyl, $C_{1-6}$ alkoxy, and $C_{1-6}$ haloalkyl. In some embodiments, $R^{12}$ is hydrogen. In some embodiments, $R^{12}$ is halogen. In some embodiments, $R^{12}$ is —OH. In some embodiments, $R^{12}$ is —$NO_2$. In some embodiments, $R^{12}$ is —CN. In some embodiments, $R^{12}$ is $C_{1-6}$ alkyl. In some embodiments, $R^{12}$ is $C_{1-6}$ aminoalkyl. In some embodiments, $R^{12}$ is $C_{1-6}$ hydroxyalkyl. In some embodiments, $R^{12}$ is $C_{1-6}$ haloalkyl. In some embodiments, $R^{12}$ is and $C_{3-6}$ carbocycle. In some embodiments, $R^{12}$ is 3- to 6-membered heterocycle, wherein the $C_{3-6}$ carbocycle and 3- to 6-membered heterocycle is optionally substituted with one or more substituents independently selected from halogen, —OH, oxo, amino, —NO$_2$, —CN, C$_{1-6}$ alkyl, C$_{1-6}$ alkoxy, and C$_{1-6}$ haloalkyl. In some embodiments, the one or more substituent is halogen. In some embodiments, the one or more substituent is —OH. In some embodiments, the one or more substituent is oxo. In some embodiments, the one or more substituent is amino. In some embodiments, the one or more substituent is —NO$_2$. In some embodiments, the one or more substituent is —CN. In some embodiments, the one or more substituent is C$_{1-6}$ alkyl. In some embodiments, the one or more substituent is C$_{1-6}$ alkoxy. In some embodiments, the one or more substituent is C$_{1-6}$ haloalkyl.

In some embodiments of Formula (VI), R$^B$ is hydrogen, halo, —CN, —NO$_2$, optionally substituted C$_{1-6}$ alkyl, optionally substituted C$_{2-6}$ alkenyl, optionally substituted C$_{2-6}$ alkynyl, optionally substituted C$_{1-6}$heteroalkyl, —OR$^{11}$, —SR$^{11}$, —N(R$^{12}$)(R$^{11}$), —C(O)R$^{12}$, —C(O)OR$^{12}$, —OC(O)R$^{12}$, —OC(O)N(R$^{12}$)(R$^{11}$), —C(O)N(R$^{12}$)(R$^{11}$), —N(R$^{12}$)C(O)R$^{12}$, —N(R$^{12}$)C(O)OR$^{12}$, —N(R$^{12}$)C(O)N (R$^{12}$)(R$^{11}$), —N(R$^{12}$)S(O)$_2$(R$^{12}$), —S(O)R$^{12}$, —S(O)$_2$R$^{12}$, —S(O)$_2$N(R$^{12}$)(R$^{11}$) optionally substituted C$_{3-8}$ cycloalkyl, optionally substituted C$_{2-9}$ heterocycloalkyl, optionally substituted naphthyl, optionally substituted phenyl, optionally substituted monocyclic heteroaryl, or optionally substituted bicyclic heteroaryl. In some embodiments, R$^B$ is hydrogen. In some embodiments, R$^B$ is halo. In some embodiments, R$^B$ is —CN. In some embodiments, R$^B$ is —NO$_2$. In some embodiments, R$^B$ is optionally substituted C$_{1-6}$ alkyl. In some embodiments, R$^B$ is optionally substituted C$_{2-6}$ alkenyl. In some embodiments, R$^B$ is optionally substituted C$_{2-6}$ alkynyl. In some embodiments, R$^B$ is optionally substituted C$_{1-6}$ heteroalkyl. In some embodiments, R$^B$ is —OR$^{11}$. In some embodiments, R$^B$ is —SR$^{11}$. In some embodiments, R$^B$ is —N(R$^{12}$)(R$^{11}$). In some embodiments, R$^B$ is —C(O)R$^{12}$. In some embodiments, R$^B$ is —C(O)OR$^{12}$. In some embodiments, R$^B$ is —OC(O)R$^{12}$. In some embodiments, R$^B$ is —OC(O)N(R$^{12}$)(R$^{11}$). In some embodiments, R$^B$ is —C(O)N(R$^{12}$)(R$^{11}$). In some embodiments, R$^B$ is —N(R$^{12}$)C(O)R$^{12}$. In some embodiments, R$^B$ is —N(R$^{12}$) C(O)OR$^{12}$. In some embodiments, R$^B$ is —N(R$^{12}$)C(O)N (R$^{12}$)(R$^{11}$) In some embodiments, R$^B$ is —N(R$^{12}$)S(O)$_2$ (R$^{12}$). In some embodiments, R$^B$ is —S(O)R$^{12}$. In some embodiments, R$^B$ is —S(O)$_2$R$^{12}$. In some embodiments, R$^B$ is —S(O)$_2$N(R$^{12}$)(R$^{11}$). In some embodiments, R$^B$ is optionally substituted C$_{3-8}$ cycloalkyl. In some embodiments, R$^B$ is optionally substituted C$_{2-9}$ heterocycloalkyl. In some embodiments, R$^B$ is optionally substituted naphthyl. In some embodiments, R$^B$ is optionally substituted phenyl. In some embodiments, R$^B$ is optionally substituted monocyclic heteroaryl. In some embodiments, R$^3$ is optionally substituted bicyclic heteroaryl.

In some embodiments of Formula (VI), m is 1, 2, 3, or 4. In some embodiments, m is 1. In some embodiments, m is 2. In some embodiments, m is 3. In some embodiments, m is 4.

In some embodiments of Formula (VI), p is 0 or 1. In some embodiments, p is 0. In some embodiments, p is 1.

Non-limiting examples of compounds described herein, are compounds presented in Table 1, and pharmaceutically acceptable salts or solvates thereof.

TABLE 1

Exemplary Compounds of the Disclosure

| Example No. | Structure |
| --- | --- |

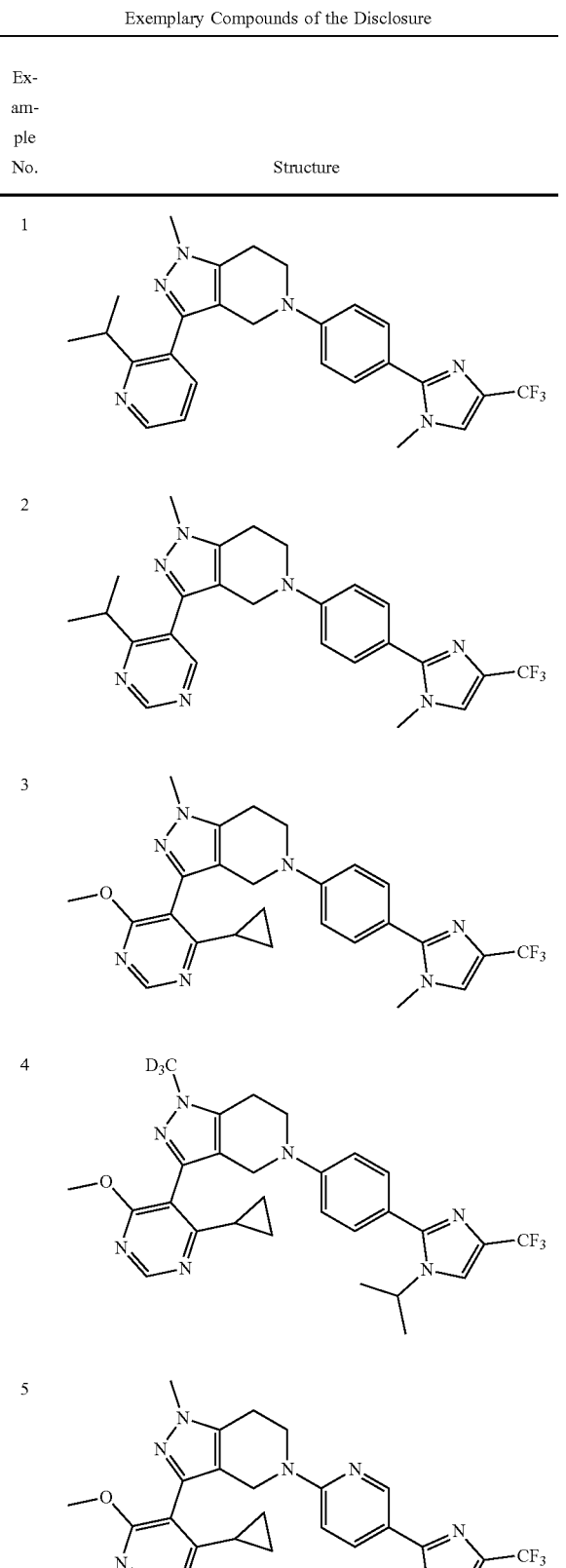

| 1 | |
| 2 | |
| 3 | |
| 4 | |
| 5 | |

TABLE 1-continued

Exemplary Compounds of the Disclosure

| Ex-am-ple No. | Structure |
|---|---|
| 6 | |
| 7 | |
| 8 | |
| 9 | |
| 10 | |

TABLE 1-continued

Exemplary Compounds of the Disclosure

| Ex-am-ple No. | Structure |
|---|---|
| 11 | |
| 12 | |
| 13 | |
| 14 | |
| 15 | |

TABLE 1-continued

| | Exemplary Compounds of the Disclosure |
| --- | --- |
| Ex-<br>am-<br>ple<br>No. | Structure |
| 16 | |
| 17 | |
| 18 | |
| 19 | |
| 20 | |

TABLE 1-continued

| | Exemplary Compounds of the Disclosure |
| --- | --- |
| Ex-<br>am-<br>ple<br>No. | Structure |
| 21 | |
| 22 | |
| 23 | |
| 24 | |
| 25 | |

TABLE 1-continued

Exemplary Compounds of the Disclosure

| Example No. | Structure |
|---|---|
| 26 | |
| 27 | |
| 28 | |
| 29 | |
| 30 | |

TABLE 1-continued

Exemplary Compounds of the Disclosure

| Example No. | Structure |
|---|---|
| 31 | |
| 32 | |

Table 2 presents corresponding biological data for USP1 IC50 (nM) and MDA-MB-436 IC50 (nM) for the compounds presented in Table 1.

TABLE 2

| Example No. | USP1 IC$_{50}$ (nM) | MDA-MB-436 IC$_{50}$ (nM) |
|---|---|---|
| 1 | A | A |
| 2 | B | B |
| 3 | A | A |
| 4 | A | A |
| 5 | A | A |
| 6 | A | A |
| 7 | A | A |
| 8 | A | A |
| 9 | A | A |
| 10 | A | A |
| 11 | A | A |
| 13 | B | B |
| 15 | A | B |
| 16 | B | B |
| 17 | A | A |
| 18 | A | A |
| 20 | B | B |
| 21 | C | — |
| 24 | A | B |
| 25 | A | A |
| 26 | B | B |
| 27 | A | A |
| 28 | A | A |
| 29 | B | B |
| 30 | A | A |
| 31 | A | B |
| 32 | A | B |

IC$_{50}$ (nm): $0 < A \leq 50$; $50 < B \leq 1,000$; $1,000 < C \leq 10,000$

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

Chemical entities having carbon-carbon double bonds or carbon-nitrogen double bonds can exist in Z- or E-form (or cis- or trans-form). Furthermore, some chemical entities can exist in various tautomeric forms. Unless otherwise specified, compounds described herein are intended to include all Z-, E- and tautomeric forms as well.

As used herein, "phenyl isostere" refers to a moiety or a functional group that exhibits similar physical, biological and/or chemical properties as a phenyl group. Exemplary phenyl isosteres include, without limitation, cubane, bicyclo [1.1.1]pentane (BCP), bicyclo[2.2.1]heptane, bicyclo[2.1.1] hexane, bicyclo[2.2.2]octane, adamantane, norbornene, closo-1,2-carborane, closo-1,7-carborane, closo-1,12-carbo-rane, and ethynyl group. In some embodiments, the phenyl isostere is cubane. In some embodiments, the phenyl isostere is an ethynyl group.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

Unless otherwise stated, compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, the compounds described herein may be artificially enriched in one or more particular isotopes. In some embodiments, the compounds described herein may be artificially enriched in one or more isotopes that are not predominantly found in nature. In some embodiments, the compounds described herein may be artificially enriched in one or more isotopes selected from deuterium ($^2$H), tritium ($^3$H), iodine-125 ($^{125}$I) or carbon-14 ($^{14}$C). In some embodiments, the compounds described herein are artificially enriched in one or more isotopes selected from $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$C, $^{79}$Br, $^{81}$Br, $^{131}$I, and $^{125}$I. In some embodiments, the abundance of the enriched isotopes is independently at least 1%, at least 10%, at least 20%, at least 30%, at least 40%, at least 50%, at least 60%, at least 70%, at least 80%, at least 90%, or 100% by molar.

In some embodiments of a compound disclosed herein, one or more of $R^1$, $R^4$, $R^{4'}$, $R^5$, $R^{5'}$, $R^6$, $R^{6'}$, $R^8$, $R^9$, $R^{Y1}$, $R^{Y2}$, $R^{Y3}$, $R^{Y4}$, $R^{11}$, $R^{12}$, $R^A$, $R^B$, $R^{B1}$, $R^{1Ca}$, $R^{1Da}$, $R^a$, $R^b$, $R^c$, and/or $R^d$ groups comprise deuterium at a percentage higher than the natural abundance of deuterium.

The compounds disclosed herein, in some embodiments, are used in different enriched isotopic forms, e.g., enriched in the content of $^2$H, $^3$H $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334, 997. As described in U.S. Pat. Nos. 5,846,514 and 6,334, 997, deuteration can improve the metabolic stability and or efficacy, thus increasing the duration of action of drugs.

In some embodiments of a compound disclosed herein, one or more $^1$H are replaced with one or more deuteriums in one or more of the following groups $R^1$, $R^4$, $R^{4'}$, $R^5$, $R^{5'}$, $R^6$, $R^{6'}$, $R^8$, $R^9$, $R^{Y1}$, $R^{Y2}$, $R^{Y3}$, $R^{Y4}$, $R^{11}$, $R^{12}$, $R^A$, $R^B$, $R^{B1}$, $R_{1Ca}$, $R^{1Da}$, $R^a$, $R^b$, $R^c$, and/or $R^d$.

In some embodiments of a compound disclosed herein, the abundance of deuterium in each of $R^1$, $R^4$, $R^{4'}$, $R^5$, $R^{5'}$, $R^6$, $R^{6'}$, $R^8$, $R^9$, $R^{Y1}$, $R^{Y2}$, $R^{Y3}$, $R^{Y4}$, $R^{11}$, $R^{12}$, $R^A$, $R^B$, $R^{B1}$, $R^{1Ca}$, $R^{1Da}$, $R^a$, $R^b$, $R^c$, and/or $R^d$ is independently at least 1%, at least 10%, at least 20%, at least 30%, at least 40%, at least 50%, at least 60%, at least 70%, at least 80%, at least 90%, or 100% by molar.

In some embodiments of a compound disclosed herein, one or more $^1$H of Ring A, Ring C, and/or Ring D are replaced with one or more deuteriums.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods. Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein can in some cases exist as diastereomers, enantiomers, or other stereoisomeric forms. Where absolute stereochemistry is not specified, the compounds presented herein include all diastereomeric, enantiomeric, and epimeric forms as well as the appropriate mixtures thereof. Separation of stereoisomers can be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers can also be obtained by stereoselective synthesis.

The methods and compositions described herein include the use of amorphous forms as well as crystalline forms (also known as polymorphs). The compounds described herein can be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds can be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure.

One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds can be a prodrug for another derivative or active compound.

Prodrugs are often useful because, in some situations, they can be easier to administer than the parent drug. They may, for instance, be bioavailable by oral administration whereas the parent is not. Prodrugs can help enhance the cell permeability of a compound relative to the parent drug. The prodrug can also have improved solubility in pharmaceutical compositions over the parent drug. Prodrugs can be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.,* 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., J. Pharm. Sci., 64:181-210 (1975); T. Higuchi and V. Stella, *Pro-drugs as Novel Delivery Systems,* Vol. 14 of the A.C.S. Symposium Series; and Edward B. Roche, *Bioreversible Carriers in Drug Design,* American Pharmaceutical Association and Pergamon Press, 1987, all incorporated herein for such disclosure). According to another embodiment, the present disclosure provides methods of producing the above-defined compounds. The compounds can be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

C. Pharmaceutical Compositions

Provided herein, in certain embodiments, are compositions comprising a therapeutically effective amount of any compound or salt of any one of Formulas (IVa), (IVa-1), (IVa-2), and (VI) (also referred to herein as "a pharmaceutical agent").

Pharmaceutical compositions can be formulated using one or more physiologically acceptable carriers including excipients and auxiliaries which facilitate processing of the pharmaceutical agent into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

The compositions and methods of the present disclosure can be utilized to treat an individual in need thereof. In certain embodiments, the individual is a mammal such as a human, or a non-human mammal. When administered to an animal, such as a human, the composition or the pharmaceutical agent, is preferably administered as a pharmaceutical composition comprising, for example, a pharmaceutical agent and a pharmaceutically acceptable carrier or excipient. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration, e.g., routes, such as injection or implantation, that circumvent transport or diffusion through an epithelial barrier, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule, granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable excipient can contain physiologically acceptable agents that act, for example, to stabilize, increase solubility or to increase the absorption of a compound such as a pharmaceutical agent. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable excipient, including a physiologically acceptable agent, depends, for example, on the route of administration of the composition. The preparation or pharmaceutical composition can be a self-emulsifying drug delivery system or a self microemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally, for example, drenches as in aqueous or non-aqueous solutions or suspensions, tablets, capsules, including sprinkle capsules and gelatin capsules, boluses, powders, granules, pastes for application to the tongue; absorption through the oral mucosa, e.g., sublingually; anally, rectally or vaginally, for example, as a pessary, cream or foam; parenterally, including intramuscularly, intravenously, subcutaneously or intrathecally as, for example, a sterile solution or suspension; nasally; intraperitoneally; subcutaneously; transdermally, for example, as a patch applied to the skin; and topically, for example, as a cream, ointment or spray applied to the skin, or as an eye drop. The compound can also be formulated for inhalation. In certain embodiments, a compound can be simply dissolved or suspended in sterile water.

A pharmaceutical composition can be a sterile aqueous or non-aqueous solution, suspension or emulsion, e.g., a microemulsion. The excipients described herein are examples and are in no way limiting. An effective amount or therapeutically effective amount refers to an amount of the one or more pharmaceutical agents administered to a subject, either as a single dose or as part of a series of doses, which is effective to produce a desired therapeutic effect.

Subjects can generally be monitored for therapeutic effectiveness using assays and methods suitable for the condition being treated, which assays will be familiar to those having ordinary skill in the art and are described herein. Pharmacokinetics of a pharmaceutical agent, or one or more metabolites thereof, that is administered to a subject can be monitored by determining the level of the pharmaceutical agent or metabolite in a biological fluid, for example, in the blood, blood fraction, e.g., serum, and/or in the urine, and/or other biological sample or biological tissue from the subject. Any method practiced in the art and described herein to detect the agent can be used to measure the level of the pharmaceutical agent or metabolite during a treatment course.

The dose of a pharmaceutical agent described herein for treating a disease or disorder can depend upon the subject's condition, that is, stage of the disease, severity of symptoms caused by the disease, general health status, as well as age, gender, and weight, and other factors apparent to a person skilled in the medical art. Pharmaceutical compositions can be administered in a manner appropriate to the disease to be treated as determined by persons skilled in the medical arts. In addition to the factors described herein and above related to use of pharmaceutical agent for treating a disease or disorder, suitable duration and frequency of administration of the pharmaceutical agent can also be determined or adjusted by such factors as the condition of the patient, the type and severity of the patient's disease, the particular form of the active ingredient, and the method of administration. Optimal doses of an agent can generally be determined using experimental models and/or clinical trials. The optimal dose can depend upon the body mass, weight, or blood volume of the subject. The use of the minimum dose that is sufficient to provide effective therapy is usually preferred. Design and execution of pre-clinical and clinical studies for a pharmaceutical agent, including when administered for prophylactic benefit, described herein are well within the skill of a person skilled in the relevant art. When two or more pharmaceutical agents are administered to treat a disease or disorder, the optimal dose of each pharmaceutical agent can be different, such as less than when either agent is administered alone as a single agent therapy. In certain particular embodiments, two pharmaceutical agents in combination can act synergistically or additively, and either agent can be used in a lesser amount than if administered alone. An amount of a pharmaceutical agent that can be administered per day can be, for example, between about 0.01 mg/kg and 100 mg/kg, e.g., between about 0.1 to 1 mg/kg, between about 1 to 10 mg/kg, between about 10-50 mg/kg, between about 50-100 mg/kg body weight. In other embodiments, the amount of a pharmaceutical agent that can be administered per day is between about 0.01 mg/kg and 1000 mg/kg, between about 100-500 mg/kg, or between about 500-1000 mg/kg body weight. The optimal dose, per day or per course of treatment, can be different for the disease or disorder to be treated and can also vary with the administrative route and therapeutic regimen.

Pharmaceutical compositions comprising a pharmaceutical agent can be formulated in a manner appropriate for the delivery method by using techniques routinely practiced in the art. The composition can be in the form of a solid, e.g., tablet, capsule, semi-solid, e.g., gel, liquid, or gas, e.g., aerosol. In other embodiments, the pharmaceutical composition is administered as a bolus infusion.

Pharmaceutical acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21$^{st}$ Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like can be provided in the pharmaceutical composition. In addition, antioxidants and suspending agents can also be used. In general, the type of excipient is selected based on the mode of administration, as well as the chemical composition of the active ingredient(s). Alternatively, compositions described herein can be formulated as a lyophilizate. A composition described herein can be lyophilized or otherwise formulated as a lyophilized product using one or more appropriate excipient solutions for solubilizing and/or diluting the pharmaceutical agent(s) of the composition upon administration. In other embodiments, the pharmaceutical agent can be encapsulated within liposomes using technology known and practiced in the art. In certain particular embodiments, a pharmaceutical agent is not formulated within liposomes for application to a stent that is used for treating highly, though not totally, occluded arteries. Pharmaceutical compositions can be formulated for any appropriate manner of administration described herein and, in the art.

A pharmaceutical composition, e.g., for oral administration or for injection, infusion, subcutaneous delivery, intramuscular delivery, intraperitoneal delivery or other method, can be in the form of a liquid. A liquid pharmaceutical composition can include, for example, one or more of the following: a sterile diluent such as water, saline solution, preferably physiological saline, Ringer's solution, isotonic sodium chloride, fixed oils that can serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition can be applied to the eye in the form of eye drops. A liquid pharmaceutical composition can be delivered orally.

For oral formulations, at least one of the pharmaceutical agents described herein can be used alone or in combination with appropriate additives to make tablets, powders, granules or capsules, and if desired, with diluents, buffering agents, moistening agents, preservatives, coloring agents, and flavoring agents. The pharmaceutical agents can be formulated with a buffering agent to provide for protection of the compound from low pH of the gastric environment and/or an enteric coating. A pharmaceutical agent included in a pharmaceutical composition can be formulated for oral delivery with a flavoring agent, e.g., in a liquid, solid or semi-solid formulation and/or with an enteric coating.

A pharmaceutical composition comprising any one of the pharmaceutical agents described herein can be formulated for sustained or slow release, also called timed release or controlled release. Such compositions can generally be prepared using well known technology and administered by, for example, oral, rectal, intradermal, or subcutaneous implantation, or by implantation at the desired target site. Sustained-release formulations can contain the compound dispersed in a carrier matrix and/or contained within a reservoir surrounded by a rate controlling membrane. Excipients for use within such formulations are biocompatible, and can also be biodegradable; preferably the formulation provides a relatively constant level of active component release. The amount of pharmaceutical agent contained within a sustained release formulation depends upon the site of implantation, the rate and expected duration of release, and the nature of the condition, disease or disorder to be treated or prevented.

In certain embodiments, the pharmaceutical compositions comprising a pharmaceutical agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated, e.g., intradermally or subcutaneously. The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a pharmaceutical agent can be formulated as emulsions for topical application. An emulsion contains one liquid distributed in the body of a second liquid. The emulsion can be an oil-in-water emulsion or a water-in-oil emulsion. Either or both of the oil phase and the aqueous phase can contain one or more surfactants, emulsifiers, emulsion stabilizers, buffers, and other excipients. The oil phase can contain other oily pharmaceutically approved excipients. Suitable surfactants include, but are not limited to, anionic surfactants, non-ionic surfactants, cationic surfactants, and amphoteric surfactants. Compositions for topical application can also include at least one suitable suspending agent, antioxidant, chelating agent, emollient, or humectant.

Ointments and creams may, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Liquid sprays can be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the pharmaceutical agent described herein can be formulated as in inhalant. Inhaled methods can deliver medication directly to the airway. The pharmaceutical agent can be formulated as aerosols, microspheres, liposomes, or nanoparticles. The pharmaceutical agent can be formulated with solvents, gases, nitrates, or any combinations thereof. Compositions described herein are optionally formulated for delivery as a liquid aerosol or inhalable dry powder. Liquid aerosol formulations are optionally nebulized predominantly into particle sizes that can be delivered to the terminal and respiratory bronchioles. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of aerosol particles having with a mass medium average diameter predominantly between 1 to 5μ. Further, the formulation preferably has balanced osmolarity ionic strength and chloride concentration, and the smallest aerosolizable volume able to deliver effective dose of the pharmaceutical agent. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, California), Sidestream® nebulizers (Medic-Aid Ltd., West Sussex, England), Pan LC® and Part LC Star® jet nebulizers (Part Respiratory Equipment, Inc., Richmond, Virginia), and Aerosonic™ (DeVilbiss Medizinische Produkte (Deutschland) GmbH, Heiden, Germany) and UltraAire® (Omron Healthcare, Inc., Vernon Hills, Illinois) ultrasonic nebulizers.

In some embodiments, the pharmaceutical agent(s) can be formulated with oleaginous bases or ointments to form a semisolid composition with a desired shape. In addition to the pharmaceutical agent, these semisolid compositions can contain dissolved and/or suspended bactericidal agents, preservatives and/or a buffer system. A petrolatum component that can be included can be any paraffin ranging in viscosity from mineral oil that incorporates isobutylene, colloidal silica, or stearate salts to paraffin waxes. Absorption bases can be used with an oleaginous system. Additives can include cholesterol, lanolin (lanolin derivatives, beeswax, fatty alcohols, wool wax alcohols, low HLB (hydrophobel-lipophobe balance) emulsifiers, and assorted ionic and non-ionic surfactants, singularly or in combination.

Controlled or sustained release transdermal or topical formulations can be achieved by the addition of time-release additives, such as polymeric structures, matrices, that are available in the art. For example, the compositions can be administered through use of hot-melt extrusion articles, such as bioadhesive hot-melt extruded film. The formulation can comprise a cross-linked polycarboxylic acid polymer formulation. A cross-linking agent can be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the pharmaceutical agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) can also comprise a water insoluble polymer. Rate controlling polymers can be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art can be used. By way of example, a sustained-release gel and the compound can be incorporated in a polymeric matrix, such as a hydrophobic polymer matrix. Examples of a polymeric matrix include a microparticle. The microparticles can be microspheres, and the core can be of a different material than the polymeric shell. Alternatively, the polymer can be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the pharmaceutical agent. The matrices can be formed by solvent evaporation, spray drying, solvent extraction and other methods known to those skilled in the art.

Kits with unit doses of one or more of the agents described herein, usually in oral or injectable doses, are provided. Such kits can include a container containing the unit dose, an informational package insert describing the use and attendant benefits of the drugs in treating disease, and optionally an appliance or device for delivery of the composition.

D. Methods of Treatment

Ubiquitin Specific Protease 1 (USP1) is a member of the ubiquitin-specific processing family of proteases. USP1 is a deubiquitinating enzyme ("DUB") and deubiquitinates its substrates involved in key oncogenic pathways to modulate their functions. Among its roles, USP1 can exhibit DNA-mediated activation at the replication fork, protects the fork, and promote survival in BRCA1-deficient cells. As loss of both USP1 and BRCA1 leads to replication fork degradation, inhibition of USP1 can selectively decrease the viability, or kill, tumor cells with defects in BRCA defects without affecting the survival of cells with normal BRCA function.

In the United States (US), it has been estimated that inherited BRCA1 and BRCA2 mutations are present in 5-10% of breast cancers and 10-15% of ovarian cancers. Breast cancer is the most common cancer in the world and the most common malignancy in women. BRCA1 and BRCA2 can be detected in at least 5% of unselected breast cancer patients and in approximately 30% of patients with a family history of developing breast or ovarian cancer. At present, treatment options including chemotherapy and immune checkpoint inhibitors are limited for breast cancer patients with germline BRCA mutations, more aggressive progression and higher risk of recurrence. While PARP inhibitors have been approved by the US Food and Drug Administration (FDA) as monotherapies for deleterious/ suspected deleterious germline BRCA-mutated, HER2-negative breast cancer, in some cases, resistance to the PARP inhibitors can be observed to develop quickly in breast cancer patients. Ovarian cancers represent a heterogenous group of solid tumors. On average, one in five ovarian cancer can be associated with germline mutations. Of those ovarian cancers with germline mutations, 65-85% can be associated with germline BRCA mutations. Similar to the breast cancer setting, while the PARP inhibitors can be the first-line maintenance therapy for patients with BRCA-mutated ovarian cancer, those patients can develop resistance to the PARP inhibitors.

The compounds described herein can be used as inhibitors of USP1. Such compounds can exhibit BRCA1 and/or BRCA2 mutant-selective, anti-proliferative activities. The compounds described herein can be used to treat BRCA1 and/or BRCA2 mutant or homologous recombination (HRD) positive cancers. The compounds described herein can exhibit anti-proliferative activities in cancer cells with a BRCA1 and/or BRCA2 mutation, particularly MDA-MB-436 cells. The compounds described herein may not exhibit similar anti-proliferative activities in cancer cells with wild-type BRCA, particularly SNG-M cells. In some embodiments, the compounds described herein can show selectivity for mutant BRCA1 and/or BRCA2 over wild-type BRCA of at least 50-fold, 100-fold, 150-fold, 200-fold, 250-fold, 300-fold, 350-fold, 400-fold, 450-fold, 500-fold, 550-fold, 600-fold, or more.

The compounds described herein can be used in the preparation of medicaments for the prevention or treatment of diseases or conditions. In some embodiments, the compounds described herein are used in a method of modulating USP1 in a subject. In some embodiments, the compounds described herein are used in a method of inhibiting USP1 in subject. In some embodiments, the compounds described herein are used in a method of inhibiting or reducing DNA repair activity modulated by USP1 in a subject. In some embodiments, the compounds herein are used in a method of treating a disease or disorder associated with USP1 in a subject. In some embodiments, the compounds described herein are used in a method of treating a disease or disorder associated with modulation of USP in a subject. In addition, a method for modulating, inhibiting, or treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity, course of the disease, disorder or condition, previous therapy, the patient's health status and response to the drugs, and the judgment of the treating physician.

In the case wherein the patient's condition does not improve, upon the doctor's discretion the administration of the compounds can be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose can conveniently be presented in a single dose or as divided doses administered simultaneously (or over a short period of time) or at appropriate intervals, for example as two, three, four or more sub-doses per day.

The pharmaceutical composition described herein can be in unit dosage forms suitable for single administration of precise dosages. In unit dosage form, the formulation is divided into unit doses containing appropriate quantities of one or more compound. The unit dosage can be in the form of a package containing discrete quantities of the formulation. Non-limiting examples are packaged tablets or capsules, and powders in vials or ampoules. Aqueous suspension compositions can be packaged in single-dose non-recloseable containers. Alternatively, multiple-dose recloseable containers can be used, in which case it is typical to include a preservative in the composition. By way of example only, formulations for parenteral injection can be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage can vary within this range depending upon the dosage form employed and the route of administration utilized.

In one aspect, the disclosure provides a method of modulating USP1 in a subject, comprising administering to the subject a compound described herein, or a pharmaceutically acceptable salt or solvate thereof.

In one aspect, the disclosure provides a method of inhibiting USP1 in a subject, comprising administering to the subject a compound described herein, or a pharmaceutically acceptable salt or solvate thereof.

In one aspect, the disclosure provides a method of inhibiting or reducing DNA repair activity modulated by USP1 in a subject in need thereof, the method comprising administering a therapeutically effective amount of a compound described herein, or a pharmaceutically acceptable salt or solvate thereof, or a pharmaceutical composition described herein.

In one aspect, the disclosure provides a method of treating a disease or disorder associated with USP1 in a subject in need thereof, comprising administering to the subject a therapeutically effective amount of a compound described herein, or a pharmaceutically acceptable salt or solvate thereof, or a pharmaceutical composition of described herein. In some embodiments, the disease or a disorder is cancer.

In one aspect, the disclosure provides a method of treating a disease or disorder associated with modulation of USP1 in a subject, comprising administering to the subject a therapeutically effective amount of a compound described herein, or a pharmaceutically acceptable salt or solvate thereof, or a pharmaceutical composition of described herein. In some embodiments, the disease or disorder is cancer.

In one aspect, the disclosure provides a method of treating cancer in a subject, comprising administering to the subject in need thereof an effective amount of a compound described herein, or a pharmaceutically acceptable salt or solvate thereof, or a pharmaceutical composition of described herein.

In some embodiments, administration of a compound described herein, or a pharmaceutically acceptable salt or solvate thereof can further comprise combination with other biologically active ingredients (e.g., a second therapeutic agent). Other biologically active ingredients can include a second and different antineoplastic agent or a second agent that targets a USP1 independent mechanism of DNA repair. In some embodiments, administration of a compound described herein, or a pharmaceutically acceptable salt or solvate thereof can further comprise combination with a non-drug therapy. Non-drug therapy can include surgery, radiation treatment, or any other type of therapy which does not include administering a drug. Such combination of the compounds described herein, or pharmaceutically acceptable salts or solvates thereof, with other biological active ingredients or non-drug therapies can enhance the effect of the compounds described herein, or pharmaceutically acceptable salts or solvates thereof. The compounds described herein can be administered simultaneously or sequentially to other biological active ingredients, but at least two or more compounds or biologically active ingredients can be administered during a single cycle or course of therapy. In some embodiments, the second therapeutic agent is a poly ADP-ribose polymerase (PARP) inhibitor. In some embodiments, a USP1 inhibitor described herein is administered with two PARP inhibitors. In some embodiments, the PARP inhibitor is olaparib, niraparib, talazoparib, or rucaparib.

In one aspect, the disclosure provides a method of treating cancer in a subject, comprising administering to the subject in need thereof an amount of a compound described herein, or a pharmaceutically acceptable salt or solvate thereof, or a pharmaceutical composition of described herein. In some embodiments, the cancer is leukemia, acute myeloid leukemia (AML), chronic myeloid leukemia, acute lymphoblastic leukemia (ALL), non-Hodgkin lymphoma (NHL), Hodgkin lymphoma (HL), or multiple myeloma (MM).

In some embodiments, the cancer is a carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, and combinations thereof. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma. In some embodiments, a cancer to be treated by the methods of the present disclosure is breast cancer. In some embodiments, a cancer to be treated by the methods of treatment of the present disclosure is triple negative breast cancer (TNBC). In some embodiments, a cancer to be treated by the methods of treatment of the present disclosure is ovarian cancer. In some embodiments, a cancer to be treated by the methods of treatment of the present disclosure is colorectal cancer. In some embodiments, the cancer is a homolgous-recombination deficient cancer. In some embodiments, the cancer comprises cancer cells with a mutation in a gene encoding p53.

In some embodiments, a patient or population of patients to be treated with a pharmaceutical composition of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a patient or population of patients to be treated with a pharmaceutical composition of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM"). In some embodiments, a patient or population of patients to be treated having the cancer selected from the group consisting of ovarian cancer, lung cancer and melanoma.

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; colorectal cancer, KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In one aspect, the disclosure provides a method of treating cancer in a subject, comprising administering to the subject in need thereof an effective amount of a compound described herein, or a pharmaceutically acceptable salt or solvate thereof, or a pharmaceutical composition of described herein. In some embodiments, the cancer can comprise cancer cells with elevated levels of RAD 18 mRNA expression. In some embodiments, elevated levels of RAD 18 are elevated levels of RAD 18 protein. In some embodiments, RAD 18 levels can be detected using quantitative methods like microarray, RNA-Seq, or reverse transcriptase polymerase chain reaction (RT-PCR). In some embodiments, the levels of RAD 18 in a cancer cell can be detected prior to administration of the compounds described herein. In some embodiments, RAD 18 levels can be detected in a cancer sample obtained from a subject. In some embodiments, if a subject has elevated levels of RAD 18, the subject can be treated with the compounds described herein. In some embodiments, elevated levels of RAD 18 in cancer cells indicate that a subject administered the compounds or pharmaceutical compositions described herein is responsive to treatment using the compounds or pharmaceutical compositions described herein. In some embodiments, the compounds described herein are not administered to a subject with elevated levels of RAD 18.

In some embodiments, the cancer is a DNA damage repair pathway deficient cancer. In some embodiments, the cancer is a PARP inhibitor resistant or refractory BRCA1 or BRCA2-mutant cancer. In some embodiments, the cancer comprises cells with elevated levels of RAD 18, where the elevated levels of RAD 18 are at least as high as the RAD 18 mRNA and/or protein levels in ES2 cells or HEP3B217 cells.

In some embodiments, the cancer is a BRCA1 mutant cancer and/or a BRCA2 mutant cancer. In some embodiments, the cancer is a BRCA1 or BRCA2 wildtype cancer. In some embodiments, the cancer is a BRCA1-deficient cancer. In some embodiments, the cancer is a BRCA2-deficient cancer. In some embodiments, the cancer that comprises cancer cells with a mutation in a gene that encodes BRCA1 and/or BRCA2. In some embodiments, the cancer is a BRCA1 mutant cancer and BRCA2 deficient cancer. In some embodiments, the cancer is a BRCA1 deficient cancer and BRCA2 mutant cancer. In some embodiments, the cancer comprises cells with elevated levels of RAD 18, where the elevated levels of RAD 18 are at least as high as the RAD 18 mRNA and/or protein levels in ES2 cells or HEP3B217 cells.

EXAMPLES

The following examples are offered to illustrate, but not to limit the claimed disclosure. The following examples further illustrate the disclosure but, of course, should not be construed as in any way limiting its scope.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

The compounds and salts of Formulas (IVa), (IVa-1), (IVa-2), and (VI) can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in the synthesis schemes below, the steps in some cases can be performed in a different order than the order shown below. Numberings or R groups in each scheme do not necessarily correspond to that of the claims or other schemes or tables herein.

Examples A _ Biological Assays

Example A1: Enzymatic Assay

Human recombinant USP1/UAF1 expressed in baculovirus infected Sf21 cells were used (R&D, E-568-050). Test compound and/or vehicle was incubated with 2 nM of USP1/UAF1 in modified HEPES buffer pH 8.0 for 15 minutes at RT. The reaction was initiated by addition of 500 nM of Ubiquitin Rhodamine 110 (R&D, U-555-050) for kinetic reading. Slope change of fluorescence intensity was read spectrofluorimetric ally at 485 nm/535 nm. Dose response of test compounds or reference compound ML-323 was analyzed by nonlinear regression of GraphPad prism software. Results of the assay are illustrated in Table 2.

Example A2: MDA-MB-436 Breast Cancer Cell Culture

MDA-MB-436 cells were grown in Leibovitz's L-15 medium with 10 ug/ml insulin, 16 ug/ml glutathione, 10% FBS. Cells were passaged at subconfluence after trypsinization and maintained in incubators at 37° C. in a humidified atmosphere with 5% $CO_2$.

Example A3: MDA-MB-436 Breast Cancer Cell Proliferation Assay

Cell proliferation was determined using CellTiter-Glo® Luminescent Cell Viability Assay (Promega, #G7573). MDA-MB-436 cells were seeded in 384-well plates and allowed to attach for 24 h. Compounds were added into 384-well plate by ECHO, and incubated at 37° C. in a humidified atmosphere with 5% $CO_2$. After 7 days, CellTiter-Glo was added into 384 well plates, contents were mixed on an orbital shaker at 400 g for 2 min before centrifuging the plate for 2 min at 1000 rpm. After incubation at RT for 30 min, luminescence was read on envision. Results of the assay are illustrated in Table 2.

Examples B _ Chemical Synthesis

Example B1: LCMS Method

The LCMS methods used in the following synthesis procedures are provided in Table 3.

TABLE 3

| | LCMS Method codes (Flow expressed in mL/min; column temperature (T) in ° C.; Run time in minutes). | | | | | | |
|---|---|---|---|---|---|---|---|
| | | | | | | Flow — | |
| Method code | Instrument | Column | Mobile phase | Gradient | Column T | Run time |
|---|---|---|---|---|---|---|
| Method A | Shimadzu: LC-MS2020-SPD-M20A and Alltech 3300ELSD | SunFire C18 5 μm 50*4.6 mm | A FA 0.1% in water, B: FA 0.1% in CH₃CN | 70% A for 0.4 min, to 5% A in 1.6 min, 5% A for 0.6 min | 2.0 mL/min — 40° C. | 2.6 min |

TABLE 3-continued

| | | | | | Flow | | |
|---|---|---|---|---|---|---|---|
| | | LCMS Method codes | | | | | |
| | | (Flow expressed in mL/min; column temperature (T) in ° C.; Run time in minutes). | | | | | |
| Method code | Instrument | Column | Mobile phase | Gradient | Column T | Run time |
| Method B | Shimadzu: LC-MS2020-SPD-M20A and Alltech 3300ELSD | SunFire C18 5 μm 50*4.6 mm | A FA 0.1% in water, B: FA 0.1% in CH₃CN | 50% A for 0.4 min, to 5% A in 1.6 min, 5% A for 0.6 min | 2.0 mL/min — 40° C. | 2.6 min |

Example B2: Synthesis of Intermediate A

Intermediate A-1

Intermediate A-2

Intermediate A 4-cyclopropyl-6-methoxypyrimidine

To a solution of 4-chloro-6-methoxypyrimidine (150.00 g, 1.04 mol) in dioxane (1500 mL) and H₂O (300 mL) were added cyclopropylboronic acid (178.27 g, 2.08 mol), K₂CO₃ (286.82 g, 2.08 mol) and Pd(dppf)Cl₂ (75.92 g, 0.10 mol). The reaction was stirred at 100° C. for 16 h under Ar atmosphere. The mixture was diluted with water (500 mL) and extracted with EtOAc (400 mL×3). The combined organic layers were washed with brine (500 mL), dried over Na₂SO₄, filtered and concentrated. The residue was purified by column chromatography on silica gel eluted with PE/EtOAc=20/1 to afford desired product (82.10 g, 0.55 mol, 53%) as a yellow oil.

LCMS: Retention time: 1.157 min, (M+H)⁺=151.1, method A.

5-bromo-4-cyclopropyl-6-methoxypyrimidine

To a solution of 4-cyclopropyl-6-methoxypyrimidine (82.00 g, 546.01 mmol) in EtOH (900 mL) was added Br₂ (30.85 mL, 600.61 mmol) at 0° C. The reaction mixture was stirred at room temperature for 16 h. The suspension was filtered and washed with MeOH (200 mL). The solid was dried to afford desired product (99.70 g, 435.22 mmol, 79.7%) as a white solid.

LCMS: Retention time: 1.707 min, (M+H)⁺=229.1, method A.

4-cyclopropyl-6-methoxy-5-(4,4,5,5-tetramethyl-1,3,
2-dioxaborolan-2-yl)pyrimidine To a solution of 5-bromo-4-cyclopropyl-6-methoxypy-rimidine (50.00 g, 218.26 mmol) in DMSO (500 mL) were added 4,4,5,5-tetramethyl-2-(tetramethyl-1,3,2-dioxaboro-lan-2-yl)-1,3,2-dioxaborolane (110.88 g, 436.53 mmol), KOAc (64.26 g, 654.79 mmol) and Pd(dppf)Cl₂ (15.97 g, 21.83 mmol). The reaction was stirred at 100° C. for 16 h under Ar atmosphere. The mixture was diluted with 600 mL of water and extracted with EtOAc (500 mL×3). The combined organic layers were washed with brine (200 mL×3), dried over Na₂SO₄, filtered and concentrated under vacuum. The residue was purified by column chromatography on silica gel eluted with PE/EtOAc=10:1 to afford desired product (28.00 g, 101.40 mmol, 46%) as a white solid.

LCMS: Retention time: 1.627 min, (M+H)⁺=277.2, method A.

¹H NMR (400 MHz, DMSO-d₆): δ=8.59 (s, 1H), 3.86 (s, 3H), 2.05-2.02 (m, 1H), 1.32 (s, 12H), 1.04-1.00 (m, 4H).

Example B3: Synthesis of Intermediate B

-continued

Intermediate B

-continued

Intermediate C

2-isopropylpyridin-3-yl trifluoromethanesulfonate

To a solution of 2-isopropylpyridin-3-ol (4.50 g, 32.80 mmol) in pyridine (20 mL) was added trifluoromethanesulfonic anhydride (5.44 mL, 32.80 mmol) at 0° C. The mixture was stirred rt for 2 h. The mixture was quenched with ice-water (30 mL) and basified with sat. NaHCO$_3$ solution till pH=7. The mixture was extracted with DCM (20 mL×3). The combined organic fractions were washed with brine (30 mL), dried over Na$_2$SO$_4$, filtered and concentrated under reduced pressure. The residue was purified by column chromatography on silica gel (eluting with PE/EtOAc from 50/1 to 20/1) to give desired product (7.88 g, 29.30 mmol, 89.3%) as a pale yellow oil. LCMS confirmed.

LCMS: Retention time: 1.597 min, (M+H)$^+$=270.0, method A.

2-isopropyl-3-(4,4,5,5-tetramethyl-1,3,2-dioxaboro-lan-2-yl)pyridine

A mixture of 2-isopropylpyridin-3-yl trifluoromethanesulfonate (5.88 g, 21.84 mmol), B$_2$pin$_2$ (11.09 g, 43.66 mmol), potassium acetate (4.28 g, 43.66 mmol) and Pd(dppf)Cl$_2$ (1.60 g, 2.18 mmol) in dioxane (50 mL) was stirred at 95° C. for 5 h under Ar. The mixture was concentrated, and the residue was purified by column chromatography on silica gel (eluting with DCM/MeOH from 100/1 to 40/1) to give desired product (5.20 g, 21.04 mmol, 96%) as a brown oil.

LCMS: Retention time: 0.360 min, (M+H)$^+$=166.1 (MS of corresponding boronic acid), method A.

Example B4: Synthesis of Intermediate C

Intermediate C-1

2-(4-bromophenyl)-4-(trifluoromethyl)-1H-imidazole

To a solution of 3, 3-dibromo-1, 1, 1-trifluoropropan-2-one (17.5 g, 64.86 mmol) in H$_2$O (30 mL) was added NaOAc (8.87 g, 108.10 mmol). The mixture was stirred at 100° C. for 1 h and then cooled to room temperature. A mixture of 4-bromobenzaldehyde (7.05 g, 38.1 mmol), NH$_4$OH (27.75 mL, 216.19 mmol) and MeOH (50 mL) was added. The resulting mixture was stirred at room temperature for 16 h. Then the reaction mixture was concentrated under reduced pressure. The precipitate was collected by filtration and washed with ethyl acetate/petroleum ether (1/5, 60 mL). The solids were collected and dried under vacuum to give desired product (6.00 g, 20.6 mmol, 54%) as a yellow solid.

LCMS: Retention time: 1.267 min, (M+H)$^+$=290.9, method B.

2-(4-bromophenyl)-1-methyl-4-(trifluoromethyl)-1H-imidazole

To a solution of 2-(4-bromophenyl)-4-(trifluoromethyl)-1H-imidazole (6.00 g, 20.61 mmol) in DMF (100 mL) was added NaH (1.65 g, 41.22 mmol, 60% dispersion in mineral oil) at 0° C. After stirred at 0° C. for 0.5 h, CH$_3$I (3.51 g, 24.73 mmol) was added. The mixture was stirred at rt for 16 h. Then the mixture was diluted with water (80 mL) and extracted with EtOAc (70 mL×3). The combined organic fractions were washed with brine (80 mL), dried over Na$_2$SO$_4$, filtered and concentrated under reduced pressure. The residue was purified by column chromatography on silica gel (eluting with PE/EtOAc from 100/1 to 20/1) to give desired product (2.81 g, 9.21 mmol, 45%) as a yellow solid. NMR confirmed.

H NMR: (400 MHz, CDCl$_3$) δ=7.63-7.60 (m, 2H), 7.53-7.50 (m, 2H), 7.31 (d, J=0.8 Hz, 1H), 3.76 (s, 3H)

Example B5: Synthesis of Intermediate D

Intermediate D-1

-continued

Intermediate A

Pd(dppf)Cl$_2$, Na$_2$CO$_3$,
Dioxane/H$_2$O, 100° C., 6 h

Intermediate D-2

TFA
DCM, rt, 2 h

Intermediate D-3

Intermediate D tert-butyl 3-iodo-1,4,6,7-tetrahydro-5H-pyrazolo[4,3-c]pyridine-5-carboxylate To a solution of tert-butyl 1,4,6,7-tetrahydro-5H-pyrazolo[4,3-c]pyridine-5-carboxylate (50.00 g, 223.93 mmol) in DMF (800 mL) were added I$_2$ (113.67 g, 447.87 mmol) and KOH (50.26 g, 895.74 mmol) at 0° C. The resulting mixture was stirred at 60° C. for 16 h. Then the reaction mixture was cooled to rt, quenched with aq. Na$_2$SO$_3$ (100 mL) and water (1500 mL) and then extracted with EtOAc (350 mL×6). The combined organic layer was washed with brine (300 mL×5), dried over Na$_2$SO$_4$, filtered and concentrated under reduced pressure. The residue was recrystallized from Et$_2$O (200 mL) to give desired product (32.50 g, 93.07 mmol, 42%) as a white solid.

$^1$H NMR (400 MHz, DMSO-d6) δ=12.98 (s, 1H), 4.11 (s, 2H), 3.58 (t, J 5.6 Hz, 2H), 2.63 (s, 2H), 1.42 (s, 9H)

tert-butyl 3-iodo-1-methyl-1,4,6,7-tetrahydro-5H-pyrazolo[4,3-c]pyridine-5-carboxylate To a solution of tert-butyl 3-iodo-1,4,6,7-tetrahydro-5H-pyrazolo[4,3-c]pyridine-5-carboxylate (625 mg, 1.79 mmol) in DMF (10 mL) were added Cs$_2$CO$_3$ (1750 mg, 5.37 mmol)

and CH$_3$I (0.17 mL, 2.68 mmol) at room temperature. The reaction mixture was stirred at rt for 16 h. The mixture was diluted with water (20 mL) and extracted with EtOAc (30 mL×3). The combined organic layers were washed with brine (10 mL×3), dried over Na$_2$SO$_4$, filtered and concentrated under vacuum to afford desired product (630 mg, 1.73 mmol, crude yield 97%) as a yellow oil.

LCMS: Retention time: 1.825 min, (M+H)$^+$=364.1, method A.

Separation of two N-methylation isomers by column chromatography on silica gel eluted with ethyl acetate (from 0% to 10%) in petroleum ether gave pure product (350 mg, 0.96 mmol, 54%). $^1$H NMR (400 MHz, DMSO-d$_6$) δ=4.10 (s, 2H), 3.69 (s, 3H), 3.59 (t, J=5.8 Hz, 2H), 2.64 (t, J=5.6 Hz, 2H), 1.42 (s, 9H).

tert-butyl 3-(4-cyclopropyl-6-methoxypyrimidin-5-yl)-1-methyl-1,4,6,7-tetrahydro-5H-pyrazolo[4,3-c]pyridine-5-carboxylate To a solution of tert-butyl 3-iodo-1-methyl-1,4,6,7-tetrahydro-5H-pyrazolo[4,3-c]pyridine-5-carboxylate (200 mg, 0.55 mmol) in dioxane (5 mL) and H$_2$O (1 mL) were added 4-cyclopropyl-6-methoxy-5-(4,4,5,5-tetramethyl-1,3,2-dioxaborolan-2-yl)pyrimidine (152 mg, 0.55 mmol), Pd(dppf)Cl$_2$ (40 mg, 0.06 mmol) and Na$_2$CO$_3$ (117 mg, 1.10 mmol). The mixture was stirred at 100° C. for 6 h. The mixture was cooled to rt, diluted with water (15 mL) and extracted with EtOAc (15 mL×3). The combined organic phases were washed with brine (15 mL), dried over Na$_2$SO$_4$, filtered and concentrated under vacuum. The residue was purified by column chromatography on silica gel (eluting with PE/EtOAc from 100/0 to 5/1) to afford desired product (50 mg, 0.13 mmol, 24%) as a white solid.

LCMS: Retention time: 1.667 min, (M+H)$^+$=386.3, method A.

$^1$H NMR (400 MHz, CDCl$_3$) δ=8.59 (s, 1H), 4.27 (s, 2H), 3.96 (s, 3H), 3.82 (s, 3H), 3.80-3.72 (m, 2H), 2.74 (t, J=5.6 Hz, 2H), 2.16-2.06 (m, 1H), 1.46 (s, 9H), 1.23-1.16 (m, 2H), 0.99-0.92 (m, 2H).

3-(4-cyclopropyl-6-methoxypyrimidin-5-yl)-1-methyl-4,5,6,7-tetrahydro-1H-pyrazolo[4,3-c]pyridine The solution of tert-butyl 3-(4-cyclopropyl-6-methoxypyrimidin-5-yl)-1-methyl-1,4,6,7-tetrahydro-5H-pyrazolo[4,3-c]pyridine-5-carboxylate (50 mg, 0.13 mmol) in TFA (5 mL) and DCM (15 mL) was stirred at rt for 2 h. The mixture was concentrated and dissolved in MeOH (10 mL). Sat. aqueous NaHCO$_3$ (15 mL) was added till pH=8. The mixture was concentrated and purified by reverse column chromatography (H$_2$O/CH$_3$CN from 100/0 to 4:1) to afford desired product (20 mg, 0.07 mmol, 54%) as a white solid.

LCMS: Retention time: 0.380 min, (M+H)$^+$=286.2, method A.

$^1$H NMR (400 MHz, CDCl$_3$) δ=10.01 (s, 1H), 8.58 (s, 1H), 4.03 (s, 2H), 3.93 (s, 3H), 3.85 (s, 3H), 3.52 (t, J=6.0 Hz, 2H), 3.06 (t, J=5.8 Hz, 2H), 2.19-2.11 (m, 1H), 1.21-1.13 (m, 2H), 1.00-0.91 (m, 2H).

Example B6: Synthesis of Compound 1

Intermediate D-2

Intermediate B

Pd(dppf)Cl$_2$, Na$_2$CO$_3$
Dioxane, H$_2$O, 100° C., 4 h

HCl/MeOH
rt, 16 h

Intermediate C

PEPPSI——IPr, t-BuONa,
Toluene, 100° C., 16 h

Compound 1 tert-butyl 3-(2-isopropylpyridin-3-yl)-1-methyl-1,4,6,7-tetrahydro-5H-pyrazolo[4,3c]pyridine-5-carboxylate To a solution of tert-butyl 3-iodo-1-methyl-1,4,6,7-tetrahydro-5H-pyrazolo[4,3-c]pyridine-5-carboxylate (600 mg, 1.65 mmol) in dioxane (2 mL) and H$_2$O (0.4 mL) were added 2-(propan-2-yl)-3-(tetramethyl-1,3,2-dioxaborolan-2-yl) pyridine (612 mg, 2.48 mmol), Na$_2$CO$_3$ (70 mg, 0.66 mmol) and Pd(dppf)Cl$_2$ (16 mg, 0.02 mmol). The reaction mixture was stirred at 100° C. for 4 h under nitrogen atmosphere. The mixture was cooled to rt, quenched with 60 mL of water and extracted with EtOAc (60 mL×2). The combined organic layers were washed with brine (50 mL×2), dried over Na$_2$SO$_4$, filtered and concentrated under vacuum. The residue was purified by column chromatography on silica gel eluted with PE/EtOAc=3/2 to afford desired product (350 mg, 0.98 mmol, 59%) as a yellow solid.

LCMS: Retention time: 1.220 min, (M+H)$^+$=357.2, method A.

3-(2-isopropylpyridin-3-yl)-1-methyl-4,5,6,7-tetrahydro-1H-pyrazolo[4,3-c]pyridine To a solution of tert-butyl 3-(2-isopropylpyridin-3-yl)-1-methyl-1,4,6,7-tetrahydro-5H-pyrazolo[4,3-c]pyridine-5-carboxylate (40 mg, 0.112 mmol) in methanol (5 mL) was added methanol hydrochloric acid (0.21 mL, 3M) slowly. The mixture was stirred at room temperature for 16 h. The pH value of reaction mixture was adjusted to 8-9 with NaHCO$_3$. The resulting suspension was filtered, and the filtrate was concentrated to give the crude product. The crude product was purified by C18 column chromatography (H$_2$O/CH$_3$CN from 100/1 to 30/70) to afford the desired product (25 mg, 0.098 mmol, 87%) as a colorless oil.

LCMS: Retention time: 0.267 min, (M+H)$^+$=257.1, method A.

3-(2-isopropylpyridin-3-yl)-1-methyl-5-(4-(1-methyl-4-(trifluoromethyl)-1H-imidazol-2-yl)phenyl)-4,5,6,7-tetrahydro-1H-pyrazolo[4,3-c]pyridine To a mixture of 3-(2-isopropylpyridin-3-yl)-1-methyl-4,5,6,7-tetrahydro-1H-pyrazolo[4,3-c]pyridine (30 mg, 0.12 mmol), 2-(4-bromophenyl)-1-methyl-4-(trifluoromethyl)-1H-imidazole (36 mg, 0.12 mmol) and t-BuONa (23 mg, 0.23 mmol) in toluene (10 mL) was added PEPPSI-IPr (2.8 mg, 0.003 mmol). The mixture was stirred at 100° C. for 16 h under N$_2$ atmosphere and then cooled to room temperature. The mixture was diluted with water (20 mL) and extracted with EtOAc (30 mL×3). The organic layer was dried with Na$_2$SO$_4$, filtered and concentrated to give a crude product. The crude product was purified by prep-TLC (PE/EtOAc=3/2) to afford desired product (4.80 mg, 0.01 mmol, 8%).

LCMS: Retention time: 1.157 min, (M+H)$^+$=481.2, method A.

$^1$H NMR: (400 MHz, DMSO-d$_6$) δ=8.57 (dd, J=4.8 Hz, J=1.6 Hz, 1H), 7.84 (s, 1H), 7.64 (dd, J=7.6 Hz, J=1.6 Hz, 1H), 7.53 (d, J=8.8 Hz, 2H), 7.29 (dd, J=7.6 Hz, J=4.4 Hz, 1H), 7.06 (d, J=8.8 Hz, 2H), 4.21 (s, 2H), 3.79-3.77 (m, 5H), 3.74 (s, 3H), 3.46-3.42 (m, 1H), 2.88 (t, J=5.2 Hz, 2H), 1.17 (d, J=6.8 Hz, 6H).

Example B7: Synthesis of Compound 2

K$_2$S$_2$O$_8$, AgNO$_3$
DCM/H$_2$O, r.t., 18 h

B2pin2, Pd(dppf)Cl$_2$, KOAc
toluene, DME, EtOH, H$_2$O
90° C., MW, 0.5 h

-continued

Intermediate D-2

Pd(dppf)Cl₂, Na₂CO₃
Dioxane, H₂O, 80° C., 1 h

TFA/DCM
rt, 2 h

Intermediate C

Pd₂(dba)₃, t-Bu XPhos, t-BuONa,
dioxane, 100° C., 16 h

Compound 2

5-bromo-4-isopropylpyrimidine

To a mixture of 5-bromopyrimidine (5.00 g, 31.45 mmol), isobutyric acid (3.325 g, 37.74 mmol), silver nitrate (2.67 g, 15.72 mmol) and potassium persulfate (10.2 g, 37.74 mmol) was added DCM (50 mL) and water (50 mL) at 0° C. The mixture was stirred at rt for 18 h. The solvent was evaporated. The residue was diluted with EtOAc (60 mL), washed with brine (60 mL), and dried over anhydrous Na₂SO₄. Evaporation of the solvent followed by purification on silica gel column chromatography (eluting with PE/EtOAc from I/O to 80/1) gave desired product (1.30 g, 6.47 mmol, 21% yield) as a colorless oil.

$^1$H NMR (400 MHz, CDCl₃) δ 9.03 (s, 1H), 8.71 (s, 1H), 3.50-3.46 (m, 1H), 1.30-1.27 (m, 6H)

4-isopropyl-5-(4,4,5,5-tetramethyl-1,3,2-dioxaborolan-2-yl)pyrimidine

A mixture of 5-bromo-4-isopropylpyrimidine (350 mg, 1.74 mmol), 4,4,5,5-tetramethyl-2-(tetramethyl-1,3,2-dioxaborolan-2-yl)-1,3,2-dioxaborolane (442 mg, 1.74 mmol), Pd(dppf)Cl₂ (127 mg, 0.17 mmol) and KOAc (171 mg, 1.74 mmol) in toluene (2.25 mL)/DME (1.5 mL)/EtOH (1.5 mL)/H₂O (0.75 mL) was heated at 90° C. using microwave under Ar for 0.5 h. The mixture was used without work up in the next step.

LCMS: Retention time: 1.497 min, (M+H)$^+$=249.2, method B.

tert-butyl 3-(4-isopropylpyrimidin-5-yl)-1-methyl-1,4,6,7-tetrahydro-5H-pyrazolo[4,3-c]pyridine-5-carboxylate A mixture of 4-isopropyl-5-(4,4,5,5-tetramethyl-1,3,2-dioxaborolan-2-yl)pyrimidine (120 mg, 0.48 mmol), tert-butyl 3-iodo-1-methyl-1H,4H,5H,6H,7H-pyrazolo[4,3-c]pyridine-5-carboxylate (176 mg, 0.48 mmol), Pd(dppf)Cl₂ (35 mg, 0.05 mmol) and Na₂CO₃ (103 mg, 0.97 mmol) in dioxane (5 mL) and H₂O (1 mL) was heated and stirred at 80° C. using microwave under Ar for 1 h. The mixture was diluted with water (10 mL) and extracted with EtOAc (10 mL×3). The combined organic phases were washed with brine (10 mL), dried over Na₂SO₄, filtered and concentrated under reduced pressure. The residue was purified by prep-TLC (PE/EtOAc=5/1) to give desired product (68 mg, 0.19 mmol, 39%) as a yellow oil.

LCMS: Retention time: 1.207 min, (M+H)$^+$=358.2, method B.

3-(4-isopropylpyrimidin-5-yl)-1-methyl-4,5,6,7-tetrahydro-1H-pyrazolo[4,3-c]pyridine A solution of tert-butyl 3-(4-isopropylpyrimidin-5-yl)-1-methyl-1,4,6,7-tetrahydro-5H-pyrazolo[4,3-c]pyridine-5-carboxylate (96 mg, 0.27 mmol) in TFA (1 mL) and DCM (2 mL) was stirred at rt for 2 h. The pH of mixture was adjusted to 8.0 with 8 N NH₃/MeOH and concentrated under reduced pressure. The residue was purified by prep-TLC (DCM/MeOH=10/1) to give desired product (60 mg, 0.23 mmol, 86.82%) as a white solid.

LCMS: Retention time: 0.607 min, (M+H)$^+$=258.2, method A.

3-(4-isopropylpyrimidin-5-yl)-1-methyl-5-(4-(1-methyl-4-(trifluoromethyl)-1H-imidazol-2-yl)phenyl)-4,5,6,7-tetrahydro-1H-pyrazolo[4,3-c]pyridine A mixture of 3-(4-isopropylpyrimidin-5-yl)-1-methyl-4,5,6,7-tetrahydro-1H-pyrazolo[4,3-c]pyridine (50 mg, 0.19 mmol), 2-(4-bromophenyl)-1-methyl-4-(trifluoromethyl)-1H-imidazole (89 mg, 0.29 mmol), Pd₂(dba)₃ (36 mg, 0.04 mmol), t-Bu XPhos (17 mg, 0.04 mmol) and Sodium tert-butoxide (56 mg, 0.58 mmol) in dioxane (1.5 mL) was stirred at 100° C. under Ar for 16 h. The mixture was diluted with water (10 mL) and extracted with EtOAc (10 mL×3). The combined organic phases were washed with brine (10 mL), dried over Na₂SO₄, filtered and concentrated under reduced pressure. The residue was purified by prep-TLC (PE/EtOAc=1/1) to give desired product (1.30 mg, 0.0027 mmol, 1.4%).

LCMS: Retention time: 1.455 min, (M+H)$^+$=482.3, method B.

$^1$H NMR (400 MHz, DMSO-d₆) δ=9.14 (s, 1H), 8.64 (s, 1H), 7.83 (s, 1H), 7.52 (d, J=8.8 Hz, 2H), 7.09 (d, J=9.2 Hz,

2H), 4.29 (s, 2H), 3.78-3.73 (m, 8H), 3.50-3.43 (m, 1H), 2.89 (t, J 4.8 Hz, 2H), 1.20-1.18 (m, 6H).

Example B8: Synthesis of Compound 3

Intermediate D

Intermediate C

Ruphos Pd G3, Ruphos, t-BuONa, dioxane, 100° C., 16 h

Compound 3

3-(4-cyclopropyl-6-methoxypyrimidin-5-yl)-1-methyl-5-(4-(1-methyl-4-(trifluoromethyl)-1H-imidazol-2-yl)phenyl)-4,5,6,7-tetrahydro-1H-pyrazolo[4,3-c]pyridine To a solution of 3-(4-cyclopropyl-6-methoxypyrimidin-5-yl)-1-methyl-4,5,6,7-tetrahydro-1H-pyrazolo[4,3-c]pyridine (130 mg, 0.46 mmol) in dioxane (5 mL) were added 2-(4-bromophenyl)-1-methyl-4-(trifluoromethyl)-1H-imidazole (167 mg, 0.55 mmol), RuPhos Pd G3 (4 mg, 0.01 mmol), t-BuONa (61 mg, 0.64 mmol) and RuPhos (64 mg, 0.14 mmol). The mixture was stirred at 100° C. for 16 h. Then the mixture was cooled to rt, diluted with water (15 mL) and extracted with EtOAc (15 mL×3). The combined organic phases were washed with brine (15 mL) and dried over Na$_2$SO$_4$, filtered and concentrated. The residue was purified by prep-TLC (PE/EtOAc=1/3) to afford desired product (30.00 mg, 0.06 mmol, 13%).

LCMS: Retention time: 1.670 min, (M+H)$^+$=510.3, method A.

$^1$H NMR (400 MHz, DMSO-d$_6$) δ=8.62 (s, 1H), 7.83 (d, J=1.2 Hz, 1H), 7.52 (d, J=8.8 Hz, 2H), 7.08 (d, J=9.2 Hz, 2H), 4.14 (s, 2H), 3.91 (s, 3H), 3.80-3.70 (m, 8H), 2.85 (t, J=4.8 Hz, 2H), 2.16-2.12 (m, 1H), 1.04-1.03 (m, 2H), 0.93-0.90 (m, 2H).

Example B9: Synthesis of Compound 4

Intermediate C-1

Cs$_2$CO$_3$
DMF, 60° C., 16 h

Intermediate D-1

CD$_3$I, Cs$_2$CO$_3$
DMF, rt, 16 h

Intermediate A

Pd(dppf)Cl$_2$, Na$_2$CO$_3$
Dioxane, H$_2$O, 100° C., 6 h

TFA
DCM, rt, 2 h

Pd(OAc)$_2$, t-BuONa, X-Phos
Toluene, 100° C., 16 h

-continued

Compound 4

2-(4-bromophenyl)-1-isopropyl-4-(trifluoromethyl)-1H-imidazole

A mixture of 2-(4-bromophenyl)-4-(trifluoromethyl)-1H-imidazole (7.20 g, 24.74 mmol) in DMF (20 mL) was added $Cs_2CO_3$ (20.15 g, 61.84 mmol) and 2-iodopropane (8.41 g, 49.47 mmol). The mixture was stirred at 60° C. for 16 h. Then the mixture was diluted with water (100 mL) and extracted with EtOAc (150 mL×3). The combined organic fractions were washed with brine (100 mL), dried over $Na_2SO_4$, filtered and concentrated under reduced pressure. The residue was purified by column chromatography on silica gel (eluting with PE/EtOAc from 10/1 to 6/1) to give desired product (5.80 g, 17.41 mmol, 70.37%) as a yellow solid.

LCMS: Retention time: 1.600 min, $(M+H)^+=333.0$, method B.

tert-butyl 3-iodo-1-(methyl-d3)-1,4,6,7-tetrahydro-5H-pyrazolo[4,3-c]pyridine-5-carboxylate To a solution of tert-butyl 3-iodo-1,4,6,7-tetrahydro-5H-pyrazolo[4,3-c]pyridine-5-carboxylate (3.10 g, 8.88 mmol) in DMF (35 mL) was added $Cs_2CO_3$ (4.34 g, 13.32 mmol) and $CD_3I$ (1.93 g, 13.32 mmol). The mixture was stirred at rt for 16 h. Then the mixture was diluted with water (100 mL) and extracted with EtOAc (80 mL×3). The combined organic fractions were washed with brine (50 mL), dried over $Na_2SO_4$, filtered and concentrated under reduced pressure. The residue was purified by column chromatography on silica gel (eluting with PE/EA from 100/1 to 5/1) to give desired product (1.80 g, 4.92 mmol, 55.4%) as a white solid.

LCMS: Retention time: 1.740 min, $(M+H)^+=367.1$, method A.

tert-butyl 3-(4-cyclopropyl-6-methoxypyrimidin-5-yl)-1-(methyl-d3)-1,4,6,7-tetrahydro-5H-pyrazolo[4,3-c]pyridine-5-carboxylate To a mixture of tert-butyl 3-iodo-1-(methyl-d3)-1,4,6,7-tetrahydro-5H-pyrazolo[4,3-c]pyridine-5-carboxylate (1.50 g, 4.10 mmol), 4-cyclopropyl-6-methoxy-5-(4,4,5,5-tetramethyl-1,3,2-dioxaborolan-2-yl)pyrimidine (1.24 g, 4.49 mmol) and $Na_2CO_3$ (1.30 g, 12.29 mmol) in dioxane (10 mL) and $H_2O$ (2 mL) was added Pd(dppf)$Cl_2$ (0.30 g, 0.41 mmol) under $N_2$. The mixture was stirred at 100° C. for 6 h and then cooled to room temperature. The mixture was diluted with water (60 mL) and extracted with EtOAc (50 mL×3). The organic layers were collected, washed with brine (60 mL), dried over $Na_2SO_4$, filtered and concentrated under reduced pressure to give the crude product. The residue was purified by column chromatography on silica gel (eluting with PE/EA from 100/1 to 3/1) to give desired product (400 mg, 1.03 mmol, 25.12%) as a colorless oil.

LCMS: Retention time: 1.630 min, $(M+H)^+=389.2$, method A.

3-(4-cyclopropyl-6-methoxypyrimidin-5-yl)-1-(methyl-d3)-4,5,6,7-tetrahydro-1H-pyrazolo[4,3-c]pyridine To a solution of tert-butyl 3-(4-cyclopropyl-6-methoxy-pyrimidin-5-yl)-1-(methyl-d3)-1, 4, 6, 7-tetrahydro-5H-pyrazolo[4, 3-c]pyridine-5-carboxylate (380 mg, 0.98 mmol) in DCM (10 mL) was added TFA (0.73 mL, 9.79 mmol). The mixture was stirred at room temperature for 2 h. $NaHCO_3$ powder was added to adjust pH to 7-8 and filtered. The filtrate was concentrated under reduced pressure and purified by column chromatography on silica gel (eluting with DCM/MeOH from 40/1 to 10/1) to give desired product (190 mg, 0.66 mmol, 67%) as a yellow solid LCMS: Retention time: 0.517 min, $(M+H)^+=289.2$, method A.

3-(4-cyclopropyl-6-methoxypyrimidin-5-yl)-5-(4-(1-isopropyl-4-(trifluoromethyl)-1H-imidazol-2-yl)phenyl)-1-(methyl-d3)-4,5,6,7-tetrahydro-1H-pyrazolo[4,3-c]pyridine To a mixture of 3-(4-cyclopropyl-6-methoxypyrimidin-5-yl)-1-(methyl-d3)-4,5,6,7-tetrahydro-1H-pyrazolo[4,3-c]pyridine (170 mg, 0.59 mmol), 2-(4-bromophenyl)-1-(propan-2-yl)-4-(trifluoromethyl)-1H-imidazole (197 mg, 0.59 mmol), t-BuONa (454 mg, 4.72 mmol) and X-Phos (563 mg, 1.18 mmol) in toluene (5 mL) was added Pd(OAc)$_2$ (13 mg, 0.06 mmol). The mixture was stirred at 100° C. for 16 h. Then the mixture was diluted with water (20 mL) and extracted with EtOAc (20 mL×3). The combined organic fractions were washed with brine (20 mL), dried over $Na_2SO_4$, filtered and concentrated under reduced pressure. The residue was purified by prep-TLC (PE/EA=1/3) to give desired product (117.08 mg, 0.22 mmol, 97.76% purity, 37.29%).

LCMS: Retention time: 1.800 min, $(M+H)^+=541.3$, method A.

1HNMR (400 MHz, DMSO-$d_6$) δ=8.62 (s, 1H), 8.07 (s, 1H), 7.36 (d, J 9.2 Hz, 2H), 7.09 (d, J=9.2 Hz, 2H), 4.48-4.44 (m, 1H), 4.14 (s, 2H), 3.91 (s, 3H), 3.77 (t, J=5.6 Hz, 2H), 2.85 (t, J=5.6 Hz, 2H), 2.16-2.14 (m, 1H), 1.39 (d, J=6.8 Hz, 6H), 1.05-1.02 (m, 2H), 0.94-0.89 (m, 2H).

Example B10: Synthesis of Compound 5

-continued

Intermediate D
$\xrightarrow{\text{Cs}_2\text{CO}_3, \text{DMSO}}$
$140° \text{C., 2 h, MW}$ Compound 5

2-bromo-5-(4-(trifluoromethyl)-1H-imidazol-2-yl) pyridine

A mixture of 3, 3-dibromo-1, 1, 1-trifluoropropan-2-one (7.258 g, 26.88 mmol) and NaOAc (4.41 g, 53.76 mmol) in H₂O (50 mL) was stirred at 100° C. for 1 h and then cooled to room temperature. Then the mixture of 6-bromonicotin-aldehyde (5.00 g, 26.88 mmol) and NH₄OH (13.80 mL, 107.52 mmol) in MeOH (50 mL) was added to the above mixture. The resulting mixture was stirred at room tempera-ture for 16 h. The mixture was concentrated, diluted with water (100 mL), and extracted with ethyl acetate (100 mL×3). The combined organic layers were washed with brine (200 mL), dried over Na₂SO₄, filtered and concen-trated under vacuum. The residue was purified by flash chromatography on silica gel eluted with PE/EA=10/1 to afford desired product (5.30 g, 18.16 mmol, 67.6%) as a white solid.

LCMS: Retention time: 1.647 min, (M+H)⁺=291.9, method A.

2-bromo-5-(1-methyl-4-(trifluoromethyl)-1H-imida-zol-2-yl)pyridine

To a solution of 2-bromo-5-(4-(trifluoromethyl)-1H-imi-dazol-2-yl)pyridine (5.50 g, 18.83 mmol) in DMF (55 mL) was added NaH (0.90 g, 22.60 mmol, 60% dispersion in mineral oil) at 0° C. under Ar. After stirred for 30 minutes, CH₃I (1.172 mL, 18.83 mmol) was added. The mixture was stirred at rt for 16 h. Then the reaction mixture was quenched with water (30 mL) at 0° C. and extracted with ethyl acetate (100 mL×3). The combined organic layers were washed with brine (200 mL), dried over Na₂SO₄, filtered and concentrated under vacuum to give the crude product. The crude product was purified by flash chromatography on silica gel eluted with PE/EA=5/1 to afford the desired product (2.35 g, 7.66 mmol, 40.7%) as a white solid.

LCMS: Retention time: 1.667 min, (M+H)⁺=306.0, method A.

3-(4-cyclopropyl-6-methoxypyrimidin-5-yl)-1-methyl-5-(5-(1-methyl-4-(trifluoromethyl)-1H-imi-dazol-2-yl)pyridin-2-yl)-4,5,6,7-tetrahydro-1H-pyra-zolo[4,3-c]pyridine To a solution of 3-(4-cyclopropyl-6-methoxypyrimidin-5-yl)-1-methyl-4,5,6,7-tetrahydro-1H-pyrazolo[4,3-c]pyri-dine (70 mg, 0.25 mmol) and 2-bromo-5-(1-methyl-4-(trif-luoromethyl)-1H-imidazol-2-yl)pyridine (83 mg, 0.27 mmol) in dry DMSO (2 mL) was added Cs₂CO₃ (160 mg, 0.49 mmol). The mixture was degassed with N₂ for three times and stirred at 140° C. for 2 hours under microwave conditions. Then the reaction mixture was cooled to rt and water (10 mL) was added. The resulting mixture was extracted with ethyl acetate (10 mL×3). The combined organic layer was washed with brine (20 mL), dried over Na₂SO₄, filtered and concentrated to give the crude product. The crude product was purified by prep-TLC (PE/EA=1/1) to afford the desired product (20.00 mg, 0.039 mmol, 15.6%).

LCMS: Retention time: 1.727 min, (M+H)⁺=511.2, method A.

¹H NMR (400 MHz, DMSO-d₆) δ=8.62 (s, 1H), 8.41 (d, J=2.0 Hz, 1H), 7.87 (d, J=1.2 Hz, 1H), 7.84 (dd, J=8.8, 2.4 Hz, 1H), 7.03 (d, J=9.2 Hz, 1H), 4.46 (s, 2H), 4.03 (t, J=6.0 Hz, 2H), 3.91 (s, 3H), 3.75 (s, 3H), 3.74 (s, 3H), 2.86 (t, J=6.0 Hz, 2H), 2.18-2.15 (m, 1H), 1.05-1.02 (m, 2H), 0.95-0.91 (m, 2H).

Example B11: Synthesis of Compound 6

1. NaOAc, H₂O, 100° C., 1 h
2. MeOH, NH₄OH, rt, 16 h $\xrightarrow{\text{CH}_3\text{I, NaH, DMF}}$
$0° \text{C. to rt, 16 h}$ Intermediate D
$\xrightarrow{\text{Pd(OAc)}_2, \text{X-Phos, t-BuONa}}$
$\text{toluene, } 100° \text{C., 16 h}$ -continued Compound 6

5-bromo-2-(4-(trifluoromethyl)-1H-imidazol-2-yl)
pyridine

A mixture of 3,3-dibromo-1,1,1-trifluoropropan-2-one (9.07 g, 33.60 mmol) and NaOAc (5.51 g, 67.20 mmol) in H$_2$O (50 mL) was stirred at 100° C. for 1 h and then cooled to rt. A mixture of 5-bromopyridine-2-carbaldehyde (5.00 g, 26.88 mmol) and NH$_4$OH (17.26 mL, 134.40 mmol) in MeOH (50 mL) was added and the resulting mixture was stirred at rt for 16 h. Then the mixture was concentrated under reduced pressure to remove methanol and extracted with ethyl acetate (50 mL) for three times. The combined organic fractions were washed with brine (80 mL), dried over Na$_2$SO$_4$, filtered and concentrated under reduced pressure. The residue was purified by column chromatography on silica gel (eluting with PE/EA from 10/1 to 3/1) to give desired product (5.73 g, 19.62 mmol, 73.00%) as a yellow solid.

LCMS: Retention time: 1.737 min, (M+H)$^+$=291.9, method A.

5-bromo-2-(1-methyl-4-(trifluoromethyl)-1H-imida-
zol-2-yl)pyridine

To a solution of 5-bromo-2-(4-(trifluoromethyl)-1H-imidazol-2-yl)pyridine (6.00 g, 20.54 mmol) in DMF (70 mL) was added NaH (1.64 g, 41.08 mmol, 60% in mineral oil) at 0° C. under Ar. After stirring for 30 minutes, to the mixture was added iodomethane (1.53 mL, 24.65 mmol). The resulting mixture was stirred at room temperature for 16 h. The mixture was diluted with water (100 mL) and extracted with ethyl acetate (70 mL) for three times. The combined organic fractions were washed with brine (90 mL), dried over Na$_2$SO$_4$, filtered and concentrated under reduced pressure. The residue was purified by column chromatography on silica gel (eluting with PE/EA from 100/1 to 3/1) to give desired product (5.00 g, 16.33 mmol, 79.5%) as a yellow solid.

LCMS: Retention time: 1.877 min, (M+H)$^+$=306.0, method A.

3-(4-cyclopropyl-6-methoxypyrimidin-5-yl)-1-
methyl-5-(6-(1-methyl-4-(trifluoromethyl)-1H-imi-
dazol-2-yl)pyridin-3-yl)-4,5,6,7-tetrahydro-1H-pyra-
zolo[4,3-c]pyridine To a solution of 3-(4-cyclopropyl-6-methoxypyrimidin-5-yl)-1-methyl-4,5,6,7-tetrahydro-1H-pyrazolo[4,3-c]pyridine (150 mg, 0.53 mmol), 5-bromo-2-(1-methyl-4-(trifluoromethyl)-1H-imidazol-2-yl)pyridine (226 mg, 0.74 mmol), X-Phos (501 mg, 1.05 mmol) and t-BuONa (101 mg, 1.05 mmol) in toluene (5 mL) was added Pd(OAc)$_2$ (12 mg, 0.05 mmol). The mixture was degassed with N$_2$ for three times and stirred at 100° C. for 16 h. The reaction mixture was cooled to room temperature and concentrated under reduced pressure. Then the residue was diluted with water (10 mL) and extracted with ethyl acetate (15 mL×3). The combined organic layers were washed with brine (20 mL), dried over Na$_2$SO$_4$, filtered and concentrated under reduced pressure to give the crude product. The crude product was purified by prep-TLC (PE/EA=1/1) to give desired product (130 mg, 0.24 mmol, 96.30% purity, 45%).

LCMS: Retention time: 1.567 min, (M+H)$^+$=511.2, method A.

$^1$H NMR (400 MHz, DMSO-d$_6$) δ=8.62 (s, 1H), 8.41 (s, 1H), 7.87-7.85 (m, 2H), 7.51 (dd, J=2.8 Hz, 8.8 Hz, 1H), 4.21 (s, 2H), 4.02 (s, 3H), 3.92 (s, 3H), 3.83 (t, J=5.6 Hz, 2H), 3.75 (s, 3H), 2.87 (t, J=5.6 Hz, 2H), 2.16-2.13 (m, 1H), 1.05-1.03 (m, 2H), 0.93-0.90 (m, 2H).

Example B12: Synthesis of Compound 7

Compound 7

2-(4-bromo-3-fluorophenyl)-4-(trifluoromethyl)-1H-
imidazole

A mixture of 3,3-dibromo-1,1,1-trifluoropropan-2-one (8.313 g, 30.79 mmol) and NaOAc (5.05 g, 61.57 mmol) in H$_2$O (50 mL) was stirred at 100° C. for 1 h and then cooled to rt. A mixture of 4-bromo-3-fluorobenzaldehyde (5.00 g, 24.63 mmol), MeOH (50 mL), and NH$_4$OH (15.81 mL, 123.15 mmol) was added, and the resulting mixture was stirred at rt for 16 h. The mixture was diluted with water (100 mL) and extracted with EtOAc (80 mL×5). The combined organic fractions were washed with brine (100 mL), dried over Na$_2$SO$_4$, filtered and concentrated. The residue was purified by column chromatography on silica gel (eluting with PE/EA from 100/1 to 15/1) to give desired product (3.60 g, 11.65 mmol, 47%) as a yellow solid.

LCMS: Retention time: 1.827 min, (M+H)$^+$=308.9, method A.

2-(4-bromo-3-fluorophenyl)-1-methyl-4-(trifluoromethyl)-1H-imidazole

To a solution of 2-(4-bromo-3-fluorophenyl)-4-(trifluoromethyl)-1H-imidazole (3.60 g, 11.65 mmol) in DMF (40 mL) was added NaH (0.93 g, 23.30 mmol, 60% dispersion in mineral oil) at 0° C. After stirred for 30 minutes, CH$_3$I (0.87 mL, 13.98 mmol) was added to the mixture. The mixture was stirred at rt for 16 h. The mixture was diluted with water (100 mL) and extracted with EtOAc (60 mL×5). The combined organic fractions were washed with brine (80 mL×3), dried over Na$_2$SO$_4$, filtered and concentrated. The residue was purified by column chromatography on silica gel (eluting with PE/EA from 100/1 to 20/1) to give desired product (2.19 g, 6.78 mmol, 58.2%) as a yellow solid.

LCMS: Retention time: 1.117 min, (M+H)$^+$=323.1, method A.

3-(4-cyclopropyl-6-methoxypyrimidin-5-yl)-5-(2-fluoro-4-(1-methyl-4-(trifluoromethyl)-1H-imidazol-2-yl)phenyl)-1-methyl-4,5,6,7-tetrahydro-1H-pyrazolo[4,3-c]pyridine A mixture of 2-(4-bromo-3-fluorophenyl)-1-methyl-4-(trifluoromethyl)-1H-imidazole (181 mg, 0.56 mmol), 3-(4-cyclopropyl-6-methoxypyrimidin-5-yl)-1-methyl-4,5,6,7-tetrahydro-1H-pyrazolo[4,3-c]pyridine (80 mg, 0.28 mmol), t-BuONa (216 mg, 2.24 mmol), X-Phos (1069 mg, 2.24 mmol) and Pd(OAc)$_2$ (6 mg, 0.03 mmol) in toluene (5 mL) was stirred at 100° C. for 16 h. Then the mixture was cooled to rt, concentrated and water (10 mL) was added. The mixture was extracted with EtOAc (10 mL×3). The combined organic fractions were washed with brine (20 mL), dried over Na$_2$SO$_4$, filtered and concentrated. The residue was purified by prep-TLC (PE/EA=1/3) to give desired product (17.60 mg, 0.033 mmol, 11.8%).

LCMS: Retention time: 1.780 min, (M+H)$^+$=528.2, method A.

1HNMR (400 MHz, DMSO-d$_6$) δ=8.61 (s, 1H), 7.90 (s, 1H), 7.50 (dd, J=14, 2.0 Hz, 1H), 7.42 (dd, J=8.4, 2.0 Hz, 1H), 7.17 (t, J=8.8 Hz, 1H), 4.00 (s, 2H), 3.90 (s, 3H), 3.77 (s, 6H), 3.56 (t, J=5.6 Hz, 2H), 2.86 (t, J=5.2 Hz, 2H), 2.19-2.15 (m, 1H), 1.05-1.01 (m, 2H), 0.95-0.90 (m, 2H).

Example B13: Synthesis of Compound 8

1. NaOAc, H$_2$O, 100° C., 1 h
2. MeOH, NH$_4$OH, rt, 16 h

-continued

1. NaH, DMF, 0° C., 0.5 h
2. CH$_3$I, rt, 16 h

Intermediate D

Pd(OAc)$_2$, X-Phos, t-BuONa
toluene, 100° C., 16 h

Compound 8

2-(4-bromo-2-fluorophenyl)-4-(trifluoromethyl)-1H-imidazole

To a solution of 3, 3-dibromo-1, 1, 1-trifluoropropan-2-one (6.65 g, 24.63 mmol) in H$_2$O (60 mL) was added NaOAc (4.04 g, 49.26 mmol). The mixture was stirred at 100° C. for 1 h and then cooled to rt. A mixture of 4-bromo-2-fluorobenzaldehyde (5 g, 24.63 mmol) and NH$_4$OH (12.65 mL, 98.52 mmol) in MeOH (100 mL) was added and the resulting mixture was stirred at rt for 16 h. Then the mixture was concentrated to remove methanol and extracted with ethyl acetate (30 mL) for three times. The combined organic layer was washed with brine (80 mL), dried over Na$_2$SO$_4$, filtered and concentrated under vacuum. The residue was recrystallized from (PE/EA=20/1, 100 mL) to give desired product (4.05 g, 13.10 mmol, 53% yield) as a yellow solid.

LCMS: Retention time: 1.611 min, (M+H)$^+$=309.0, method A.

2-(4-bromo-2-fluorophenyl)-1-methyl-4-(trifluoromethyl)-1H-imidazole

To a solution of 2-(4-bromo-2-fluorophenyl)-4-(trifluoromethyl)-1H-imidazole (2.00 g, 6.47 mmol) in DMF (30 mL) was added NaH (0.52 g, 12.94 mmol, 60% dispersion in mineral oil) at 0° C. After stirring for 0.5 h, MeI (0.60 mL, 9.71 mmol) was added. The resulting mixture was stirred at rt for 16 h. Then the mixture was quenched with saturated ammonium chloride solution (100 mL) and water (50 mL) at 0° C. The mixture was extracted with ethyl acetate (100 mL) for three times. The combined organic fractions were washed with brine (250 mL), dried over Na$_2$SO$_4$, filtered and concentrated. The residue was purified by column chromatography on silica gel (eluting with PE/EtOAc from

|

100/0 to 12/1) to give desired product (1.75 g, 5.42 mmol, 84% yield) as a light-yellow solid.

LCMS: Retention time: 1.677 min, $(M+H)^+=323.0$, method A.

3-(4-cyclopropyl-6-methoxypyrimidin-5-yl)-5-(3-fluoro-4-(1-methyl-4-(trifluoromethyl)-1H-imidazol-2-yl)phenyl)-1-methyl-4,5,6,7-tetrahydro-1H-pyrazolo[4,3-c]pyridine To a solution of 3-(4-cyclopropyl-6-methoxypyrimidin-5-yl)-1-methyl-4,5,6,7-tetrahydro-1H-pyrazolo[4,3-c]pyridine (100 mg, 0.35 mmol), 2-(4-bromo-2-fluorophenyl)-1-methyl-4-(trifluoromethyl)-1H-imidazole (226 mg, 0.70 mmol), X-Phos (334 mg, 0.70 mmol) and t-BuONa (334 mg, 0.70 mmol) in toluene (5 mL) was added Pd(OAc)$_2$ (8 mg, 0.04 mmol). The mixture was degassed with N$_2$ for three times and stirred at 100° C. for 16 h. The reaction mixture was cooled to rt and concentrated. Then the residue was diluted with water (10 mL) and extracted with ethyl acetate (15 mL×3). The combined organic layer was washed with brine (20 mL), filtered and concentrated to give the crude product. The crude product was purified by prep-TLC (PE/EA=1/1) to give desired product (47.00 mg, 0.089 mmol, 25%).

LCMS: Retention time: 1.577 min, $(M+H)^+=528.2$, method A.

$^1$H NMR (400 MHz, DMSO-d$_6$) δ=8.62 (s, 1H), 7.91 (s, 1H), 7.35-7.31 (m, 1H), 6.98-6.91 (m, 2H), 4.18 (s, 2H), 3.91 (s, 3H), 3.81 (t, J=5.4 Hz, 2H), 3.75 (s, 3H), 3.56 (s, 3H), 2.85 (t, J=5.2 Hz, 2H), 2.16-2.14 (m, 1H), 1.04-1.02 (m, 2H), 0.93-0.90 (m, 2H)

Example B14: Synthesis of Compound 9

-continued

Compound 9 tert-butyl 1-(difluoromethyl)-3-iodo-1,4,6,7-tetra-hydro-5H-pyrazolo[4,3-c]pyridine-5-carboxylate To a mixture of tert-butyl 3-iodo-1,4,6,7-tetrahydro-5H-pyrazolo[4,3-c]pyridine-5-carboxylate (2800 mg, 8.02 mmol) and Potassium fluoride (932 mg, 16.04 mmol) in Acetonitrile (50 mL) was added diethyl (bromodifluoromethyl)phosphonate (2141 mg, 8.02 mmol) at rt. The mixture was stirred at rt for 16 h. Then the mixture was concentrated under reduced pressure. The residue was purified by column chromatography on silica gel (eluting with PE/EtOAc=10/1) to give desired product (1.565 g, 3.92 mmol, 48.9%) as a white solid.

LCMS: Retention time: 1.526 min, $(M+H)^+=400.2$, method B.

tert-butyl 3-(4-cyclopropyl-6-methoxypyrimidin-5-yl)-1-(difluoromethyl)-1,4,6,7-tetrahydro-5H-pyra-zolo[4,3-c]pyridine-5-carboxylate A mixture of tert-butyl 1-(difluoromethyl)-3-iodo-1,4,6,7-tetrahydro-5H-pyrazolo[4,3-c]pyridine-5-carboxylate (1100 mg, 2.76 mmol), 4-cyclopropyl-6-methoxy-5-(4,4,5,5-tetramethyl-1,3,2-dioxaborolan-2-yl)pyrimidine (1141 mg, 4.13 mmol), Pd(dppf)Cl$_2$ (202 mg, 0.28 mmol) and K$_2$CO$_3$ (762 mg, 5.51 mmol) in dioxane (10 mL) and water (2 mL) was stirred at 100° C. under Ar for 16 h. Then the mixture was cooled to rt, diluted with water (15 mL) and extracted with EtOAc (15 mL×3). The combined organic fractions were washed with brine (15 mL), dried over Na$_2$SO$_4$, filtered and concentrated under reduced pressure. The residue was purified by column chromatography on silica gel (eluting with PE/EtOAc=5/1) to give desired product (700 mg, 1.66 mmol, 60.1%) as a white solid.

LCMS: Retention time: 1.595 min, (M+H)$^+$=422.2, method B.

3-(4-cyclopropyl-6-methoxypyrimidin-5-yl)-1-(difluoromethyl)-4,5,6,7-tetrahydro-1H-pyrazolo[4,3-c]pyridine A solution of tert-butyl 3-(4-cyclopropyl-6-methoxypyrimidin-5-yl)-1-(difluoromethyl)-1,4,6,7-tetrahydro-5H-pyrazolo[4,3-c]pyridine-5-carboxylate (700 mg, 1.66 mmol) in DCM (6 mL) was added TFA (3 mL) at rt. The mixture was stirred at rt for 3 h. Then the mixture was concentrated and redissolved in DCM (15 mL). The pH of the solution was adjusted to 8.0 with 8 N NH$_3$/MeOH and concentrated under reduced pressure. The residue was purified by prep-TLC (DCM/MeOH=20/1) to give desired product (500 mg, 1.56 mmol, 94%) as a white solid.

LCMS: Retention time: 0.678 min, (M+H)$^+$=322.1, method B.

3-(4-cyclopropyl-6-methoxypyrimidin-5-yl)-1-(difluoromethyl)-5-(4-(1-methyl-4-(trifluoromethyl)-1H-imidazol-2-yl)phenyl)-4,5,6,7-tetrahydro-1H-pyrazolo[4,3-c]pyridine A mixture of 3-(4-cyclopropyl-6-methoxypyrimidin-5-yl)-1-(difluoromethyl)-4,5,6,7-tetrahydro-1H-pyrazolo[4,3-c]pyridine (200 mg, 0.62 mmol), 2-(4-bromophenyl)-1-methyl-4-(trifluoromethyl)-1H-imidazole (190 mg, 0.62 mmol), Pd(OAc)$_2$ (14 mg, 0.06 mmol), X-Phos (593 mg, 1.25 mmol) and sodium tert-butoxide (120 mg, 1.25 mmol) in toluene (5 mL) was stirred at 100° C. under Ar for 16 h. Then the mixture was cooled to rt, diluted with water (10 mL) and extracted with EtOAc (10 mL×3). The combined organic phases were washed with brine (10 mL), dried over Na$_2$SO$_4$, filtered and concentrated under reduced pressure. The residue was purified by prep-TLC (PE/EtOAc=1/1) to give desired product (80 mg, 0.147 mmol, 23.7%).

LCMS: Retention time: 1.531 min, (M+H)$^+$=546.2, method B.

$^1$H NMR (400 MHz, DMSO-d$_6$) δ=8.69 (s, 1H), 8.00-7.70 (m, 2H), 7.54 (d, J 8.8 Hz, 2H), 7.11 (d, J=8.8 Hz, 2H), 4.17 (s, 2H), 3.94 (s, 3H), 3.82-3.79 (m, 2H), 3.74 (s, 3H), 3.05-3.02 (m, 2H), 2.03-1.99 (m, 1H), 1.10-1.06 (m, 2H), 0.98-0.94 (m, 2H).

Example B15: Synthesis of Compound 10

10.1

-continued

Compound 10

2-fluoro-5-(4-(trifluoromethyl)-1H-imidazol-2-yl)pyridine

To a solution of 3, 3-dibromo-1, 1, 1-trifluoropropan-2-one (69.29 g, 256.78 mmol) in H$_2$O (150 mL) was added NaOAc (32.79 g, 399.73 mmol) at 0° C. The mixture was stirred at 0° C. for 10 minutes and then heated at 100° C. for another 1 hour under Ar. After cooling to rt, 6-fluoronicotinaldehyde (25.00 g, 199.84 mmol), NH$_4$OH (93.39 g, 799.36 mmol, 30%) and MeOH (200 mL) were added. The mixture was stirred at rt for 16 hr under Ar. Then the mixture was concentrated to remove MeOH. The resulting suspension was filtered. The solid was washed with water (100 mL) and Et$_2$O (100 mL), and dried to give the title compound (46.05 g, 199.22 mmol, 100% yield) as a yellow solid LC-MS (ESI+): m/z 232.1 (M+H)$^+$.

2-fluoro-5-(1-isopropyl-4-(trifluoromethyl)-1H-imidazol-2-yl)pyridine

To a mixture of 2-fluoro-5-(4-(trifluoromethyl)-1H-imidazol-2-yl)pyridine (10.00 g, 43.26 mmol) in DMF (200 mL) were added Cs$_2$CO$_3$ (35.24 g, 108.16 mmol) and 2-iodopropane (36.77 g, 216.31 mmol). The reaction mixture was stirred at 60° C. for 16 hr under Ar. After cooling to rt, to the mixture was added water (300 mL). After extraction with EtOAc (300 mL×2), the combined organic layers were washed with brine (300 mL), dried over Na$_2$SO$_4$, filtered and concentrated under reduced pressure to give a residue, which was purified by column chromatography on silica gel eluting with ethyl acetate (from 0% to 8.5%) in petroleum ether to give the title compound (4.24 g, 15.52 mmol, 36% yield) as a yellow solid.

LC-MS (ESI+): m/z 274.1 (M+H)$^+$.

3-(4-cyclopropyl-6-methoxypyrimidin-5-yl)-5-(5-(1-isopropyl-4-(trifluoromethyl)-1H-imidazol-2-yl)pyridin-2-yl)-1-methyl-4,5,6,7-tetrahydro-1H-pyrazolo[4,3-c]pyridine To a solution of 3-(4-cyclopropyl-6-methoxypyrimidin-5-yl)-1-methyl-4,5,6,7-tetrahydro-1H-pyrazolo[4,3-c]pyridine (100 mg, 0.35 mmol) in dry DMF (3 mL) were added 2-fluoro-5-(1-isopropyl-4-(trifluoromethyl)-1H-imidazol-2-yl)pyridine (143 mg, 0.52 mmol) and $Et_3N$ (106 mg, 1.05 mmol) at rt. The reaction mixture was stirred at 100° C. for 16 hr. After cooling to rt, to the mixture was added water (30 mL). After extraction with EtOAc (20 mL×2), the combined organic fractions were washed with brine (20 mL), dried over $Na_2SO_4$, filtered and concentrated under reduced pressure to give a residue, which was purified by prep-TLC (PE/EtOAc=1/3) to give the title compound (10.52 mg, 0.02 mmol, 6% yield).

LC-MS (ESI+): m/z 539.3 (M+H)$^+$.

$^1$HNMR (400 MHz, DMSO-d$_6$) δ=8.62 (s, 1H), 8.25 (s, 1H), 8.12 (s, 1H), 7.74-7.64 (m, 1H), 7.04 (d, J=8.8 Hz, 1H), 4.46 (s, 2H), 4.45-4.36 (m, 1H), 4.08-4.00 (m, 2H), 3.91 (s, 3H), 3.76 (s, 3H), 2.90-2.82 (m, 2H), 2.22-2.13 (m, 1H), 1.39 (d, J=6.4 Hz, 6H), 1.10-1.01 (m, 2H), 0.97-0.90 (m, 2H).

Example B16: Synthesis of Compound 11

Compound 11

3-(4-cyclopropyl-6-methoxypyrimidin-5-yl)-5-(5-(1-isopropyl-4-(trifluoromethyl)-1H-imidazol-2-yl)pyridin-2-yl)-1-(methyl-d3)-4,5,6,7-tetrahydro-1H-pyrazolo[4,3-c]pyridine To a solution of 3-(4-cyclopropyl-6-methoxypyrimidin-5-yl)-1-(methyl-d3)-4,5,6,7-tetrahydro-1H-pyrazolo[4,3-c]pyridine (400 mg, 1.39 mmol) (see Example B9 for its synthesis) in DMF (10 mL) were added TEA (0.193 mL, 1.39 mmol) and 2-fluoro-5-(1-isopropyl-4-(trifluoromethyl)-1H-imidazol-2-yl)pyridine (568 mg, 2.08 mmol). The reaction mixture was stirred at 100° C. for 16 hr. After cooling to rt, to the mixture was added water (15 mL). After extraction with EtOAc (15 mL×3), the combined organic phases were washed with brine (15 mL), dried over $Na_2SO_4$, filtered and concentrated. The residue was purified with prep-TLC (DCM/MeOH=20/1) to give the title compound (46.95 mg, 0.087 mmol, 6% yield).

LC-MS (ESI+): m/z 542.3 (M+H)$^+$.

$^1$H NMR (400 MHz, DMSO-d$_6$) δ=8.62 (s, 1H), 8.25 (d, J=2.4 Hz, 1H), 8.12 (s, 1H), 7.70 (dd, J=9.2, 2.8 Hz, 1H), 7.03 (d, J=9.2 Hz, 1H), 4.50-4.36 (m, 3H), 4.03 (t, J=4.8 Hz, 2H), 3.91 (s, 3H), 2.86 (t, J=5.6 Hz, 2H), 2.23-2.14 (m, 1H), 1.39 (d, J=6.8 Hz, 6H), 1.09-1.00 (m, 2H), 0.97-0.88 (m, 2H).

Example B17: Synthesis of Compound 13

3-(4-cyclopropyl-6-methylpyrimidin-5-yl)-1-methyl-5-(5-(1-methyl-4-(trifluoromethyl)-1H-imidazol-2-yl)pyridin-2-yl)-4,5,6,7-tetrahydro-1H-pyrazolo[4,3-c]pyridine Compound 13

In a similar fashion according to the procedure for Compound 5, Compound 13 was synthesized by replacing 4-chloro-6-methoxypyrimidine with 4-chloro-6-methylpyrimidine. The crude product was purified by prep-TLC (DCM/EtOAc=2/1) to afford the title compound (3.54 mg, 1% yield).

LC-MS (ESI+): m/z 495.3 (M+H)$^+$.

$^1$H NMR (400 MHz, MeOD-d$_4$) δ=8.83 (s, 1H), 8.39 (d, J=2.0 Hz, 1H), 7.84-7.81 (m, 1H), 7.67 (d, J=1.2 Hz, 1H), 7.02 (d, J=9.2 Hz, 1H), 4.65-4.41 (m, 2H), 4.22-4.04 (m, 2H), 3.87 (s, 3H), 3.78 (s, 3H), 2.97 (t, J=5.6 Hz, 2H), 2.36 (s, 3H), 1.94-1.88 (m, 1H), 1.28-1.16 (m, 2H), 1.13-0.95 (m, 2H).

Example B18: Synthesis of Compound 15

15.1

-continued

Intermediate D
TEA, DMF
100° C., 16 h 15.2

Compound 15

2-fluoro-5-hydrazineylpyridine

A suspension of 6-fluoropyridin-3-amine (5.00 g, 44.60 mmol) in water (50 mL) and conc. HCl (30 mL) was cooled to –20° C. Then a solution of sodium nitrite (3.08 g, 44.64 mmol) in water (20 mL) was added dropwise. The resulting mixture was stirred at –20° C. for 45 minutes. Subsequently, a solution of SnCl$_2$ (8.46 g, 44.62 mmol) in conc. HCl (25 mL) was added. The mixture was stirred at 0° C. for another 1 hr. The pH of the mixture was adjusted to 10 with 1N NaOH aqueous solution. After extraction with ethyl acetate (80 mL×3), the combined organic layers were washed with brine (80 mL), dried over Na$_2$SO$_4$, filtered and concentrated to give the title compound (7 g, crude), which was used directly in next step.

LC-MS (ESI+): m/z 128.2 (M+H)$^+$.

2-fluoro-5-(5-methyl-3-(trifluoromethyl)-1H-pyrazol-1-yl)pyridine

To a solution of 2-fluoro-5-hydrazineylpyridine (7.00 g, 11.01 mmol, 20% purity) in HFIP (50 mL) were added TEA (2.30 mL, 16.62 mmol) and 1,1,1-trifluoropentane-2,4-dione (0.85 g, 5.52 mmol) slowly at 0° C. The reaction mixture was stirred at 0° C. for 2 hr. Then the mixture was concentrated and diluted with water (15 mL). After extraction with ethyl acetate (15 mL×3), the combined organic layers were washed with brine (20 mL), dried over Na$_2$SO$_4$, filtered and concentrated under reduced pressure. The residue was purified by column chromatography on silica gel eluted with 10% ethyl acetate in petroleum ether to give the title compound (700 mg, 2.86 mmol, 52% yield) as a yellow solid.

LC-MS (ESI+): m/z 246.1 (M+H)$^+$.

3-(4-cyclopropyl-6-methoxypyrimidin-5-yl)-1-methyl-5-(5-(5-methyl-3-(trifluoromethyl)-1H-pyrazol-1-yl)pyridin-2-yl)-4,5,6,7-tetrahydro-1H-pyrazolo[4,3-c]pyridine To a solution of 2-fluoro-5-(5-methyl-3-(trifluoromethyl)-1H-pyrazol-1-yl)pyridine (120 mg, 0.49 mmol) and 3-(4- cyclopropyl-6-methoxypyrimidin-5-yl)-1-methyl-4,5,6,7-tetrahydro-1H-pyrazolo[4,3-c]pyridine (70 mg, 0.245 mmol) in DMF (5 mL) was added TEA (0.10 mL, 0.72 mmol). The reaction mixture was stirred at 100° C. for 16 hr. After cooling to rt, to the mixture was added water (20 mL). After extraction with EtOAc (20 mL×3), the combined organic layers were washed with brine (20 mL), dried over Na$_2$SO$_4$, filtered and concentrated under reduced pressure to give a residue, which was purified by pre-TLC (PE/EA=2/1) to afford the title product (18.65 mg, 15% yield).

LC-MS (ESI+): m/z 511.2 (M+H)$^+$.

$^1$H NMR (400 MHz, DMSO-d$_6$) δ=8.62 (s, 1H), 8.25 (d, J=2.8 Hz, 1H), 7.71 (dd, J=2.4 Hz, J=8.8 Hz, 1H), 7.06 (d, J=8.8 Hz, 1H), 6.72 (s, 1H), 4.46 (s, 2H), 4.03 (t, J=6.0 Hz, 2H), 3.90 (s, 3H), 3.76 (s, 3H), 2.87 (t, J=5.2 Hz, 2H), 2.27 (s, 3H), 2.23-2.12 (m, 1H), 1.07-1.00 (m, 2H), 0.98-0.89 (m, 2H).

Example B19: Synthesis of Compound 16

3-(4-cyclopropyl-6-methoxypyrimidin-5-yl)-1-ethyl-5-(5-(1-methyl-4-(trifluoromethyl)-1H-imidazol-2-yl)pyridin-2-yl)-4,5,6,7-tetrahydro-1H-pyrazolo[4,3-c]pyridine Compound 16

In a similar fashion according to the procedure for Compound 5, Compound 16 was synthesized by replacing iodomethane with iodoethane. The crude product was purified by prep-TLC (PE/EA=1/3) to give the title compound (83.21 mg, 0.16 mmol, 32% yield).

LC-MS (ESI+): m/z 525.2 (M+H)$^+$.

$^1$HNMR (400 MHz, DMSO-d) δ=8.62 (s, 1H), 8.41 (d, J=2.4 Hz, 1H), 7.87 (s, 1H), 7.84 (dd, J=2.0 Hz, 8.8 Hz, 1H), 7.02 (d, J=9.2 Hz, 1H), 4.46 (s, 2H), 4.14-4.00 (m, 4H), 3.92 (s, 3H), 3.74 (s, 3H), 2.88 (t, J=5.2 Hz, 2H), 2.26-2.16 (m, 1H), 1.34 (t, J=7.2 Hz, 3H), 1.08-1.00 (m, 2H), 0.97-0.87 (m, 2H).

Example B20: Synthesis of Compound 17

Intermediate C
Pd(OAc)$_2$, t-BuONa, X-Phos
Toluene, 100° C., 16 h

-continued

Compound 17

3-(4-cyclopropyl-6-methoxypyrimidin-5-yl)-1-(methyl-d3)-5-(4-(1-methyl-4-(trifluoromethyl)-1H-imidazol-2-yl)phenyl)-4,5,6,7-tetrahydro-1H-pyrazolo[4,3-c]pyridine To a mixture of 2-(4-bromophenyl)-1-methyl-4-(trifluoromethyl)-1H-imidazole (254 mg, 0.83 mmol), 3-(4-cyclopropyl-6-methoxypyrimidin-5-yl)-1-(methyl-d3)-4,5,6,7-tetrahydro-1H-pyrazolo[4,3-c]pyridine (200 mg, 0.69 mmol) (see Example B9 for synthesis), t-BuONa (533 mg, 5.55 mmol) and X-Phos (661.6 mg, 1.39 mmol) in toluene (5 mL) was added Pd(OAc)$_2$ (15.58 mg, 0.07 mmol). The reaction mixture was stirred at 100° C. for 16 hr. After cooling to rt, to the mixture was added water (30 mL). After extraction with EtOAc (30 mL×2), the combined organic layers were washed with brine (10 mL), dried over Na$_2$SO$_4$, filtered and concentrated under reduced pressure to give a residue, which was purified by prep-TLC (PE/EtOAc=1/3) to give the title compound (117.08 mg, 0.23 mmol, 33% yield).

LC-MS (ESI+): m/z 513.2 (M+H)$^+$.

$^1$HNMR (400 MHz, DMSO-d$_6$) δ=8.62 (s, 1H), 7.83 (s, 1H), 7.52 (d, J=8.8 Hz, 2H), 7.08 (d, J=8.8 Hz, 2H), 4.14 (s, 2H), 3.91 (s, 3H), 3.77 (t, J=5.6 Hz, 2H), 3.73 (s, 3H), 2.85 (t, J 5.2 Hz, 2H), 2.19-2.09 (m, 1H), 1.09-1.00 (m, 2H), 0.97-0.86 (m, 2H).

Example B21: Synthesis of Compound 18

-continued

Compound 18

2-fluoro-5-(1-methyl-4-(trifluoromethyl)-1H-imidazol-2-yl)pyridine

To a solution of 2-fluoro-5-(4-(trifluoromethyl)-1H-imidazol-2-yl)pyridine (5.00 g, 21.63 mmol) in DMF (50 mL) were added Cs$_2$CO$_3$ (14.10 g, 43.28 mmol) and iodomethane (4.61 g, 32.48 mmol). The reaction mixture was stirred at rt for 16 hr under Ar. To the mixture was added water (300 mL). After extraction with EtOAc (200 mL×2), the combined organic layers were washed with brine (200 mL), dried over Na$_2$SO$_4$, filtered and concentrated under reduced pressure to give a residue, which was purified by column chromatography on silica gel eluting with ethyl acetate (from 0% to 11%) in petroleum ether to give the title compound (4.09 g, 16.68 mmol, 77% yield) as a white solid.

LC-MS (ESI+): m/z 246.1 (M+H)$^+$.

3-(4-cyclopropyl-6-methoxypyrimidin-5-yl)-1-(methyl-d3)-5-(5-(1-methyl-4-(trifluoromethyl)-1H-imidazol-2-yl)pyridin-2-yl)-4,5,6,7-tetrahydro-1H-pyrazolo[4,3-c]pyridine A mixture of 3-(4-cyclopropyl-6-methoxypyrimidin-5-yl)-1-(methyl-d$_3$)-4,5,6,7-tetrahydro-1H-pyrazolo[4,3-c]pyridine (200 mg, 0.69 mmol) (see Example B9 for synthesis), 2-fluoro-5-(1-methyl-4-(trifluoromethyl)-1H-imidazol-2-yl)pyridine (255 mg, 1.04 mmol) and TEA (0.29 mL, 2.10 mmol) in DMF (5 mL) was stirred at 100° C. for 16 hr. After cooling to rt, to the mixture was added water (20 mL). After extraction with EtOAc (20 mL×2), the combined organic layers were washed with brine (20 mL), dried over Na$_2$SO$_4$, filtered and concentrated under reduced pressure to give a residue, which was purified by prep-TLC (PE/EA=1/3) to give the title compound (91.92 mg, 0.18 mmol, 26% yield).

LC-MS (ESI+): m/z 514.2 (M+H)$^+$.

$^1$HNMR (400 MHz, DMSO-d$_6$) δ=8.62 (s, 1H), 8.41 (d, J 2.4 Hz, 1H), 7.90-7.80 (m, 2H), 7.03 (d, J=9.2 Hz, 1H), 4.46 (s, 2H), 4.03 (t, J=5.6 Hz, 2H), 3.91 (s, 3H), 3.74 (s, 3H), 2.86 (t, J=5.6 Hz, 2H), 2.24-2.11 (m, 1H), 1.09-1.00 (m, 2H), 0.98-0.87 (m, 2H).

Example B22: Synthesis of Compound 20

Intermediate D-1

-continued 20.1

20.2

Compound 20

3-iodo-4,5,6,7-tetrahydro-1H-pyrazolo[4,3-c]pyridine

To a solution of tert-butyl 3-iodo-1,4,6,7-tetrahydro-5H-pyrazolo[4,3-c]pyridine-5-carboxylate (1.00 g, 2.86 mmol) in DCM (20 mL) was added TFA (2.13 mL, 28.58 mmol). The reaction mixture was stirred at rt for 2 hr. Then the mixture was concentrated and dissolved in DCM (20 mL). NaHCO$_3$ powder was added to adjust pH to 7-8. The suspension was filtered. The filtrate was concentrated to give a residue. The residue was purified by column chromatography on silica gel (eluting with 2.5% to 10% MeOH in DCM) to give the title compound (1.10 g, crude) as a brown oil, which was used in next step directly.

LC-MS (ESI+): m/z 249.9 (M+H)$^+$.

3-iodo-5-(5-(1-isopropyl-4-(trifluoromethyl)-1H-imidazol-2-yl)pyridin-2-yl)-4,5,6,7-tetrahydro-1H-pyrazolo[4,3-c]pyridine To a solution of 3-iodo-4,5,6,7-tetrahydro-1H-pyrazolo[4,3-c]pyridine (715 mg, crude, 1.86 mmol) in DMF (10 mL) were added 2-fluoro-5-(1-isopropyl-4-(trifluoromethyl)-1H-imidazol-2-yl)pyridine (658 mg, 2.41 mmol) and TEA (0.84 mL, 6.07 mmol). The reaction mixture was stirred at 100° C. for 16 hr. After cooling to rt, to the mixture was added water (30 mL). After extraction with EtOAc (200 mL×2), the combined organic layers were washed with brine (30 mL), dried over Na$_2$SO$_4$, filtered and concentrated under reduced pressure to give a residue, which was purified by column chromatography on silica gel (eluting with 0-70% EtOAc in PE) to give the title compound (270 mg, 0.54 mmol, 29%) as a yellow solid.

LC-MS (ESI+): m/z 503.1 (M+H)$^+$.

3-(4-cyclopropyl-6-methoxypyrimidin-5-yl)-5-(5-(1-isopropyl-4-(trifluoromethyl)-1H-imidazol-2-yl)pyridin-2-yl)-4,5,6,7-tetrahydro-1H-pyrazolo[4,3-c]pyridine To a mixture of 3-iodo-5-(5-(1-isopropyl-4-(trifluoromethyl)-1H-imidazol-2-yl)pyridin-2-yl)-4,5,6,7-tetrahydro-1H-pyrazolo[4,3-c]pyridine (230 mg, 0.46 mmol), 4-cyclopropyl-6-methoxy-5-(4,4,5,5-tetramethyl-1,3,2-dioxaborolan-2-yl)pyrimidine (164 mg, 0.59 mmol) and K$_2$CO$_3$ (126 mg, 0.91 mmol) in dioxane (8 mL) and H$_2$O (0.8 mL) was added Pd(PPh$_3$)$_4$ (105 mg, 0.09 mmol). The reaction mixture was stirred at 100° C. for 16 hr. After cooling to rt, to the mixture was added water (20 mL). After extraction with EtOAc (20 mL×3), the combined organic layers were washed with brine (30 mL), dried over Na$_2$SO$_4$, filtered and concentrated under reduced pressure to give a residue, which was purified by prep-TLC (PE/EtOAc=1/3) to give the title compound (43.30 mg, 0.08 mmol, 17%).

LC-MS (ESI+): m/z 525.3 (M+H)$^+$.

$^1$HNMR (400 MHz, CDCl$_3$) δ=8.63 (s, 1H), 8.30 (s, 1H), 7.73 (d, J=8.0 Hz, 1H), 7.39 (s, 1H), 6.76 (d, J=8.8 Hz, 1H), 4.56 (s, 2H), 4.55-4.48 (m, 1H), 4.14-4.06 (m, 2H), 3.98 (s, 3H), 3.03-2.94 (m, 2H), 2.02-1.94 (m, 1H), 1.45 (d, J=6.4 Hz, 6H), 1.28-1.20 (m, 2H), 1.04-0.96 (m, 2H).

Example B23: Synthesis of Compound 21

Compound 10

Compound 21

6-cyclopropyl-5-(5-(5-(1-isopropyl-4-(trifluorom-
ethyl)-1H-imidazol-2-yl)pyridin-2-yl)-1-methyl-4,5,
6,7-tetrahydro-1H-pyrazolo[4,3-c]pyridin-3-yl)py-
rimidin-4-ol A solution of 3-(4-cyclopropyl-6-methoxypyrimidin-5-
yl)-5-(5-(1-isopropyl-4-(trifluoromethyl)-1H-imidazol-2-yl)
pyridin-2-yl)-1-methyl-4,5,6,7-tetrahydro-1H-pyrazolo[4,3-
c]pyridine (70 mg, 0.13 mmol) in HCl (6 mL, 3M in MeOH)
was stirred at 100° C. for 16 hr.

After cooling to rt, the mixture was concentrated under
reduced pressure to give a residue, which was purified by
pre-HPLC (column: Waters X bridge C18 10 um OBD
19*250 mm; mobile phase: [0.1% NH$_4$HCO$_3$ in water-
MeCN]; B %: 30%-95%, 6.48 min)) to give the title com-
pound (24.00 mg, 0.05 mmol, 38% yield).

LC-MS (ESI+): m/z 525.2 (M+H)$^+$.

$^1$HNMR (400 MHz, DMSO-d$_6$) δ=12.37 (br s, 1H), 8.25
(d, J 2.4 Hz, 1H), 8.12 (s, 1H), 8.08 (s, 1H), 7.73-7.64 (m,
1H), 7.01 (d, J=8.8 Hz, 1H), 4.46 (s, 2H), 4.45-4.35 (m, 1H),
4.01 (t, J=5.6 Hz, 2H), 3.73 (s, 3H), 2.83 (t, J=5.6 Hz, 2H),
2.28-2.16 (m, 1H), 1.39 (d, J=6.8 Hz, 6H), 1.03-0.94 (m,
2H), 0.89-0.82 (m, 2H).

Example B24: Synthesis of Compound 24

24.1

24.2

24.3

-continued 24.4

Compound 24

3-bromo-2-(difluoromethoxy)pyridine 3-bromopyridin-2-ol (10.00 g, 57.47 mmol) was dis-
solved in MeCN (100 mL). Then 2, 2-difluoro-2-(fluoro-
sulfonyl) acetic acid (15.34 g, 86.14 mmol) and sodium
sulfate (8.97 g, 63.15 mmol) were added at 0° C. within 20
minutes. The reaction mixture was warmed to rt and stirred
at rt for 16 hr. Then the mixture was filtered and concen-
trated. To the residue was added water (50 mL). After
extraction with ethyl acetate (70 mL×3), the combined
organic layers were washed with saturated sodium bicar-
bonate aqueous solution (30 mL), brine (80 mL), dried over
Na$_2$SO$_4$, filtered and concentrated under reduced pressure to
give a residue, which was purified by column chromatog-
raphy on silica gel eluted with 5% to 15% ethyl acetate in
petroleum ether to give the title product (9.96 g, 44.46
mmol, 77% yield) as a yellow oil.

$^1$H NMR (400 MHz, CDCl$_3$) δ=8.13 (dd, J=1.6 Hz, J=4.8
Hz, 1H), 7.94 (dd, J=1.6 Hz, J=7.6 Hz, 1H), 7.65-7.27 (m,
1H), 7.01 (dd, J=4.8 Hz, J=7.6 Hz, 1H).

2-(difluoromethoxy)-3-(4,4,5,5-tetramethyl-1,3,2-
dioxaborolan-2-yl)pyridine

To a solution of 3-bromo-2-(difluoromethoxy)pyridine
(100 mg, 0.45 mmol) in dioxane (10 mL) were added
4,4,4',4',5,5,5',5'-octamethyl-2,2'-bi(1,3,2-dioxaborolane)
(168 mg, 0.66 mmol), KOAc (131.5 mg, 1.34 mmol) and
Pd(dppf)Cl$_2$ (32.67 mg, 0.04 mmol). The reaction mixture
was stirred at 100° C. for 16 hr. After cooling to rt, the
mixture was concentrated under reduced pressure. To the
residue was added water (10 mL). After extraction with ethyl
acetate (10 mL×3), the combined organic layers were
washed with brine (15 mL), dried over Na$_2$SO$_4$, filtered and
concentrated under reduced pressure to give a residue, which
was purified by pre-TLC (PE/EA=3/1) to give the title
compound (75 mg, 0.28 mmol, 62% yield) as a colorless oil.
LC-MS (ESI+): m/z 272.1 (M+H)$^+$.

tert-butyl 3-(2-(difluoromethoxy)pyridin-3-yl)-1-
methyl-1,4,6,7-tetrahydro-5H-pyrazolo[4,3-c]pyri-
dine-5-carboxylate To a mixture of tert-butyl 3-iodo-1-methyl-1,4,6,7-tetra-
hydro-5H-pyrazolo[4,3-c]pyridine-5-carboxylate (500 mg, 1.38 mmol), 2-(difluoromethoxy)-3-(4,4,5,5-tetramethyl-1,3,2-dioxaborolan-2-yl)pyridine (560 mg, 2.07 mmol) and Na$_2$CO$_3$ (146 mg, 1.38 mmol) in dioxane/water (5 mL/1 mL) was added Pd(dppf)Cl$_2$ (114 mg, 0.14 mmol). The reaction mixture was stirred at 100° C. for 16 hr. After cooling to rt, the mixture was concentrated and diluted with water (20 mL). The resulting mixture was extracted with ethyl acetate (20 mL×3). The combined organic layers were washed with brine (30 mL), dried over Na$_2$SO$_4$, filtered and concentrated to give a residue, which was purified by column chromatography on silica gel eluted with 5%~20% ethyl acetate in petroleum ether to give the title compound (330 mg, 0.87 mmol, 63% yield) as a white solid.

LC-MS (ESI+): m/z 381.1 (M+H)$^+$.

3-(2-(difluoromethoxy)pyridin-3-yl)-1-methyl-4,5,6,7-tetrahydro-1H-pyrazolo[4,3-c]pyridine To a solution of tert-butyl 3-(2-(difluoromethoxy)pyridin-3-yl)-1-methyl-1,4,6,7-tetrahydro-5H-pyrazolo[4,3-c]pyridine-5-carboxylate (330 mg, 0.87 mmol) in DCM (10 mL) was added TFA (989 mg, 8.67 mmol). The reaction mixture was stirred at rt for 2 hr. Then the mixture was concentrated and diluted with ethyl acetate (10 mL). The pH of the resulting mixture was adjusted to 8-9 with NaHCO$_3$ powder. Then the mixture was filtered. The filtrate was concentrated to give a residue, which was purified by pre-TLC (DCM/MeOH=10/1) to give the title product (160 mg, 0.57 mmol, 66% yield) as white solid.

LC-MS (ESI+): m/z 281.2 (M+H)$^+$.

3-(2-(difluoromethoxy)pyridin-3-yl)-1-methyl-5-(4-(1-methyl-4-(trifluoromethyl)-1H-imidazol-2-yl)phenyl)-4,5,6,7-tetrahydro-1H-pyrazolo[4,3-c]pyridine To a mixture of 3-(2-(difluoromethoxy)pyridin-3-yl)-1-methyl-4,5,6,7-tetrahydro-1H-pyrazolo[4,3-c]pyridine (160 mg, 0.57 mmol), 2-(4-bromophenyl)-1-methyl-4-(trifluoromethyl)-1H-imidazole (348 mg, 1.14 mmol), X-Phos (544 mg, 1.14 mmol) and sodium tert-butoxide (110 mg, 1.14 mmol) in toluene (10 mL) was added Pd(OAc)$_2$ (12.82 mg, 0.06 mmol). The reaction mixture was stirred at 100° C. for 16 hr. After cooling to rt, the mixture was concentrated and diluted with water (10 mL). The resulting mixture was extracted with ethyl acetate (10 mL×3). The combined organic layers were washed with brine (20 mL), dried over Na$_2$SO$_4$, filtered and concentrated under reduced pressure to give a residue, which was purified by pre-TLC (PE/EA=2/1) to give the title compound (106.00 mg, 0.21 mmol, 37% yield).

LC-MS (ESI+): m/z 505.1 (M+H)$^+$.

$^1$H NMR (400 MHz, DMSO-d$_6$) δ=8.29 (dd, J=2.0 Hz, J=4.8 Hz, 1H), 8.08-7.67 (m, 3H), 7.51 (d, J=8.8 Hz, 2H), 7.35 (dd, J=4.8 Hz, J=7.2 Hz, 1H), 7.08 (d, J=8.8 Hz, 2H), 4.35 (s, 2H), 3.81-3.74 (m, 5H), 3.73 (s, 3H), 2.85 (t, J=5.6 Hz, 2H).

Example B25: Synthesis of Compound 25

10.1

-continued 25.1

Intermediate D
TEA, DMF
100° C., 16 hr

Compound 25

5-(1-ethyl-4-(trifluoromethyl)-1H-imidazol-2-yl)-2-fluoropyridine

To a solution of 2-fluoro-5-(4-(trifluoromethyl)-1H-imidazol-2-yl)pyridine (3.00 g, 12.98 mmol) in DMF (30 mL) was added NaH (0.78 g, 19.5 mmol, 60% dispersion in mineral oil) at 0° C. The mixture was stirred at 0° C. for 30 minutes. Then iodoethane (3.04 g, 19.49 mmol) was added to the mixture at 0° C. The mixture was stirred at rt for 16 hr. Then to the mixture was added water (100 mL). After extraction with EtOAc (100 mL×2), the combined organic layers were washed with brine (100 mL), dried over Na$_2$SO$_4$, filtered and concentrated under reduced pressure to give a residue, which was purified by column chromatography on silica gel eluting with ethyl acetate (from 0% to 11%) in petroleum ether to give the title compound (1.64 g, 6.33 mmol, 49% yield) as a yellow solid.

LC-MS (ESI+): m/z 260.1 (M+H)$^+$.

3-(4-cyclopropyl-6-methoxypyrimidin-5-yl)-5-(5-(1-ethyl-4-(trifluoromethyl)-1H-imidazol-2-yl)pyridin-2-yl)-1-methyl-4,5,6,7-tetrahydro-1H-pyrazolo[4,3-c]pyridine A mixture of 3-(4-cyclopropyl-6-methoxypyrimidin-5-yl)-1-methyl-4,5,6,7-tetrahydro-1H-pyrazolo[4,3-c]pyridine (150 mg, 0.53 mmol), 5-(1-ethyl-4-(trifluoromethyl)-1H-imidazol-2-yl)-2-fluoropyridine (204 mg, 0.79 mmol) and TEA (160 mg, 1.58 mmol) in DMF (5 mL) was stirred at 100° C. for 16 hr. After cooling to rt, to the mixture was added water (20 mL). After extraction with EtOAc (20 mL×2), the combined organic layers were washed with brine (30 mL), dried over Na$_2$SO$_4$, filtered and concentrated under reduced pressure to give a residue, which was purified by prep-TLC (PE/EA=1/3) to give the title compound (75.28 mg, 0.14 mmol, 26% yield).

LC-MS (ESI+): m/z 525.2 (M+H)$^+$.

$^1$HNMR (400 MHz, DMSO-d$_6$) δ=8.63 (d, J=4.0 Hz, 1H), 8.32 (d, J=2.4 Hz, 1H), 7.97 (d, J=1.2 Hz, 1H), 7.77 (dd,

J=2.4 Hz, 9.2 Hz, 1H), 7.03 (d, J=8.8 Hz, 1H), 4.46 (s, 2H), 4.12-3.98 (m, 4H), 3.91 (s, 3H), 3.76 (s, 3H), 2.86 (t, J=5.2 Hz, 2H), 2.24-2.11 (m, 1H), 1.32 (t, J=7.6 Hz, 3H), 1.09-1.00 (m, 2H), 0.98-0.87 (m, 2H).

Synthesis of intermediate 26.1

5-bromopyrimidine-2-carbaldehyde

DIBAL-H (6.49 mL, 6.49 mmol, 1M in THF) was added dropwise to a cooled solution of ethyl 5-bromopyrimidine-2-carboxylate (1.00 g, 4.33 mmol) in THF (10 mL) at −75° C. The reaction mixture was stirred at −75° C. for 1 hr. Then the mixture was quenched by addition of saturated $NH_4C_1$ aqueous solution (20 mL) and EtOAc (20 mL). 2N HCl aqueous solution (4 mL) was added to clear the emulsion formed. The mixture was extracted with EtOAc (20 mL×3). The combined organic layers were washed with brine (30 mL), dried over $Na_2SO_4$, filtered and concentrated under reduced pressure to give a crude product (450 mg, 2.41 mmol, 56% yield), which was used in next step directly.

Example B26: Synthesis of Compound 26

3-(4-cyclopropyl-6-methoxypyrimidin-5-yl)-1-methyl-5-(2-(1-methyl-4-(trifluoromethyl)-1H-imi-dazol-2-yl)pyrimidin-5-yl)-4,5,6,7-tetrahydro-1H-pyrazolo[4,3-c]pyridine Compound 26

In a similar fashion according to the procedure for Compound 6, Compound 26 was synthesized by replacing 5-bromopicolinaldehyde with (intermediate 26.1) 5-bromopyrimidine-2-carbaldehyde. The crude product was purified by prep-TLC (DCM/MeOH=20/1) to give the title compound (27.47 mg, 19% yield).

LC-MS (ESI+): m/z 512.3 (M+H)$^+$.
$^1$H NMR (400 MHz, DMSO-d$_6$) δ=8.67 (s, 2H), 8.63 (s, 1H), 7.93 (s, 1H), 4.27 (s, 2H), 3.97 (s, 3H), 3.92 (s, 3H), 3.91-3.83 (m, 2H), 3.75 (s, 3H), 2.94-2.86 (m, 2H), 2.18-2.04 (m, 1H), 1.08-1.00 (m, 2H), 0.96-0.85 (m, 2H).

Example B27: Synthesis of 27

Compound 27

2-chloro-5-(4-(trifluoromethyl)-1H-imidazol-2-yl) pyrimidine

A mixture of 3,3-dibromo-1,1,1-trifluoropropan-2-one (3.60 g, 13.34 mmol) and NaOAc (1094 mg, 13.34 mmol) in $H_2O$ (5 mL) was stirred at 100° C. for 1 hr. After cooling to rt, a mixture of 2-chloropyrimidine-5-carbaldehyde (950 mg, 6.66 mmol), MeOH (10 mL) and $NH_4OH$ (10 mL) was added. The resulting mixture was stirred at rt for 16 hr. Then to the mixture was added water (50 mL). After extraction with EtOAc (50 mL×3), the combined organic layers were washed with brine (70 mL), dried over $Na_2SO_4$, filtered and concentrated under reduced pressure to give a residue, which was purified by column chromatography on silica gel eluting with ethyl acetate (from 0% to 20%) in petroleum ether to give the title compound (970 mg, 3.90 mmol, 59% yield).
LC-MS (ESI+): m/z 249.1 (M+H)$^+$.

2-chloro-5-(1-methyl-4-(trifluoromethyl)-1H-imida-zol-2-yl)pyrimidine 2-chloro-5-(4-(trifluoromethyl)-1H-imidazol-2-yl)py-rimidine (950 mg, 3.82 mmol) was dissolved in DMF (10 mL). Cs$_2$CO$_3$ (1867 mg, 5.73 mmol) was added. The mixture was cooled to 0° C. and stirred at 0° C. for 30 min. Then CH$_3$I (813 mg, 5.73 mmol) was added. The reaction mixture was stirred at rt for 16 hr. Then to the mixture was added water (30 mL). After extraction with EtOAc (20 mL×3), the combined organic layers were washed with brine (50 mL), dried over Na$_2$SO$_4$, filtered and concentrated under reduced pressure to give a residue, which was purified by column chromatography on silica gel eluting with ethyl acetate (from 1% to 15%) in petroleum ether to give the title compound (480 mg, 1.83 mmol, 48% yield).

LC-MS (ESI+): m/z 263.1 (M+H)$^+$.

3-(4-cyclopropyl-6-methoxypyrimidin-5-yl)-1-methyl-5-(5-(1-methyl-4-(trifluoromethyl)-1H-imi-dazol-2-yl)pyrimidin-2-yl)-4,5,6,7-tetrahydro-1H-pyrazolo[4,3-c]pyridine To a solution of 3-(4-cyclopropyl-6-methoxypyrimidin-5-yl)-1-methyl-4,5,6,7-tetrahydro-1H-pyrazolo[4,3-c]pyri-dine (245 mg, 0.86 mmol) and 2-chloro-5-(1-methyl-4-(trifluoromethyl)-1H-imidazol-2-yl)pyrimidine (150 mg, 0.57 mmol) in i-PrOH (5 mL) was added DIPEA (0.28 mL, 1.61 mmol). The reaction mixture was stirred at 100° C. for 16 hr. After cooling to rt, the mixture was concentrated. To the residue was added water (15 mL). After extraction with EtOAc (20 mL×3), the combined organic layers were washed with brine (40 mL), dried over Na$_2$SO$_4$, filtered and concentrated under reduced pressure to give a residue, which was purified by prep-TLC (PE/EA=1/3) to give the title compound (122.65 mg, 0.24 mmol, 42% yield). LC-MS (ESI+): m/z 512.1 (M+H)$^+$.

$^1$H NMR (400 MHz, DMSO-d$_6$) δ=8.69 (s, 2H), 8.62 (s, 1H), 7.93 (s, 1H), 4.66 (s, 2H), 4.20 (t, J=6.0 Hz, 2H), 3.91 (s, 3H), 3.76 (d, J=4.8 Hz, 6H), 2.87 (t, J=4.8 Hz, 2H), 2.25-2.13 (m, 1H), 1.07-1.00 (m, 2H), 0.98-0.90 (m, 2H).

Example B28: Synthesis of Compound 28

3-(4-cyclopropyl-6-methoxypyrimidin-5-yl)-1-methyl-5-(5-(1-methyl-4-(trifluoromethyl)-1H-imi-dazol-2-yl)pyrazin-2-yl)-4,5,6,7-tetrahydro-1H-pyra-zolo[4,3-c]pyridine Compound 28

In a similar fashion according to the procedure for Compound 27, Compound 28 was synthesized by replacing 2-chloropyrimidine-5-carbaldehyde with 5-chloropyrazine-2-carbaldehyde. In the last step, TEA in DMF was used.

The crude product was purified by prep-TLC (DCM/MeOH=20/1) to afford the title compound (12.14 mg, 8% yield).

LC-MS (ESI+): m/z 512.3 (M+H)$^+$.

$^1$H NMR (400 MHz, DMSO-d$_6$) δ=8.65 (s, 1H), 8.62 (s, 1H), 8.48 (s, 1H), 7.92 (s, 1H), 4.53 (s, 2H), 4.08 (t, J=5.2 Hz, 2H), 3.95 (s, 3H), 3.91 (s, 3H), 3.75 (s, 3H), 2.90 (t, J=4.8 Hz, 2H), 2.22-2.13 (m, 1H), 1.09-1.00 (m, 2H), 0.97-0.87 (m, 2H).

Synthesis of Intermediate 29.1

6-chloropyridazine-3-carbaldehyde

DIBAL-H (5.36 mL, 5.36 mmol, 1M in THF) was added dropwise to a solution of ethyl 6-chloropyridazine-3-car-boxylate (500 mg, 2.68 mmol) in THF (10 mL) at 0° C. under N$_2$. The mixture was stirred at 0° C. for 0.5 hr. Then the mixture was quenched with 20 mL of ice water, 1N HCl aqueous solution (15 mL) and then neutralized with satu-rated sodium bicarbonate aqueous solution (15 mL) at 0° C. The resulting mixture was extracted with dichloromethane (20 mL×3). The combined organic phases were washed with brine (20 mL), dried over Na$_2$SO$_4$, filtered and concentrated to give the title compound (350 mg, 2.46 mmol, 92% yield) as a brown oil, which was used in nest step directly.

$^1$H NMR (400 MHz, CDCl$_3$) δ 10.36 (s, 1H), 8.02 (d, J=8.4 Hz, 1H), 7.72 (dd, J=8.8, 0.4 Hz, 1H).

Example B29: Synthesis of Compound 29

3-(4-cyclopropyl-6-methoxypyrimidin-5-yl)-1-methyl-5-(6-(1-methyl-4-(trifluoromethyl)-1H-imi-dazol-2-yl)pyridazin-3-yl)-4,5,6,7-tetrahydro-1H-pyrazolo[4,3-c]pyridine Compound 29

In a similar fashion according to the procedure for Compound 28, Compound 29 was synthesized by replacing 5-chloropyrazine-2-carbaldehyde with (intermediate 29.1) 6-chloropyridazine-3-carbaldehyde.

The crude product was purified by prep-TLC (DCM/ MeOH=20:1) to give the title compound (13.15 mg, 9% yield).

LC-MS (ESI+): m/z 512.4 (M+H)$^+$.

$^1$H NMR (400 MHz, DMSO-d$_6$) δ=8.62 (s, 1H), 8.01-7.90 (m, 2H), 7.51 (d, J=10.0 Hz, 1H), 4.56 (s, 2H), 4.11 (t, J=5.6 Hz, 2H), 4.04 (s, 3H), 3.91 (s, 3H), 3.76 (s, 3H), 2.91 (t, J=4.8 Hz, 2H), 2.24-2.12 (m, 1H), 1.10-1.00 (m, 2H), 0.97-0.89 (m, 2H).

Example B30: Synthesis of Compound 30

Compound 30

3-(4-cyclopropyl-6-methoxypyrimidin-5-yl)-5-(3-fluoro-4-(1-methyl-4-(trifluoromethyl)-1H-imidazol-2-yl)phenyl)-1-(methyl-d3)-4,5,6,7-tetrahydro-1H-pyrazolo[4,3-c]pyridine To a mixture of 3-(4-cyclopropyl-6-methoxypyrimidin-5-yl)-1-(methyl-d3)-4,5,6,7-tetrahydro-1H-pyrazolo[4,3-c] pyridine (150 mg, 0.52 mmol) (see example B9 for synthesis), 2-(4-bromo-2-fluorophenyl)-1-methyl-4-(trifluoromethyl)-1H-imidazole (336 mg, 1.04 mmol) (see Example B13 for synthesis), t-BuONa (399.9 mg, 4.16 mmol) and X-Phos (496 mg, 1.04 mmol) in toluene (6 mL) was added Pd(OAc)$_2$ (11.68 mg, 0.052 mmol). The reaction mixture was stirred at 100° C. for 16 hr. After cooling to rt, to the mixture was added water (30 mL). After extraction with EtOAc (30 mL×2), the combined organic layers were washed with brine (20 mL), dried over Na$_2$SO$_4$, filtered and concentrated under reduced pressure to give a residue, which was purified by prep-TLC (PE/EA=1/3) to give the title compound (93.61 mg, 0.18 mmol, 35% yield).

LC-MS (ESI+): m/z 531.2 (M+H)$^+$.

$^1$HNMR (400 MHz, DMSO-d$_6$) δ=8.62 (s, 1H), 7.90 (s, 1H), 7.33 (t, J=8.8 Hz, 1H), 7.01-6.88 (m, 2H), 4.18 (s, 2H), 3.91 (s, 3H), 3.81 (t, J=5.6 Hz, 2H), 3.56 (s, 3H), 2.85 (t, J 5.6 Hz, 2H), 2.20-2.10 (m, 1H), 1.08-1.00 (m, 2H), 0.96-0.86 (m, 2H).

Example B31: Synthesis of Compound 31

Compound 31

3-(4-cyclopropyl-6-methoxypyrimidin-5-yl)-1-(difluoromethyl)-5-(5-(1-methyl-4-(trifluoromethyl)-1H-imidazol-2-yl)pyridin-2-yl)-4,5,6,7-tetrahydro-1H-pyrazolo[4,3-c]pyridine To a solution of 3-(4-cyclopropyl-6-methoxypyrimidin-5-yl)-1-(difluoromethyl)-4,5,6,7-tetrahydro-1H-pyrazolo[4, 3-c]pyridine (100 mg, 0.31 mmol) (see Example B14 for synthesis) in DMF (3 mL) were added 2-fluoro-5-(1-methyl-4-(trifluoromethyl)-1H-imidazol-2-yl)pyridine (114 mg, 0.46 mmol) and TEA (0.13 mL, 0.94 mmol) at rt. The reaction mixture was stirred at 100° C. for 48 hr under N$_2$ atmosphere. After cooling to rt, to the mixture was added water (15 mL). After extraction with EtOAc (20 mL×3), the combined organic layers were washed with brine (20 mL), dried over Na$_2$SO$_4$, filtered and concentrated under reduced pressure to give a residue, which was purified by prep-TLC (PE/EtOAc=1/1) to give the title compound (56.20 mg, 0.10 mmol, 32% yield).

LC-MS (ESI+): m/z 547.3 (M+H)$^+$.

$^1$H NMR (400 MHz, DMSO-d$_6$) δ=8.69 (s, 1H), 8.43 (d, J=2.4 Hz, 1H), 8.03-7.68 (m, 3H), 7.08 (d, J=9.2 Hz, 1H), 4.50 (s, 2H), 4.07 (t, J=5.6 Hz, 2H), 3.94 (s, 3H), 3.75 (s, 3H), 3.04 (t, J=5.2 Hz, 2H), 2.08-1.96 (m, 1H), 1.12-1.04 (m, 2H), 1.01-0.93 (m, 2H).

Example B32: Synthesis of Compound 32

Compound 32

3-(4-cyclopropyl-6-methoxypyrimidin-5-yl)-1-(dif-
luoromethyl)-5-(5-(1-isopropyl-4-(trifluoromethyl)-
1H-imidazol-2-yl)pyridin-2-yl)-4,5,6,7-tetrahydro-
1H-pyrazolo[4,3-c]pyridine To a solution of 3-(4-cyclopropyl-6-methoxypyrimidin-
5-yl)-1-(difluoromethyl)-4,5,6,7-tetrahydro-1H-pyrazolo[4,
3-c]pyridine (100 mg, 0.31 mmol) (see Example B14 for
synthesis) in DMF (3 mL) were added 2-fluoro-5-(1-isopro-
pyl-4-(trifluoromethyl)-1H-imidazol-2-yl)pyridine (128 mg,
0.47 mmol) and TEA (0.13 mL, 0.94 mmol) at rt. The
reaction mixture was stirred at 100° C. for 48 hr under $N_2$
atmosphere. After cooling to rt, to the mixture was added
water (20 mL). After extraction with EtOAc (20 mL×3), the
combined organic layers were washed with brine (25 mL),
dried over $Na_2SO_4$, filtered and concentrated under reduced
pressure to give a residue, which was purified by prep-TLC
(PE/EtOAc=1/1) to give the title compound (47.13 mg, 0.08
mmol, 26% yield).

LC-MS (ESI+): m/z 575.3 (M+H)$^+$.

$^1$H NMR (400 MHz, DMSO-$d_6$) δ=8.69 (s, 1H), 8.27 (d,
J=2.4 Hz, 1H), 8.13 (d, J=1.2 Hz, 1H), 8.03-7.68 (m, 2H),
7.08 (d, J=9.2 Hz, 1H), 4.50 (s, 2H), 4.46-4.37 (m, 1H),
4.11-4.02 (m, 2H), 3.94 (s, 3H), 3.08-3.00 (m, 2H), 2.08-
1.98 (m, 1H), 1.39 (d, J=6.4 Hz, 6H), 1.12-1.03 (m, 2H),
1.02-0.93 (m, 2H).

It is understood that the examples and embodiments
described herein are for illustrative purposes only and that
various modifications or changes in light thereof will be
suggested to persons skilled in the art and are to be included
within the spirit and purview of this application and scope of
the appended claims. All publications, patents, and patent
applications cited herein are hereby incorporated by refer-
ence in their entirety for all purposes.

What is claimed is:

1. A compound having the structure of Formula (VI), or
a pharmaceutically acceptable salt thereof, Formula (VI)

wherein:

is ring A is pyridine or pyrimidine;

each $R^A$ is independently selected from CN, $C_{1-6}$ alkyl,
$C_{3-8}$ cycloalkyl, and —$OR^{11}$, wherein the $C_{3-8}$ cycloal-
kyl is substituted with one or more substituents inde-
pendently selected from halogen, $C_{1-6}$ alkyl, $C_{1-6}$
alkoxyl, $C_{1-6}$ haloalkyl, oxo, $C_{3-6}$ cycloalkyl, and
amino;

$R^{11}$ is hydrogen or $C_{1-6}$ alkyl;

$R^B$ is optionally substituted 5-membered monocyclic het-
eroaryl;

m is 1, 2, 3, or 4; and p is 0 or 1.

2. The compound of claim 1, or a pharmaceutically
acceptable salt thereof, wherein subscript p is 0.

3. The compound of claim 2, or a pharmaceutically
acceptable salt thereof, wherein subscript m is 1, 2, or 3.

4. The compound of claim 3, or a pharmaceutically
acceptable salt thereof, wherein ring A is pyridine.

5. The compound of claim 3, or a pharmaceutically
acceptable salt thereof, wherein ring A is pyrimidine.

6. The compound of claim 3, or a pharmaceutically
acceptable salt thereof, wherein -continued , or

7. The compound of claim 6, or a pharmaceutically acceptable salt thereof, wherein at least one $R^A$ is —$OR^{11}$ or $C_{3-8}$ cycloalkyl.

8. The compound of claim 2, or a pharmaceutically acceptable salt thereof, wherein $R^B$ is imidazole, pyrazole, triazole, or tetrazole, each of which is optionally substituted with one or more substituents selected from $C_{1-3}$ alkyl and $C_{1-3}$ haloalkyl.

9. A compound which is or a pharmaceutically acceptable salt thereof.

10. A pharmaceutical composition comprising a compound of claim 1, or a pharmaceutically acceptable salt thereof, and a pharmaceutically acceptable carrier or excipient.

11. A pharmaceutical composition comprising a compound of claim 9, or a pharmaceutically acceptable salt thereof, and a pharmaceutically acceptable carrier or excipient.

\* \* \* \* \*